US012633422B2

(12) United States Patent
Bagne

(10) Patent No.: US 12,633,422 B2
(45) Date of Patent: May 19, 2026

(54) QUANTIFYING EVIDENCE FOR REGULATORY CONTROL AND MECHANISMS WITH COMPLEX ADAPTIVE SYSTEMS METROLOGY BY COMPUTATION METHODS AND SYSTEMS

(71) Applicant: Bagne-Miller Enterprises, Inc., Troy, MI (US)

(72) Inventor: Curtis A. Bagne, Troy, MI (US)

(73) Assignee: Bagne-Miller Enterprises, Inc., Troy, MI (US)

( * ) Notice: Subject to any disclaimer, the term of this patent is extended or adjusted under 35 U.S.C. 154(b) by 0 days.

(21) Appl. No.: 19/356,584

(22) Filed: Oct. 13, 2025

(65) Prior Publication Data

US 2026/0038700 A1 Feb. 5, 2026

Related U.S. Application Data

(63) Continuation of application No. 18/428,980, filed on Jan. 31, 2024, now Pat. No. 12,469,609, which is a continuation of application No. 18/085,278, filed on Dec. 20, 2022, now Pat. No. 11,935,659, which is a continuation of application No. 17/551,110, filed on Dec. 14, 2021, now Pat. No. 11,538,592.

(Continued)

(51) Int. Cl.
*G16H 50/70* (2018.01)
*G05B 13/04* (2006.01)
*G06F 17/18* (2006.01)

(52) U.S. Cl.
CPC ........... *G16H 50/70* (2018.01); *G05B 13/041* (2013.01); *G05B 13/047* (2013.01); *G06F 17/18* (2013.01)

(58) Field of Classification Search
CPC ...... G16H 50/70; G06F 17/18; G05B 13/041; G05B 13/047
See application file for complete search history.

(56) References Cited

U.S. PATENT DOCUMENTS

| | | | |
|---|---|---|---|
| 5,251,126 A | 10/1993 | Kahn et al. | |
| 5,262,943 A | 11/1993 | Thibado et al. | |

(Continued)

FOREIGN PATENT DOCUMENTS

| | | |
|---|---|---|
| WO | 2002031604 A1 | 4/2002 |

OTHER PUBLICATIONS

Nguyen, T., Zhou, T., Potter, T., Zou, L., & Zhang, Y. (2019). The cortical network of emotion regulation: Insights from advanced EEG-fMRI integration analysis. IEEE transactions on medical imaging, 38(10), 2423-2433. (Year: 2019).*

(Continued)

*Primary Examiner* — Bijan Mapar
(74) *Attorney, Agent, or Firm* — Aurora Consulting LLC; Kristen J. Hansen; Ashley Sloat

(57) ABSTRACT

Methods and systems are described for a computer-implemented complex adaptive systems metrology (CASM) technique for generating universally and mathematically standardized scores that quantify longitudinal evidence for either temporal-interaction scores or temporal-interaction benefit-and-harm scores to determine a quantitative significance estimate of scores for either standardized temporal-interaction scores or the standardized temporal-interaction benefit-and-harm scores.

36 Claims, 19 Drawing Sheets

Related U.S. Application Data

(60) Provisional application No. 63/125,507, filed on Dec. 15, 2020.

(56) References Cited

U.S. PATENT DOCUMENTS

| | | | |
|---|---|---|---|
| 5,267,139 | A | 11/1993 | Johnson |
| 5,412,769 | A | 5/1995 | Maruoka et al. |
| 5,504,569 | A | 4/1996 | Kato et al. |
| 5,528,516 | A | 6/1996 | Yemini et al. |
| 5,544,281 | A | 8/1996 | Maruoka et al. |
| 5,563,983 | A | 10/1996 | Nozaki et al. |
| 5,640,549 | A | 6/1997 | Powsner et al. |
| 5,672,154 | A | 9/1997 | Sillen et al. |
| 5,694,129 | A | 12/1997 | Fujinawa et al. |
| 5,715,451 | A | 2/1998 | Marlin |
| 5,742,811 | A | 4/1998 | Agrawal et al. |
| 6,051,209 | A | 4/2000 | Metz et al. |
| 6,055,491 | A | 4/2000 | Biliris et al. |
| 6,098,024 | A | 8/2000 | Chen et al. |
| 6,134,510 | A | 10/2000 | Deco et al. |
| 6,173,240 | B1 | 1/2001 | Sepulveda et al. |
| 6,317,700 | B1 | 11/2001 | Bagne |
| 6,516,288 | B2 | 2/2003 | Bagne |
| 9,141,756 | B1 * | 9/2015 | Hillis ......................... G16B 5/00 |
| 11,515,046 | B2 | 11/2022 | Kenedy et al. |
| 2010/0106044 | A1 * | 4/2010 | Linderman ............ A61B 5/411 |
| | | | 600/546 |
| 2016/0113567 | A1 * | 4/2016 | Osvath ................. A61B 5/4812 |
| | | | 600/544 |
| 2018/0294060 | A1 | 10/2018 | Kassab |
| 2022/0044821 | A1 | 2/2022 | Eichler et al. |
| 2023/0154611 | A1 | 5/2023 | Palandurkar et al. |
| 2023/0363679 | A1 | 11/2023 | Wang et al. |
| 2024/0115213 | A1 | 4/2024 | Ramesh et al. |

OTHER PUBLICATIONS

Leistritz, L., Schiecke, K., Astolfi, L., & Witte, H. (2015). Time-variant modeling of brain processes. Proceedings of the IEEE, 104(2), 262-281. (Year: 2015).*

36-Item Short Form Survey (SF-36); Rand Corporation; Retrieved online at: https://www.rand.org/health-care/surveys_tools/mos/36-item-short-form.html.

'Bagne, C., article entitled "A New Metric to Quantify Functional & Effective Connectivity for Individual Brains," DataSpeaks, Inc., Fourth Biennial Conference on Resting State/Brain Connectivity, Sep. 11-13, 2014, Boston/Cambridge, MA, p. 1.

Bagne, C., article entitled "Accelerate Precision Clinical Trials and Precision Medicine by Computing Precision Quantitative Diagnostic Phenotypes for Chronic Disorders," Open Forum Precision Trial Challenge, Mar. 14, 2016, p. 1-17. Retrieved online at https://web.archive.org/web/20191225172453/https://www.hbs.edu/openforum/openforum.hbs.org/goto/contribution/1811.html.

Bagne, C., article entitled "Causality Assessment with Multiple Time Series Data," DataSpeaks, Inc., U-M & DataSpeaks, Jun. 18, 2012, p. 1-61.

Bagne, C., article entitled "DataSpeaks Interactions® Software—A killer App for 21st Century Systems Science and P4 Medicine?" International Symposium, Institute for Systems Biology, Apr. 2008, p. 1-8.

Bagne, C., article entitled "From Genomics to Personalized Medicine with Advances in Measurement and Experimental Design," Critical National Need Idea, p. 1-21.

Bagne, C., brochure entitled "DataSpeaks Interactions®—Breakthrough Software for Systems Biology, Drug Discovery, and Drug Development".

Bagne, C., et al., article entitled "Evaluating the Effects of Drugs on Behavior and Quality of Life: An Alternative Strategy for Clinical Trials," Journal of Consulting and Clinical Psychology, vol. 60, No. 2, 1992, p. 225-239.

Bagne, C., paper entitled "Jump-Start Pharmaceutical Industry Productivity with the Science of Individuality Measurement Algorithm (SIMA)," DataSpeaks, Inc., p. 1-4.

Bagne, C., paper entitled "Legislative Guidance Toward 21st Century Clinical Regulatory Science: A Moonshot for Patient-Centric Drug Development for Chronic Disorders," May 2015, p. 1-6.

Bagne, C., paper entitled "Precision Clinical Drug Development: Four Main Steps to Higher Productivity," DataSpeaks, Inc., p. 1.

Bagne, C., paper entitled "Target the Right Drug to the Right Patient at the Right dose with Streaming Data," DataSpeaks, Inc., p. 1.

Bagne, C., presentation entitled "Precision Drug Development with the Science of Individuality Measurement Algorithm (SIMA)," PMWC 2018, Precision Medicine World Conference, University of Michigan, p. 1-22.

Bagne, C., presentation entitled "Precision Science for Precision Medicine," PMWC 2019, Precision Medicine World Conference, p. 1-30.

Cleophas, T.J., et al., chapter entitled "Clinical Trials do not Use Random Samples Anymore," Statistics Applied to Clinical Trials, 2009, p. 367-368; Retrieved online at: https://link.springer.com/chapter/10.1007/978-1-4020-9523-8_30.

Goncalves, Rui article entitled "Multivariate Time Series Analysis with Deep Learning," from Doctoral Program in Computer Science of the Universities of Minho, Aveiro and Porto dated Mar. 2021.

Greenland, S, et al., article entitled "On Causal Inferences for Personalized Medicine: How Hidden Causal Assumptions Led to Erroneous Causal Claims About the D-Value," Am Stat. 74(3), May 20, 2019, p. 243-248. doi: 10.1080/00031305.2019.1575771. Retrieved online at: https://pubmed.ncbi.nlm.nih.gov/33487634/.

Hampel, H, et al., article entitled "Revolution of Alzheimer Precision Neurology. Passageway of Systems Biology and Neurophysiology," J Alzheimers Dis., 64(s1): S47-S105, 2018, p. 1-3, Retrieved online at: https://pubmed.ncbi.nlm.nih.gov/29562524/.

Hingorani, Aroon D. et al. article titled "Improving the odds of drug development success through human genomics: modeling study," Scientific Reports, (2019) 9:18911, https://doi.org/10.1038/s41598-019-54849-w.

Liu, Zitao et al. article titled "A Personalized Predictive Framework for Multivariate Clinical Time Series via Adaptive Model Selection," Proc ACM Int Conf Inf Knowl Manag. Nov. 2017 ; 2017: 1169-1177. doi: 10.1145/3132847.3132859.

Mora-Cantallops, Marcal et al. article titled "Traceability for Trustworthy AI: A Review of Models and Tools," Big Data Cognitive Computing 2021, 5, 20. https://doi.org/10.3390/bdcc5020020, https://www.mdpi.com/journal/bdcc.

Neto, E., et al., article entitled "Towards Personalized Causal Inference of Medication Response in Mobile Health: An Instrumental Variable Approach for Randomized Trials with Imperfect Compliance," Cornell University, Jul. 31, 2017, p. 1-38; Retrieved online at: https://arxiv.org/abs/1604.01055.

Oprea, T. et al., article entitled "Drug repurposing: far beyond new targets for old drugs." The AAPS Journal vol. 14, No. 4, Dec. 2012, p. 759-763. doi: 10.1208/s12248-012-9390-1, Retrieved online at: https://www.ncbi.nlm.nih.gov/pmc/articles/PMC3475856/.

Packiasabapathy, S., et al., article entitled "Gender, genetics, and analgesia: understanding the differences in response to pain relief." Journal of Pain Research, vol. 11, Nov. 8, 2018, p. 2729-2739, Dovepress, doi:10.2147/JPR.S94650. Retrieved online at: https://www.ncbi.nlm.nih.gov/pmc/articles/PMC6235329/.

Rocca, Elena et al. article titled "Casual Evidence and Dispositions in Medicine and Public Health," International Journal of Environmental Research and Public Health, Int. J. Environ. Res. Public Health 2020, 17, 1813; doi:10.3390/ijerph17061813, www.mdpi.com/journal/ijerph.

Schwartzberg L, et al., article entitled "Precision Oncology: Who, How, What, When, and When Not?" Am Soc Clin Oncol Educ Book, 2017;37, p. 160-169. doi: 10.1200/EDBK_174176. PMID: 28561651. Retrieved online at: https://pubmed.ncbi.nlm.nih.gov/28561651/.

Sonawalla, S., et al., articl entitled "Placebo response in depression," Dialogues in Clinical Neuroscience, vol. 4, No. 1, 2002, p. 105-113. doi: 10.31887/DCNS.2002.4.1/ssonawalla. Retrieved online at: https://www.ncbi.nlm.nih.gov/pmc/articles/PMC3181672/.

(56) References Cited

OTHER PUBLICATIONS

Szedlak, A., et al., article entitled "Cell cycle time series gene expression data encoded as cyclic attractors in Hopfield systems," PLOS Computational Biology, Nov. 17, 2017, p. 1-19. Retrieved online at: https://journals.plos.org/ploscompbiol/article?id=10.1371/journal.pcbi.1005849.

Tank, A., dissertation entitled "Discovering Interactions in Multivariate Time Series," University of Washington, 2018, p. 1-211.

Tuncbag, N., et al., paper entitled "Towards inferring time dimensionality in protein-protein interaction networks by integrating structures: the p53 example," Royal Society of Chemistry, Mol. BioSyst., Jun. 30, 2009, 5, p. 1770-1778. Retrieved online at: https://pubs.rsc.org/en/content/articlehtml/2009/mb/b905661k.

Woodcock, J., et al., article entitled "Master Protocols to Study Multiple Therapies, Multiple Diseases, or Both," The New England Journal of Medicine, 377; 1, Jul. 6, 2017, p. 62-70; Retrieved online at: https://www.nejm.org/doi/full/10.1056/NEJMra1510062.

Yazdani, A, et al., article entitled "Causal Inference in the Age of Decision Medicine." Journal of Data Mining Genomics Proteomics, vol. 6, Jan. 1, 2015, p. 1-14, doi:10.4172/2153-0602.1000163. Retrieved online at: https://www.ncbi.nlm.nih.gov/pmc/articles/PMC4466903/.

\* cited by examiner

| Pt. | $t_1$, BASELINE | | $t_2$, ENDPOINT | | | | | | |
| | C | RV | C | RV | ΔC | ΔRV | $\bar{C}$ | $\bar{RV}$ | B/H |
|---|---|---|---|---|---|---|---|---|---|
| 1 | 1 | 5 | 2 | 10 | 1 | 5 | 1.5 | 7.5 | 1 |
| 2 | 1 | 5 | 2 | 10 | 1 | 5 | 1.5 | 7.5 | 1 |
| 3 | 1 | 5 | 2 | 10 | 1 | 5 | 1.5 | 7.5 | 1 |
| 4 | 2 | 10 | 4 | 20 | 2 | 10 | 3.0 | 15.0 | 1 |
| 5 | 2 | 10 | 4 | 20 | 2 | 10 | 3.0 | 15.0 | 1 |
| 6 | 2 | 10 | 4 | 20 | 2 | 10 | 3.0 | 15.0 | 1 |
| 7 | 3 | 15 | 6 | 30 | 3 | 15 | 4.5 | 22.5 | 1 |
| 8 | 3 | 15 | 6 | 30 | 3 | 15 | 4.5 | 22.5 | 1 |
| 9 | 3 | 15 | 6 | 30 | 3 | 15 | 4.5 | 22.5 | 1 |

$\bar{C}$  = Mean Concentration    $\bar{RV}$ = Mean Response Variable    300
C  = Concentration    Δ  = Change
RV = Response Variable    B&H  = Benefit & Harm Score Scatter plots: Each dot represents 3 patients Strong concentration-response relationships within patients in the absence of a relationship access patients

| Pt. | $t_1$ c | $t_1$ RV | $t_2$ c | $t_2$ RV | $\Delta C$ | $\Delta RV$ | $\bar{C}$ | $\bar{RV}$ | B/H |
|-----|---------|----------|---------|----------|-----------|-------------|-----------|------------|-----|
| 1 | 1 | 5 | 2 | 10 | 1 | 5 | 1.5 | 7.5 | 1 |
| 2 | 1 | 10 | 2 | 20 | 1 | 10 | 1.5 | 15.0 | 1 |
| 3 | 1 | 15 | 2 | 30 | 1 | 15 | 1.5 | 22.5 | 1 |
| 4 | 2 | 5 | 4 | 10 | 2 | 5 | 3.0 | 7.5 | 1 |
| 5 | 2 | 10 | 4 | 20 | 2 | 10 | 3.0 | 15 | 1 |
| 6 | 2 | 15 | 4 | 30 | 2 | 15 | 3.0 | 22.5 | 1 |
| 7 | 3 | 5 | 6 | 10 | 3 | 5 | 4.5 | 7.5 | 1 |
| 8 | 3 | 10 | 6 | 20 | 3 | 10 | 4.5 | 15 | 1 |
| 9 | 3 | 15 | 6 | 30 | 3 | 15 | 4.5 | 22.5 | 1 |

$\bar{C}$  = Mean Concentration     $\bar{RV}$ = Mean Response Variable
C   = Concentration     $\Delta$  = Change
RV  = Response Variable     B&H  = Benefit & Harm Score Scatterplots

400

Figure 5:
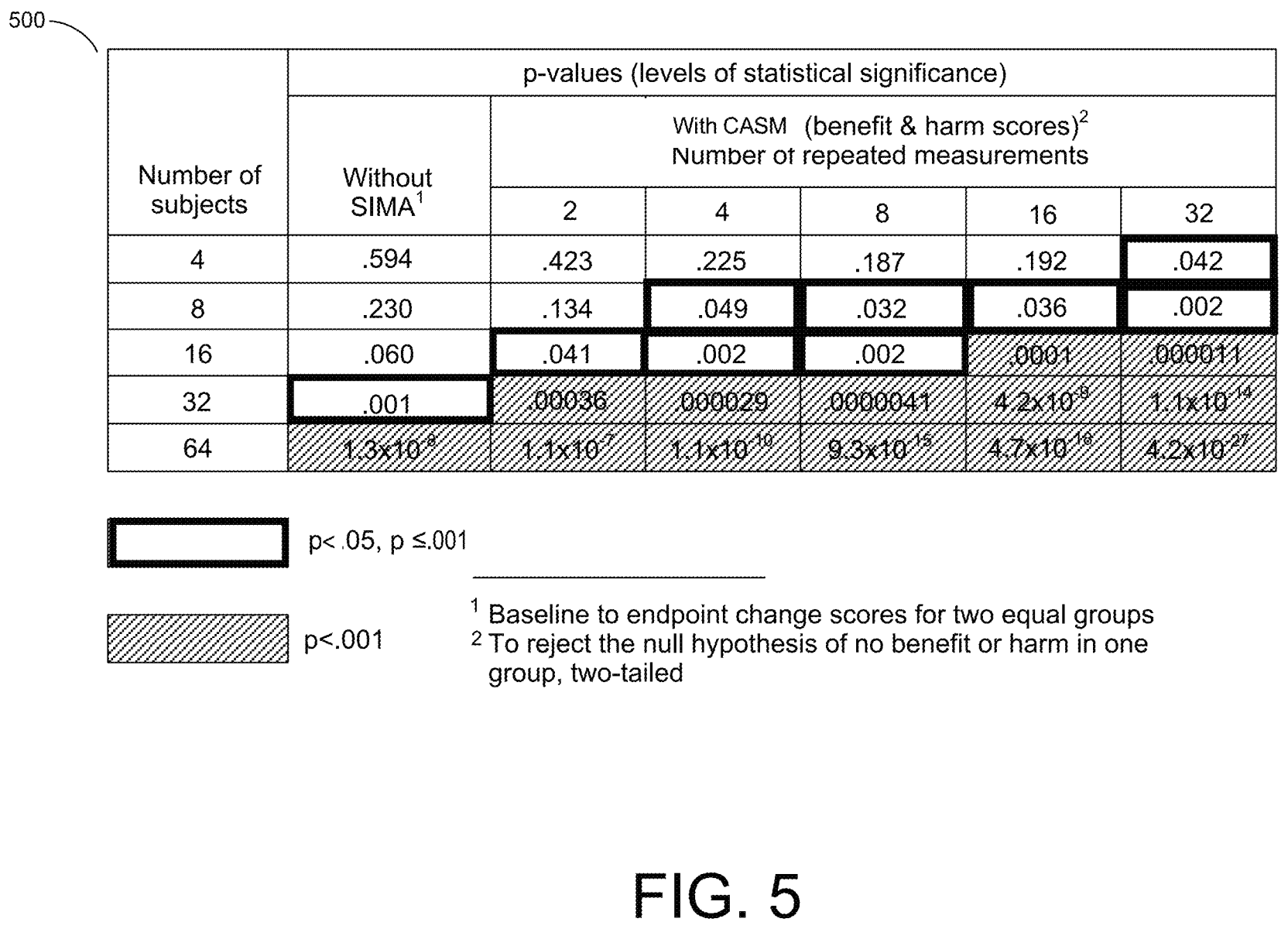

| Number of subjects | Without SIMA[1] | p-values (levels of statistical significance) | | | | |
| --- | --- | --- | --- | --- | --- | --- |
| | | With CASM (benefit & harm scores)[2] Number of repeated measurements | | | | |
| | | 2 | 4 | 8 | 16 | 32 |
| 4 | .594 | .423 | .225 | .187 | .192 | .042 |
| 8 | .230 | .134 | .049 | .032 | .036 | .002 |
| 16 | .060 | .041 | .002 | .002 | .0001 | .000011 |
| 32 | .001 | .00036 | .00029 | .0000041 | $4.2 \times 10^{-9}$ | $1.1 \times 10^{-14}$ |
| 64 | $1.3 \times 10^{-8}$ | $1.1 \times 10^{-10}$ | $1.1 \times 10^{-16}$ | $9.3 \times 10^{-15}$ | $4.7 \times 10^{-16}$ | $4.2 \times 10^{-27}$ |

☐ p< .05, p ≤ .001

▨ p<.001

[1] Baseline to endpoint change scores for two equal groups
[2] To reject the null hypothesis of no benefit or harm in one group, two-tailed

| | Week | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|---|
| Dose | | | | | | | | | | | | | | | | | |
| | One analog time series for Dose | 20 | 20 | 40 | 40 | 0 | 0 | 40 | 40 | 40 | 40 | 20 | 20 | 80 | 80 | 40 | 40 |
| | Set of three digital time series for Dose-Digital independent events (IE) | | | | | | | | | | | | | | | | |
| ≥20 | | 1 | 1 | 1 | 1 | 0 | 0 | 1 | 1 | 1 | 1 | 1 | 1 | 1 | 1 | 1 | 1 |
| ≥40 | | 0 | 0 | 1 | 1 | 0 | 0 | 1 | 1 | 1 | 1 | 0 | 0 | 1 | 1 | 1 | 1 |
| ≥80 | | 0 | 0 | 0 | 0 | 0 | 0 | 0 | 0 | 0 | 0 | 0 | 0 | 1 | 1 | 0 | 0 |
| DV | | | | | | | | | | | | | | | | | |
| | One analog time series for one DV-(e.g., blood pressure BP) | 96 | 98 | 85 | 81 | 91 | 96 | 84 | 87 | 80 | 78 | 93 | 98 | 82 | 77 | 81 | 78 |
| | Set of eleven digital time series for DV-digital dependent events (DE) | | | | | | | | | | | | | | | | |
| ≥78 | | 1 | 1 | 1 | 1 | 1 | 1 | 1 | 1 | 1 | 1 | 1 | 1 | 1 | 0 | 1 | 1 |
| ≥80 | | 1 | 1 | 1 | 1 | 1 | 1 | 1 | 1 | 1 | 0 | 1 | 1 | 1 | 0 | 1 | 0 |
| ≥81 | | 1 | 1 | 1 | 1 | 1 | 1 | 1 | 1 | 0 | 0 | 1 | 1 | 1 | 0 | 1 | 0 |
| ≥82 | | 1 | 1 | 1 | 0 | 1 | 1 | 1 | 1 | 0 | 0 | 1 | 1 | 1 | 0 | 0 | 0 |
| ≥84 | | 1 | 1 | 1 | 0 | 1 | 1 | 1 | 1 | 0 | 0 | 1 | 1 | 0 | 0 | 0 | 0 |
| ≥85 | | 1 | 1 | 1 | 0 | 1 | 1 | 0 | 1 | 0 | 0 | 1 | 1 | 0 | 0 | 0 | 0 |
| ≥87 | | 1 | 1 | 0 | 0 | 1 | 1 | 0 | 1 | 0 | 0 | 1 | 1 | 0 | 0 | 0 | 0 |
| ≥91 | | 1 | 1 | 0 | 0 | 1 | 1 | 0 | 0 | 0 | 0 | 1 | 1 | 0 | 0 | 0 | 0 |
| ≥93 | | 1 | 1 | 0 | 0 | 0 | 1 | 0 | 0 | 0 | 0 | 1 | 1 | 0 | 0 | 0 | 0 |
| ≥96 | | 1 | 1 | 0 | 0 | 0 | 1 | 0 | 0 | 0 | 0 | 0 | 1 | 0 | 0 | 0 | 0 |
| ≥98 | | 0 | 1 | 0 | 0 | 0 | 0 | 0 | 0 | 0 | 0 | 0 | 1 | 0 | 0 | 0 | 0 |

EPISODE CRITERION

|  | 1 | 2 | 3 | 4 | 5 | 6 | 7 | 8 |
|---|---|---|---|---|---|---|---|---|
| EPISODE LENGTH 1 | 1 |  |  |  |  |  |  |  |
| 2 | 2 | 3 |  |  |  |  |  |  |
| 3 | 4 | 5 | 6 |  |  |  |  |  |
| 4 | 7 | 8 | 9 | 10 |  |  |  |  |
| 5 | 11 | 12 | 13 | 14 | 15 |  |  |  |
| 6 | 16 | 17 | 18 | 19 | 20 | 21 |  |  |
| 7 | 22 | 23 | 24 | 25 | 26 | 27 | 28 |  |
| 8 | 29 | 30 | 31 | 32 | 33 | 34 | 35 | 36 |

TIMES (REPEATED MEASUREMENTS)

|  | TRUE DELAY | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| IV |  | 0 | 1 | 0 | 0 | 0 | 0 | 0 | 1 | 1 | 0 | 0 | 0 | 0 | 0 | 0 | 1 | 0 | 0 | 0 | 0 |
| DV | 0 | 0 | 1 | 0 | 0 | 0 | 0 | 0 | 1 | 1 | 0 | 0 | 0 | 0 | 0 | 0 | 1 | 0 | 0 | 0 | 0 |
| DV | 1 | - | 0 | 1 | 0 | 0 | 0 | 0 | 1 | 1 | 1 | 0 | 0 | 0 | 0 | 0 | 0 | 1 | 0 | 0 | 0 |
| DV | 2 | - | - | 0 | 1 | 0 | 0 | 0 | 0 | 0 | 1 | 1 | 0 | 0 | 0 | 0 | 0 | 0 | 1 | 0 | 0 |
| DV | 3 | - | - | - | 0 | 1 | 0 | 0 | 0 | 0 | 0 | 1 | 1 | 0 | 0 | 0 | 0 | 0 | 0 | 1 | 0 |
| DV | 4 | - | - | - | - | 0 | 1 | 0 | 0 | 0 | 0 | 0 | 1 | 1 | 0 | 0 | 0 | 0 | 0 | 0 | 1 |
| DV | 5 | - | - | - | - | - | 0 | 1 | 0 | 0 | 0 | 0 | 0 | 1 | 1 | 0 | 0 | 0 | 0 | 0 | 0 |
| DV | 6 | - | - | - | - | - | - | 1 | 1 | 0 | 0 | 0 | 0 | 0 | 1 | 1 | 0 | 0 | 0 | 0 | 0 |

| TRUE DELAY | Temporal-Interaction Score | | | | | | |
|---|---|---|---|---|---|---|---|
| | 0 | 1 | 2 | 3 | 4 | 5 | 6 |
| 0 | 11.4522 | -.0204 | -.7852 | -.7852 | -.7852 | -.6111 | .1181 |
| 1 | -.0325 | 10.9000 | -.0325 | -.8393 | -.8393 | -.6400 | -.6400 |
| 2 | -.6751 | -.0430 | 10.3349 | .0430 | -.9045 | -.6751 | -.6751 |
| 3 | -.7181 | -.7181 | -.0515 | 9.7560 | -.0515 | -.7181 | -.7181 |
| 4 | -.7716 | -.7716 | -.7716 | 0 | 9.1623 | .0215 | -.7716 |
| 5 | -.6333 | -.6334 | -.6334 | -.6334 | .0016 | 8.5239 | .1447 |
| 6 | .1086 | -.6766 | -.6766 | -.6766 | -.6766 | .1086 | 7.9905 |

TIMES (REPEATED MEASUREMENTS)

| TRUE P | | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| IV | 1 | 0 | 1 | 0 | 0 | 0 | 0 | 0 | 1 | 1 | 0 | 0 | 0 | 0 | 0 | 0 | 1 | 0 | 0 | 0 | 0 |
| DV | 2 | 0 | 1 | 0 | 0 | 0 | 0 | 0 | 1 | 1 | 0 | 0 | 0 | 0 | 0 | 0 | 1 | 1 | 0 | 0 | 0 |
| DV | 3 | 0 | 1 | 1 | 1 | 0 | 0 | 0 | 1 | 1 | 1 | 1 | 0 | 0 | 0 | 0 | 1 | 1 | 1 | 0 | 0 |
| DV | 4 | 0 | 1 | 1 | 1 | 0 | 0 | 0 | 1 | 1 | 1 | 1 | 1 | 0 | 0 | 0 | 1 | 1 | 1 | 1 | 0 |
| DV | 5 | 0 | 1 | 1 | 1 | 1 | 1 | 0 | 1 | 1 | 1 | 1 | 1 | 1 | 0 | 0 | 1 | 1 | 1 | 1 | 1 |

1002

TEMPORAL INTERACTION

| TRUE PERSISTENCE | 1 | 2 | 3 | 4 | 5 |
|---|---|---|---|---|---|
| 1 | 11.4522 | 5.3613 | 2.9155 | 1.6119 | .7852 |
| 2 | 5.3613 | 11.2837 | 6.0478 | 3.2935 | 1.6118 |
| 3 | 2.9155 | 6.0478 | 11.1459 | 6.0478 | 2.9155 |
| 4 | 1.6112 | 3.2938 | 6.0478 | 11.2837 | 5.3613 |
| 5 | .7852 | 1.6118 | 2.9155 | 5.3613 | 11.4522 |

FIG. 10

MOCK DATA

1100

TIMES

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| IV | 1 | 1 | 0 | 0 | 0 | 0 | 0 | 1 | 1 | 0 | 0 | 0 | 0 | 0 | 0 | 1 | 0 | 0 | 0 | 0 |
| DV | - | 0 | 1 | 1 | 1 | 0 | 0 | 0 | 1 | 1 | 1 | 1 | 0 | 0 | 0 | 0 | 1 | 1 | 1 | 0 |

RESULTS

1102

| Persistence | DELAY | | | | | | |
|---|---|---|---|---|---|---|---|
| | 0 | 1 | 2 | 3 | 4 | 5 | 6 |
| 1 | -1.7711 | 2.3630 | 2.1532 | 2.4202 | -1.7317 | -1.5148 | -1.0983 |
| 2 | .0490 | 5.4949 | 5.0498 | .0231 | -4.1548 | -2.8106 | -.4111 |
| 3 | 1.7284 | 10.5663 | 1.1099 | -.8077 | -6.8801 | -1.9925 | .1204 |
| 4 | 6.1035 | 5.5911 | 0 | -2.7411 | -6.8682 | -.2188 | 1.6197 |
| 5 | 3.1396 | 2.6444 | -.7429 | -3.3863 | -3.9192 | .3035 | 2.3682 |

FIG. 11

DATA

1200

TIMES (REPEATED MEASUREMENTS)

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| IV-1 | 0 | 1 | 1 | 1 | 0 | 1 | 1 | 0 | 0 | 1 | 1 | 1 | 0 | 1 | 1 | 1 | 1 | 0 | 1 | 1 |
| IV-2 | 0 | 1 | 1 | 0 | 0 | 1 | 0 | 1 | 0 | 1 | 1 | 0 | 1 | 1 | 0 | 1 | 0 | 1 | 1 | 1 |
| AND | 0 | 1 | 1 | 0 | 0 | 1 | 0 | 0 | 0 | 1 | 1 | 0 | 0 | 1 | 0 | 1 | 0 | 0 | 1 | 1 |
| DV | 0 | 1 | 1 | 0 | 0 | 1 | 0 | 0 | 0 | 1 | 1 | 0 | 0 | 1 | 0 | 1 | 0 | 0 | 1 | 1 |

BENEFIT-AND-HARM SCORE RESULTS

1202

| CONDITION | HARM SCORE |
|---|---|
| Drug 1 Alone | -3.969 |
| Drug 2 Alone | -4.962 |
| Drug 1 AND Drug 2 | -11.159 |

FIG. 12

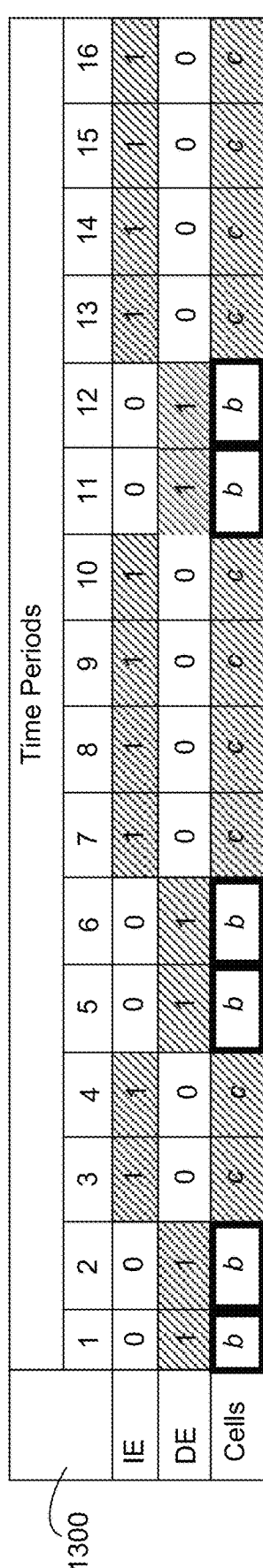
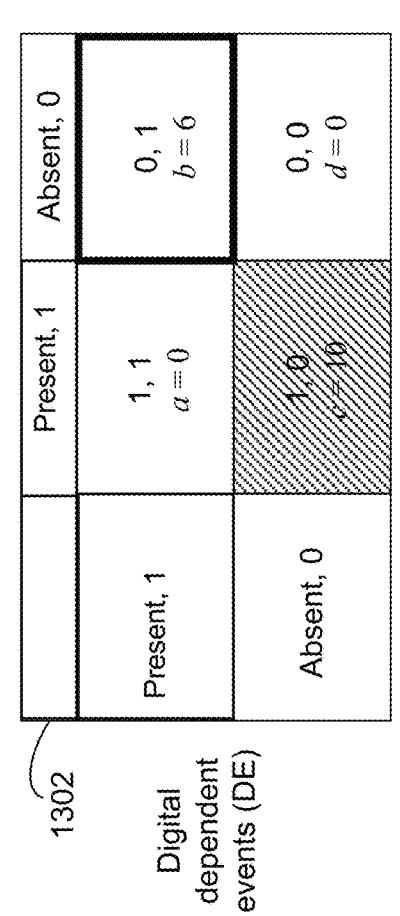
FIG. 13

1400

$$|B\&H| = \frac{n(ad - bc)^2}{(a + b)(c + d)(a + c)(b + d)} = 16.00$$

$$E(a) = \frac{(a + b)(a + c)}{n} = 3.75$$

STANDARDIZATION

| Column 1. All possible 2 x 2 tables | Column 2. $B\&H_{raw}$ | Column 3. Probabilities | Column 4. B&H Score |
|---|---|---|---|
| 0  6<br>10  0 | 16.00 | .000124875 | 8.92 |
| 1  5<br>9  1 | 8.60 | .00749251 | 4.79 |
| 2  4<br>8  2 | 3.48 | .0842907 | 1.93 |
| 3  3<br>7  3 | .64 | .299700 | .34 |
| 4  2<br>6  4 | -.07 | .393357 | -.06 |
| 5  1<br>5  5 | -1.78 | .188811 | -1.01 |
| 6  0<br>4  6 | - 5.76 | .0262238 | -3.24 |

$$B\&H_{raw} = \frac{(a+b)!(c+d)!(a+c)!(b+d)!}{n!a!b!c!d!}$$

1) Compute the expected value of the discrete probability distribution of $B\&H_{raw}$ $E(B\&H_{raw}) = \sum(B\&H_{raw})\, P\,(B\&H_{raw}) = -0.037$ 2) Compute the variance of this distribution $\sigma^2 = \sum[B\&H_{raw} - E(B\&H_{raw})]^2\, P(B\&H_{raw}) = 3.200$ 3) Use these to compute the discrete probability distribution of standardized $B\&H_{raw}$ scores with this formula $$B\&H_{raw} = \frac{B\&H_{raw} - E(B\&H_{raw})}{\sigma}$$

FIG. 17

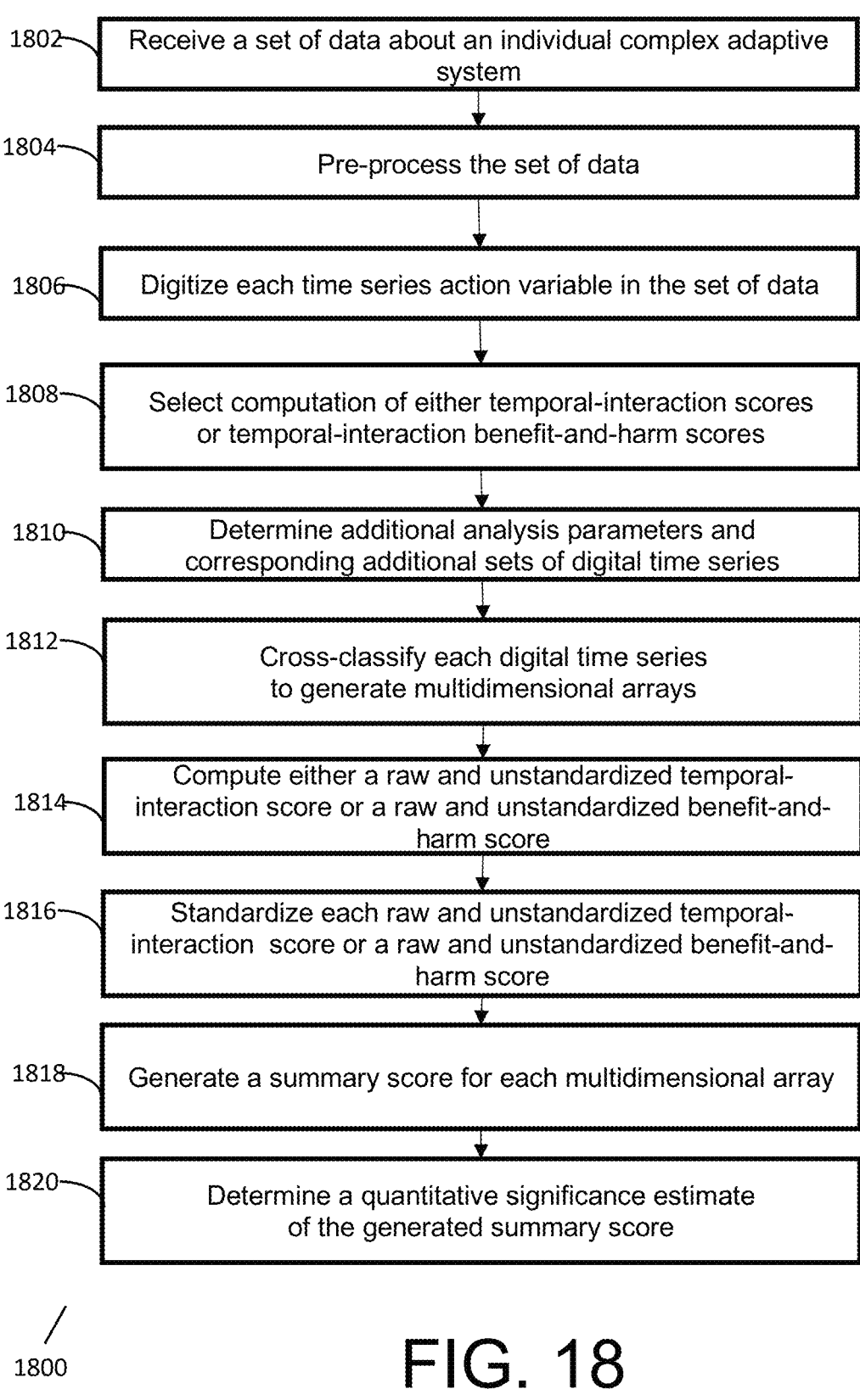

1802 — Receive a set of data about an individual complex adaptive system

1804 — Pre-process the set of data

1806 — Digitize each time series action variable in the set of data

1808 — Select computation of either temporal-interaction scores or temporal-interaction benefit-and-harm scores 1810 — Determine additional analysis parameters and corresponding additional sets of digital time series 1812 — Cross-classify each digital time series to generate multidimensional arrays 1814 — Compute either a raw and unstandardized temporal-interaction score or a raw and unstandardized benefit-and-harm score 1816 — Standardize each raw and unstandardized temporal-interaction  score or a raw and unstandardized benefit-and-harm score 1818 — Generate a summary score for each multidimensional array 1820 — Determine a quantitative significance estimate of the generated summary score

QUANTIFYING EVIDENCE FOR REGULATORY CONTROL AND MECHANISMS WITH COMPLEX ADAPTIVE SYSTEMS METROLOGY BY COMPUTATION METHODS AND SYSTEMS

CROSS-REFERENCE TO RELATED APPLICATION

This application is a continuation of U.S. patent application Ser. No. 18/428,980, filed Jan. 31, 2024, which claims the priority benefit of U.S. patent application Ser. No. 18/085,278 filed Dec. 20, 2022, now U.S. Pat. No. 11,935, 659, which claims the priority benefit of U.S. patent application Ser. No. 17/551,110 filed Dec. 14, 2021, now U.S. Pat. No. 11,538,592 issued Dec. 27, 2022, which claims the priority benefit of U.S. Provisional Application No. 63/125, 507, filed on Dec. 15, 2020, the disclosures of which are herein incorporated by reference in their entireties.

TECHNICAL FIELD

This disclosure is directed to measurement of how complex adaptive systems work.

BACKGROUND

Conventional mathematical and statistical theories, laws, and models have contributed mightily to the advancement of physical sciences. For example, SI units of measurement help make complicated systems such as fighter aircraft and spacecraft reliable, predictable, trustworthy, and valuable. However, when it comes to quantifying how complex adaptive systems work in the time dimension, there remains a largely unmet need for software-based complex adaptive systems metrology-by-computation techniques.

SUMMARY

The computational methods and systems for measuring how individual Complex Adaptive Systems (CAS) work in the time dimension described herein are distinct from and supplement physical science methods and systems. Physical science methods and systems include software and algorithms directed to the International System of Units (SI), mathematics, and statistics. Physical science methods and systems have been highly successful, for example, in targeting spacecraft to planets, moons, and asteroids. In contrast, physical science methods have been far less successful, also by example, in targeting the right drug to the right person at the right safe and effective dose for drug development and medicine. The difference is that living persons and brains are CAS in addition to being physical entities. Being CAS slows and limits progress and productivity achievable with physical science methods and systems. Complex Adaptive Systems Metrology (CASM) represents an additional category of derived or computed measurement units. CASM, disclosed herein, offers to help close the progress and productivity gap exemplified by these two targeting examples. Measurement helps.

CASM methods and systems apply to multivariate time series data about individual CAS and their environments. CASM computes multidimensional arrays of universally and mathematically standardized, bi-directional, temporal-interaction scores and their CASM quantitative significance estimates. Zero-value temporal-interaction scores indicate no evidence for temporal interactivity between two or more time-series action variables. Using the terminology of network graphs, CASM quantifies evidence for edges for time-series action-variable nodes. Temporal-interaction scores for description and prediction quantify how individual CAS, including persons, work—and the temporal mechanisms of work—in the time dimension. CASM defines work as being comprised of how individual CAS (a) function internally as to improve diagnoses of chronic disorders, (b) respond to their environments including treatments as to improve drug evaluation, and (c) act as agents on their environments. Temporal-interaction scores computed with CASM are, in turn, suitable output for mathematical modeling, descriptive and inferential statistics when there is a plurality of CAS, and artificial intelligence techniques.

In one general aspect, a computer-implemented complex adaptive systems metrology (CASM) method is described for generating universally and mathematically standardized scores that quantify longitudinal evidence for either temporal-interaction scores or temporal-interaction benefit-and-harm scores. The method may include receiving a set of data about an individual complex adaptive system where the set of data includes multivariate time-series action variables representing the individual complex adaptive system. The method may further include pre-processing the set of data, the pre-processing including decomposing time series to distinguish evidence for temporal interactions from linear and nonlinear trends. The method may further include digitizing each time series action variable in the set of data that has more than two levels to a set of digital time series comprised of zeros and ones to generate analysis parameters, where the analysis parameters include at least an independent action variable level for one or more independent action variables associated with at least a portion of the set of data, and a dependent action variable level for one or more dependent action variables associated with at least a portion of the set of data. The method may further include selecting computation of either temporal-interaction scores or temporal-interaction benefit-and-harm scores.

The method may further include determining additional analysis parameters by generating a plurality of additional sets of digital time series where the generating including applying operationally defined rules to the digitized set of digital time series for the one or more independent action variables or the digitized set of digital time series for the one or more dependent action variables. The method may further include cross-classifying each digital time series for a respective independent action variable or a set of the one or more independent action variables with each digital time series for a time series for a respective dependent action variable or a set of the one or more dependent action variables, the cross-classifying comprising generating one or more multidimensional arrays of tables, each array having at least one dimension for each of the analysis parameters or the additional analysis parameters and at least one array for any Boolean independent events, any Boolean dependent events, and any combination of Boolean independent events and Boolean dependent events. The method may further include computing, for each of the tables, either a raw and unstandardized temporal-interaction score or a raw and unstandardized benefit-and-harm score and standardizing each raw and unstandardized temporal-interaction score or each benefit-and-harm score so that each standardized score represents one score from a distribution of potential scores defined by the set of data in combination with a CASM scoring protocol, where said distribution of potential scores having a mean of 0 and a standard deviation of 1 unless 0 is the only potential score. The method may further include generating a summary score for each multidimensional array, the summary score being based on either the standardized temporal-interaction scores or the standardized temporal-interaction benefit-and-harm scores and determining, based on the generated summary score for each multidimensional array, a quantitative significance estimate of the generated summary score for either the standardized temporal-interaction scores or the standardized temporal-interaction benefit-and-harm scores.

Implementations can include any or all of the following features. In some embodiments, the set of data further includes time-series information about components or aspects corresponding to an environment associated with the set of data and selecting the computation of either temporal-interaction scores or temporal-interaction benefit-and-harm scores is based on at least one study associated with the set of data.

In some embodiments, the set of data includes one or more of at least two repeated measurements of each of at least two time-series action variables, at least one time-series action variable operating as an independent variable, and at least one time-series action variable operating as a dependent variable.

In some embodiments, the pre-processing further includes computing linear regression residuals to remove linear trends that are long term compared to a temporal resolution or frequency of repeated measurements of the time-series data, computing polynomial regression residuals of different orders to remove non-linear trends that are long term compared to the temporal resolution of the time-series data, and computing successive differences to assess effects of changes as distinct from effects of absolute levels.

In some embodiments, the temporal-interaction benefit-and-harm scores specify a favorable response or an unfavorable response of higher magnitude levels of each of the one or more dependent action variables, and specify a relative importance weight of each of the one or more dependent action variables.

In some embodiments, the plurality of additional sets of digital time series account for one or more of an independent action variable episode length analysis parameter, an independent action variable episode criterion analysis parameter, a dependent action variable episode length analysis parameter, a dependent action variable episode criterion analysis parameter, an independent action variable delay of effect analysis parameter, an independent action variable effect persistence analysis parameter, Boolean predictor action variable events, and Boolean predicted action variable events.

In some embodiments, the plurality of tables includes one or more multidimensional arrays of 2×2 tables and the plurality of events account for a type of Boolean event with each 2×2 table comprising a number of times there were (1,1); (0,1); (1,0); and (0,0) events. In some embodiments, wherein the raw and unstandardized temporal-interaction score or the raw and unstandardized benefit-and-harm score is calculated for each 2×2 table.

In some embodiments, wherein standardizing includes obtaining marginal frequencies of each 2×2 table to identify all possible 2×2 tables given the marginal frequencies of the 2×2 table and computing a raw or unstandardized temporal-interaction score or each raw or unstandardized temporal-interaction benefit-and-harm score for each possible 2×2 table. The computing a hypergeometric probability of obtaining each possible raw or unstandardized temporal-interaction score or each raw or unstandardized temporal-interaction benefit-and-harm score by random chance, computing a mean and standard deviation of a distribution of potential scores from the raw or unstandardized scores together with each of the respective hypergeometric probabilities, and using the mean and standard deviation of the distribution of potential scores to determine the standardized temporal-interaction or standardized temporal-interaction benefit-and-harm score corresponding to each 2×2 table.

In some embodiments, generating the summary score further includes repeating, for arrays corresponding to Boolean events: identifying a most extreme magnitude score, positive or negative, to summarize each multidimensional array with any positive and negative scores with equal magnitudes but opposite signs being summarized as 0, summarizing evidence for either temporal-interaction or temporal-interaction benefit and harm as functions of each the analysis parameters or the additional analysis parameters, and summarizing evidence for either temporal-interaction or temporal-interaction benefit and harm as functions of any combination of each of the analysis parameters or the additional analysis parameters.

In some embodiments, determining the quantitative significance estimate of the generated summary score includes randomly permuting a temporal order of one or more of the time series from which the temporal-interaction summary score or temporal-interaction benefit-and-harm score was determined, determining a summary score by applying the method of claim 1 to the permuted data to obtain a permuted data temporal-interaction score or temporal-interaction benefit-and-harm score summary score, repeating the two previous steps a plurality of cycles to generate a probability distribution of temporal-interaction summary scores or temporal-interaction benefit-and-harm scores from permuted data with one summary score for each permuted order, and relating the temporal-interaction summary score or summary temporal-interaction benefit-and-harm score to the probability distribution of permuted data temporal-interaction summary scores.

In some embodiments, the relating includes one or more of determining a CASM quantitative significance using a two-tailed test including a positive tail and a negative tail, by determining a proportion of permuted data summary scores equal to or greater than an absolute value of the summary temporal-interaction score or the summary temporal-interaction benefit-and-harm score, determining a CASM quantitative significance of a one-tailed test for the negative tail by determining a proportion of negative permuted order temporal-interaction summary scores equal to or greater in magnitude than the temporal-interaction summary score or the temporal-interaction benefit-and-harm score, determining a CASM quantitative significance of a one-tailed test for the positive tail by determining a proportion of positive permuted order temporal-interaction summary scores or summary temporal-interaction benefit-and-harm scores equal to or greater in magnitude than the temporal-interaction summary score or the temporal-interaction benefit-and-harm score.

In some embodiments, the complex adaptive systems metrology (CASM) is configured for use with second-generation evidence-based medicine (EBM-2G) randomized controlled trial (RCT) designs including EBM-2G single-person RCT designs. In some embodiments, the single-person RCT design is configured for a single person, a single group including a plurality of single persons, or multiple groups including a plurality of single groups that include a plurality of single persons.

In some embodiments, the complex adaptive systems metrology (CASM) is configured for use with effects monitoring of individual patients. In some embodiments, the effects monitoring includes one or more of second-generation EBM-2G health-effects monitoring, treatment, and environmental effects monitoring. In some embodiments, the complex adaptive systems metrology (CASM) is configured to determine outcomes for at least one of drug effects monitoring, diet effects monitoring, exercise effects monitoring, allergen effects monitoring, and pollution effects monitoring.

In some embodiments, the complex adaptive systems metrology (CASM) is configured to determine outcomes for at least one of second-generation evidence-based medicine (EBM-2G) temporal-interaction phenotype tests, EBM-2G diagnostic temporal-interaction phenotype tests, EBM-2G treatment response temporal-interaction phenotype tests, EBM-2G environmental response temporal-interaction phenotype tests, EBM-2G agency temporal-interaction phenotype tests, EBM-2G agency-on-self-care temporal-interaction phenotype tests, and EBM-2G agency-on-others-and-one's-environment temporal-interaction phenotype tests.

Implementations can be performed on a complex adaptive systems metrology system by one or more processors including one or more computer-readable mediums. The systems and aspects above may be configured to perform any combination of the above-described aspects, each of which may be implemented together with any suitable combination of the above-listed features and aspects.

Implementations of the described techniques may include hardware, a method or process, or computer software on a computer-accessible medium. The details of one or more implementations are set forth in the accompanying drawings and the description below. Other features will be apparent from the description and drawings, and from the claims.

BRIEF DESCRIPTION OF THE DRAWINGS

FIG. 5 is a table illustrating example results from a simulation that shows how using larger numbers of repeated measurements of time-series action variables offer to increase statistical significance when benefit-and-harm scores are computed from data with larger numbers of repeated measurements.

FIG. 6 is a table illustrating example digitization at an ordinal level of measurement for two different time series, dose, and response variable level.

FIG. 7 is a table illustrating an example of how an embodiment of a CASM platform is configured to study up to 36 combinations of episode length and episode criterion for episodes of independent events and dependent events.

FIG. 8 is a table illustrating an example of how a CASM platform detects and quantifies evidence for delay of response.

FIG. 9 is a table illustrating an example of how a CASM platform correctly identifies and quantifies the response delays of FIG. 8.

FIG. 10 is a table illustrating an example of how a CASM platform correctly identifies and quantifies evidence for effect persistence (P).

FIG. 11 is a table illustrating example mock data to demonstrate how users of a CASM platform obtain correct results investigating delay of response and response persistence simultaneously.

FIG. 12 is a table illustrating example mock data and benefit-and-harm scores for two distinct types of drugs that appear to interact to increase occurrences of an adverse event defined on a dependent variable.

FIG. 13 is a table illustrating an example of generating a 2×2 table using the two digital time series identified by circles in FIG. 6.

FIG. 14 is an example process including a set of equations and determinations for computation of a raw temporal-interaction benefit-and-harm score using a 2×2 table.

FIG. 15 is an example table illustrating mathematical standardization of a raw temporal-interaction benefit-and-harm score.

FIG. 16 is the equation for determining hypergeometric probabilities re-purposed for a CASM platform.

FIG. 17 is an example process for generating universal standardization of temporal-interaction scores.

FIG. 18 is a flow diagram illustrating a method for using Complex Adaptive Systems Metrology (CASM) to generate scores and significance estimates for evaluative studies.

Figure 1A:
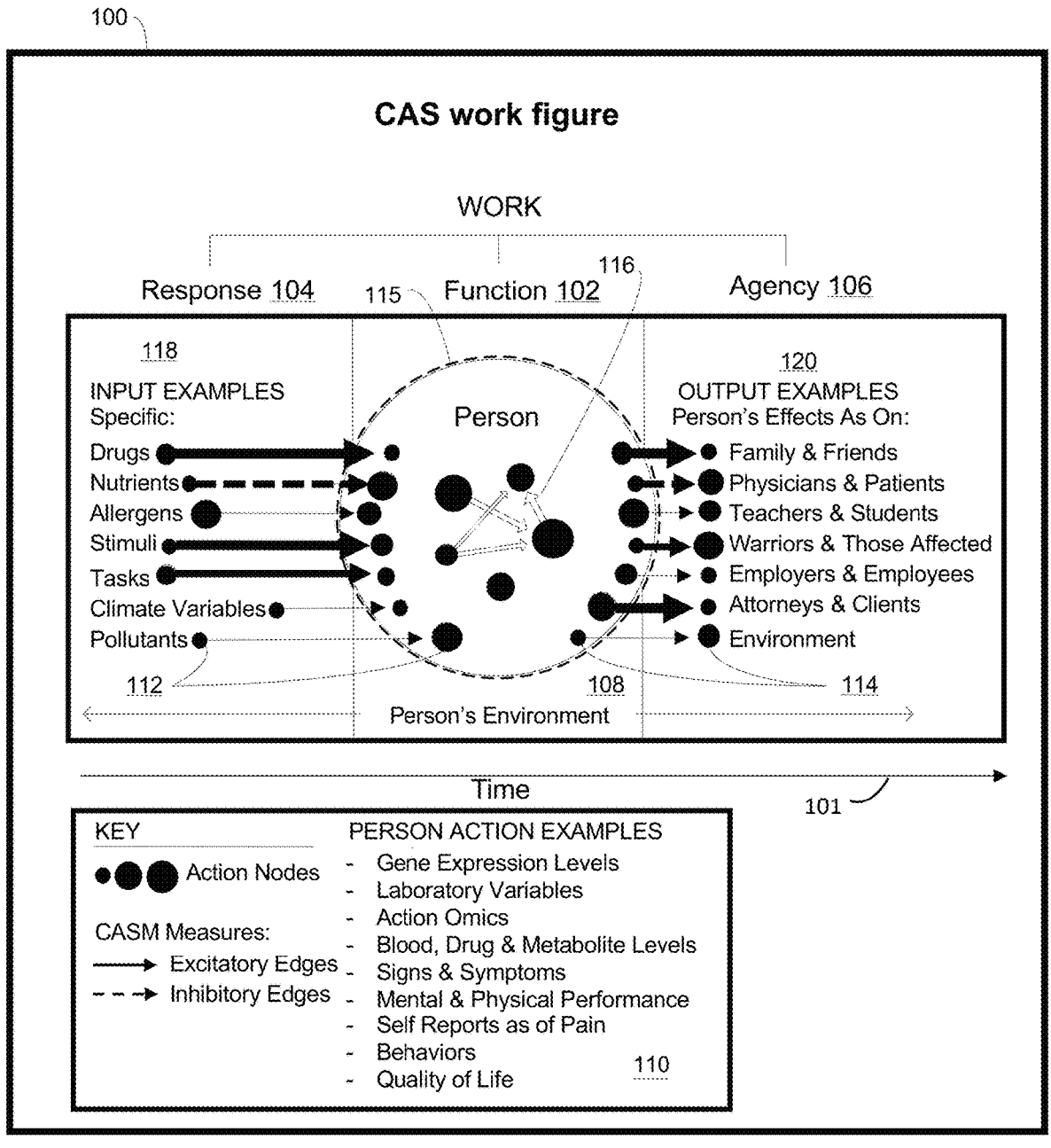
FIG. 1A is a block diagram illustrating an operational definition for Complex Adaptive Systems (CAS) work in the time dimension as quantified with temporal-interaction scores for use with embodiments described herein.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but to enable any person skilled in the art to make and use the described subject matter. Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

1. Introduction

Mathematical and statistical theories, laws, and models based on SI units of measurement, such as set forth by the National Institute of Standards and Technology (NIST) of the United States Department of Commerce, have contributed mightily to the advancement of physical sciences and engineering as exemplified by the precision required for spacecraft to land on planets, moons, and asteroids.

Additionally, the SI units of measurement, together with mathematics and statistics, are conventionally used to attempt to quantify the workings and mechanisms of living Complex Adaptive Systems (CAS). However, such conventional metrics are not enough to generate and define precise basic and applied quantitative knowledge of CAS. More specifically and by example, the SI units of measurement, together with mathematics and statistics may not adequately quantify outcomes and metrics in the fields of drug discovery, drug development, and human medicine. There remains a need for complex adaptive systems metrology by computation embodied by a complex adaptive systems metrology platform. For brevity, this disclosure refers to "the specified software-based complex adaptive systems metrology-by-computation methods, systems, computed tests, and treatment targets software platform" as the "CASM platform" with CASM standing for Complex Adaptive Systems Metrology.

The CASM platform described herein may be configured to process, assess, and summarize Multivariate Time Series (MTS) data from sensors, monitors, dispensers, electronic devices, and/or medical devices, and the like, to improve understanding, the safety and effectiveness of drug-based medicine, and the capabilities of electronic devices, and/or medical devices. Such processing, assessing, and summarization of such data may provide improvements to the fields of drug discovery, drug development and approval by taking into account additional aspects of such data with respect to individualized medicine for each individual patient.

The CASM platform described herein may be configured to analyze CAS to assess whether particular drugs, treatments, and/or protocols will be safe and effective for a particular individual. That is, unlike conventional physical sciences based on applying mathematics and statistics, the CASM platform may employ ultra-digital CASM techniques to MTS data (e.g., to functional brain imaging MTS data) to extend the capabilities of conventional mathematics and statistics by quantifying (a) evidence for complex adaptive systematicity and (b) evidence for temporal interactivity in the presence of complex adaptive systematicity. Personhood is a manifestation of complex adaptive systematicity. Patient centricity demands accounting for personhood in addition to physicality. The systems and methods described herein can process MTS data sets to determine whether particular drugs, treatments, and/or protocols based on specific patient data improve outcomes.

The systems and methods described herein may identify applications of the CASM platform to expedite scientifically rigorous and cost-effective treatments with improved outcomes as compared with conventional Evidence-Based Medicine (EBM). The CASM platform may provide reliable and valid measures about how individual patients and other persons function internally as for medical diagnosis, how individual patients and other persons respond to their environments, including treatments, and how individual persons act as agents regarding their own health and the health and well-being of others.

For example, the CASM platform may improve the discovery and development of approved drugs and medicine for chronic disorders (for particular patients) because the CASM platform may analyze, assess, and compute new measures in an improved manner over conventional mathematics and statistics. Compared to acute disorders and trauma, chronic disorders are intensively time-dependent and evidence for chronic disorders and treatment response abound in MTS data. Improved quantification, such as how living brains and/or bodies work in the time dimension, may help enable differential mechanism-specific diagnoses, better targeting during drug discovery, drug development, and pharmacotherapy as well as disease prevention. The CASM platform described herein provides such an improved quantification and does so on a per patient basis.

In general, the CASM platform may be configured to process MTS data (i.e., two or more repeated measurements of two or more time-dependent action variables) about an individual CAS, its environment, and its treatment. MTS (e.g., data movies) can provide orders of magnitude more information for knowing CAS than cross-sectional data and change scores (e.g., data snapshots). This MTS information advantage comes from more repeated measurements to help separate signals from noise, plus the repeated measures being in temporal order. Because timing is a common measurement across all living things, assessing the MTS data with a time component improves the resulting accuracy of the output of analyzing such data.

In addition, the CASM platform employs techniques that are ultra-digital, meaning that each dimensional or analog action variable time series is transformed into an ordered set of digital or binary series (0s and 1s), without having to lose information, before further processing. The ultra-digitality of the CASM platform ensures that less information is left out of the end results. That is, the CASM platform can use orders of magnitude more information in MTS data than conventional statistical processing and generates datasets orders of magnitude bigger and more informative than the data that the CASM platform processed as compared to other conventional methods for processing MTS data. For example, functional brain imaging data is generally large. The CASM platform increases the data upon completion of analysis in comparison to other conventional methods for processing MTS data. The CASM platform applies to multivariate time series data. The CASM platform described herein may be configured to compute universally standardized scores that quantify multiparametric patterns of evidence for temporal interactions between and among two or more action variables explicitly in the time dimension. Universal standardization may be achieved mathematically by computation. As used herein, the resulting universally standardized unit of measurement is defined as a "bagne." The bagne is a universally standardized measure of the amount of evidence for interaction over time between two or more action variables. Universal may refer to how the computational process applies to action variables about any activity that can be measured repeatedly and CAS of any type. Universal is not about consensual acceptance as of scientific paradigms.

As used herein, the term "action variable" refers to either discrete events that can be either present or absent during a series of discrete periods of time or dimensional variables with more than two levels that can vary or fluctuate, for which levels or doses can be randomized longitudinally in the time dimension.

The multivariate time series data to which the hereby-specified CASM platform applies are repeated measurements data and include streaming data. Repeated measurements data are more informative for assessing temporal phenomena such as delay of effect, effect persistence, and empirical evidence for causality when repeated measurements are equally spaced in time. This disclosure identifies such data as multivariate time series data.

As used herein, Multivariate Time Series (MTS) data is hereby broadly defined as two or more repeated measurements of two or more time-series action variables. A temporal resolution of multivariate time series (e.g., fractions of a second, seconds, minutes, hours, days, weeks, months, years, decades) can be selected in accordance with the pace of the temporal dynamics being studied. The CASM platform is configured to process a rapidly growing deluge of MTS data as from business, economics, medicine, and environmental monitoring into knowledge and value.

The CASM platform utilizes at least two action variable time series to quantify evidence for temporal interactions or temporal interactivity. Users of the CASM platform can set how action variables operate. At least one time series operates as an independent action variable, and at least one time series operates as a dependent action variable. More generally, independent action variables can be time series operating as predictors, exposure variables, explanatory variables, causal variables, effectors, stimuli, and inputs. For brevity, this disclosure uses the term "independent action variable" to include all terms for time series operating in this or a similar capacity. Likewise, dependent action variables can be response variables, predicted variables, explained variables, receptor variables, effect variables, outcome variables, and outputs. Again, for brevity, the term "dependent action variable" indicates all terms for time series operating in this or a similar capacity.

Temporal-interaction scores computed by applying the CASM platform are mathematically standardized. Each temporal-interaction score is one score from a distribution of potential scores having a mean of 0 and a standard deviation of 1 (unless 0 is the only possible score). For example, the only possible score is 0 when there is no temporal variation in either the independent variable, the dependent variable, or both. Each distribution of potential scores is entirely, operationally, and transparently defined by the data that are being processed by the CASM platform combined with a CASM scoring protocol applied to the data and defined by selecting or applying data processing options as from CASM platform menus.

Temporal-interaction benefit-and-harm scores, sometimes shortened for brevity to the term "benefit-and-harm scores," are a variation and subset of temporal-interaction scores. Evidence for benefit and harm, according to this disclosure, is not quantified cross-sectionally at a point in time. This disclosure involves quantifying evidence longitudinally in the time dimension. Many clinical trials can use benefit-and-harm scores for evaluative studies.

Temporal-interaction benefit-and-harm scores are related to temporal-interaction scores as follows. Temporal-interaction scores are positive when higher levels of an independent action variable time series are associated temporally with higher levels of a dependent action variable time series. Conversely, temporal-interaction scores are negative when higher levels of an independent action variable time series are associated temporally with lower levels of a dependent action variable time series.

However, higher levels of dependent action variables for evaluative studies such as clinical trials can be either toward and positive or untoward and negative. For example, both higher levels of high-density lipoprotein (good) cholesterol and lower levels of low-density lipoprotein (bad) cholesterol on higher drug doses can be beneficial. Accordingly, users of the CASM platform can identify whether higher levels of a dependent or response variable time series are toward or untoward according to clinical significance, patient preferences, and social impact. The CASM platform then reverses the signs of temporal-interaction scores as may be necessary to create temporal-interaction benefit-and-harm scores for which all beneficial effects have positive scores. All the harmful effects will have negative scores. Clinical significance can be set as from epidemiologic studies as about how levels of various lipid-fraction action variables affect rates of heart attack, stroke, and death. Additionally, dependent or response variable specific benefit and harm scores can be differentially weighted in accord with clinical significance, patient preferences, and social impact to compute patient-specific overall benefit-and-harm scores.

Temporal-interaction benefit-and-harm scores can be used as a 'common metric' to evaluate drugs' safety and effectiveness for preventing and managing chronic disorders as for drug development and evidence-based medicine.

In general, the CASM platform may compute temporal-interaction (TI) scores that quantify facts of nature. Benefit-and-harm scores are a subset to TI scores for evaluative studies, including randomized controlled trials (RCTs). The difference is in how one values facts of nature quantified with TI scores. For example, TI scores can be used quantify how drug dose, an action variable, affects some laboratory measure (also an action variable). Positive TI scores would be higher with higher. Negative TI scores would be higher with lower. In contrast, benefit-and-harm scores also account for the positive or toward and negative or untoward directionality of the response action variables. Evaluative studies, as used herein may account for how facts of nature are valued by persons, accounting for things like patient preferences and clinical significance, as in predicting death. The CASM platform may assess quantitative significance, which is about estimating the probability of obtaining a summary TI score by chance given an individual's data, a CASM scoring protocol, and the null hypothesis of no temporal interaction. In contrast, statistical significance is about going from samples of individuals to populations.

In general, living systems exemplify CAS. Many examples in this disclosure are about living CAS and their living component systems such as cells, organs, organ systems, and brains. This disclosure focuses on persons and medicine. The principles and capabilities described herein also apply to other types of living systems as well as non-living CAS, as described above.

Applications of the CASM platform include evaluating drug safety and effectiveness for individual patients, including the CASM quantitative significance of benefit-and-harm scores for individual patients. For example, using the CASM platform to generate quantitative significance estimates for health effects monitoring of liver enzymes and drug levels for an individual patient could provide compelling evidence that that the patient is at high risk of losing their liver despite drug approval being based on conventional Group Average Science (GAS) or legacy RCTs with thousands of patients.

In some embodiments, the CASM platform can be a powerful tool for drug purposing and repurposing. For example, conventional examples of drug repurposing occurred when cardiovascular drugs were found to grow hair and bolster erections-new and unexpected indications with great value. With the CASM platform, drug developers may perform drug targeting by monitoring as many response variables as possible, starting with the first patient on a particular drug. Resulting benefit-and-harm scores may then be used to target the particular drug to patients most apt to benefit and away from patients apt to be harmed. In this way, drug targeting could be based on cumulative bodies of clinical evidence starting with the first person on drug. In contrast, conventional GAS RCT evaluate drugs in batch mode. Conventional RCTs that focus on efficacy neglect safety often leading to excess morbidity, mortality, ethical liability, legal liability, and lost opportunity costs for patients, pharmaceutical companies, and investors alike.

Drugs and other treatments typically have multiple effects, beneficial and toward as well as harmful and untoward. This multiplicity is a manifestation of complexity. Nevertheless, conventional RCT designs typically test primary hypotheses based on primary response variables for efficacy. Accordingly, such RCT designs offer partial and typically incomplete scientific evaluations of safety and effectiveness. Drug safety typically is evaluated with lower standards of scientific rigor than efficacy. Drug labels report safety and efficacy information in different sections of drug labels. Clinicians, patients, and other stakeholders are left to integrate and balance rates of adverse events together with group average evidence for efficacy. Clinicians and other decision-makers are left to integrate and balance such limited, complicated, and divided evidence and apply the results to individual patients. Subjective impressions prevail over scientific evidence. In contrast, temporal-interaction scores computed with the CASM platform include universally standardized benefit-and-harm scores as a common metric as to evaluate person-specific drug safety and effectiveness across two or more response action variables. Conventionally, drugs are developed, approved, or not approved, for marketing by regulatory agencies, prescribed, paid for, and consumed without applying a common metric of benefit and harm to quantify evidence for drug safety and effectiveness regarding dependent or response action variables. Lack of integrated measures of drug safety and effectiveness are a problem because decision-makers can select drugs and drug doses. Decision-makers do not select drug effects. Drug effects are facts of nature.

Persons and brains epitomize CAS. Thus, medical (e.g., medicine-based) applications may benefit from the application of the specified CASM platform. As examples, medicine may benefit from measuring temporal order and disorder to improve diagnoses of chronic disorders, measuring the safety and effectiveness of drugs used to prevent and manage chronic disorders, and accounting scientifically for the complex adaptive systematicity of personhood.

2. Applications for Medicine and Drug Development

As used herein, the term "second-generation evidence-based medicine" (EBM-2G) refers to identifying applications of the specified CASM platform to expedite scientifically rigorous, truthful, and cost-effective treatments with improved outcomes as compared to conventional Evidence-Based Medicine (EBM). Being truthful and having high scientific veracity refer to accounting scientifically for living systems being CAS in addition to being physical entities. Compared to EBM, EBM-2G is based on reliable and valid measures about how individual patients and other persons function internally as for medical diagnosis, how individual patients and other persons respond to their environments, including treatments, and how individual persons act as agents regarding their own health and the health and well-being of others. EBM-2G also applies to drug development.

Conventional EBM is mainly based on cross-sectional data and evidence. In contrast, EBM-2G is more longitudinal and temporal. EBM-2G may be used to build upon genomic data via improved genotype-phenotype mapping. Genomic data is often used to identify and differentiate persons and cancers and may be inherently static and cross-sectional. EBM-2G gains precision compared to precision medicine by adding reliable and valid temporal-interaction scores, computed from multivariate time series data. Temporal-interaction scores quantify how persons and other CAS work in the time dimension. Quantifying work includes EBM-2G RCT designs (Section 7); health-effects monitoring for EBM-2G (Section 8); and EBM-2G quantitative temporal-interaction phenotypes and phenotype tests (Section 9) for improved diagnosis, improved treatment evaluation, and scientific assessments of agency.

EBM is generally tightly linked to parallel-group RCT designs that assess evidence for causality by comparing groups using statistical measures of group central tendency and dispersion. Clinical trials and other studies, which use descriptive and inferential statistics to assess causality with samples of individuals from populations, are examples of group-average science (GAS). The specified CASM platform enables additional and often improved RCT designs when both independent (treatment) and dependent (response) can be quantified with time-dependent action variables as distinct from categorical variables and endpoints.

GAS RCT designs have limitations and deficiencies regarding the provision of the best evidence in decision-making with respect to the care of individual patients as when drugs are developed, approved, prescribed, paid for, and consumed to prevent and manage complex chronic disorders and diseases. Instead, a GAS RCT design generally provides group-average results across many subjects, which leads to the pervasive one-size does-not-fit-all problem. Furthermore, GAS results are limited mainly to a primary endpoint. GAS RCTs do not provide reliable and valid multiparametric evaluations and profiles of safety and effectiveness of treatment for individual patients who have or are subject to chronic disorders.

Advancing from EBM to EBM-2G will make use of a measure of adaptivity. For example, the specified CASM platform would empower statisticians with a new category of measures to model, analyze, and use to make inferences from samples of individuals to populations when there are two or more individuals in the same category. The specified CASM platform offers advantages to empower statisticians seeking to identify genetic and other predictors of disease susceptibility and treatment response.

The pharmaceutical industry and its regulators often use GAS RCT designs with subjects cross-sectionally randomized to groups defined by placebo and one or more active treatment doses. This convention accommodates the way the statistics discipline favors categorical independent variables by converting dose, which tends to be an inherently dimensional variable, into an artificially categorical independent variable. In contrast to GAS, the specified CASM platform enables users to obtain reliable and valid within-patient evaluations of safety and effectiveness by longitudinally randomizing two or more treatment doses to different periods for each person.

The specified CASM platform helps users advance beyond levels of variables at one or a few sporadic points in time to temporal-interaction measures per se. The discussion of FIG. 2 in Section 5.1 exemplifies the importance of this distinction and advancement beyond levels of variables at various times to actual temporal-interaction scores. Using the terminology of network graphs, the specified CASM platform quantifies evidence for edges with temporal-interaction scores when nodes are time series.

The discipline of statistics includes some capabilities to use time-dependent independent variables as in ABAB crossover designs. For example, A could be placebo, and B could be one dose of active treatment presented in random order. ABAB designs are a small step toward obtaining treatment measures that are reliable and valid for individual patients. However, it becomes increasingly difficult to extend the statistical ABAB approach when there are more than two doses and many repeated measurements. Drugs often are manufactured and consumed in more than two doses. Data from ABAB clinical trials can be processed with the specified CASM platform despite limitations and deficiencies of typical ABAB designs. The specified CASM platform can also explore evidence for safety and effectiveness as functions of, for example, levels of a drug in bodily fluids. Levels of drugs in bodily fluids can be studied as examples of independent action variables.

With the specified CASM platform, drug development often could proceed from the first person on the drug up to groups and populations as distinct from group averages down to individual patients. Gaining quantitative significance and power with larger numbers of repeated measurements in multivariate time series can be less costly than gaining quantitative significance and power with larger numbers of subjects.

Medicine involves more complex adaptive systematicity and dimensionality than being treated or not treated, responder or non-responder, cured or not cured, dead or alive. There is more complex adaptive systematicity to medicine than can be captured with mathematics, statistics, and SI units of measurement. The specified CASM platform helps account for complex adaptive systematicity more scientifically through measurement. Section 6 provides more information about the why and how of quantifying evidence for complexity, adaptivity, and additional manifestations of complex adaptive systematicity.

Figure 3A:
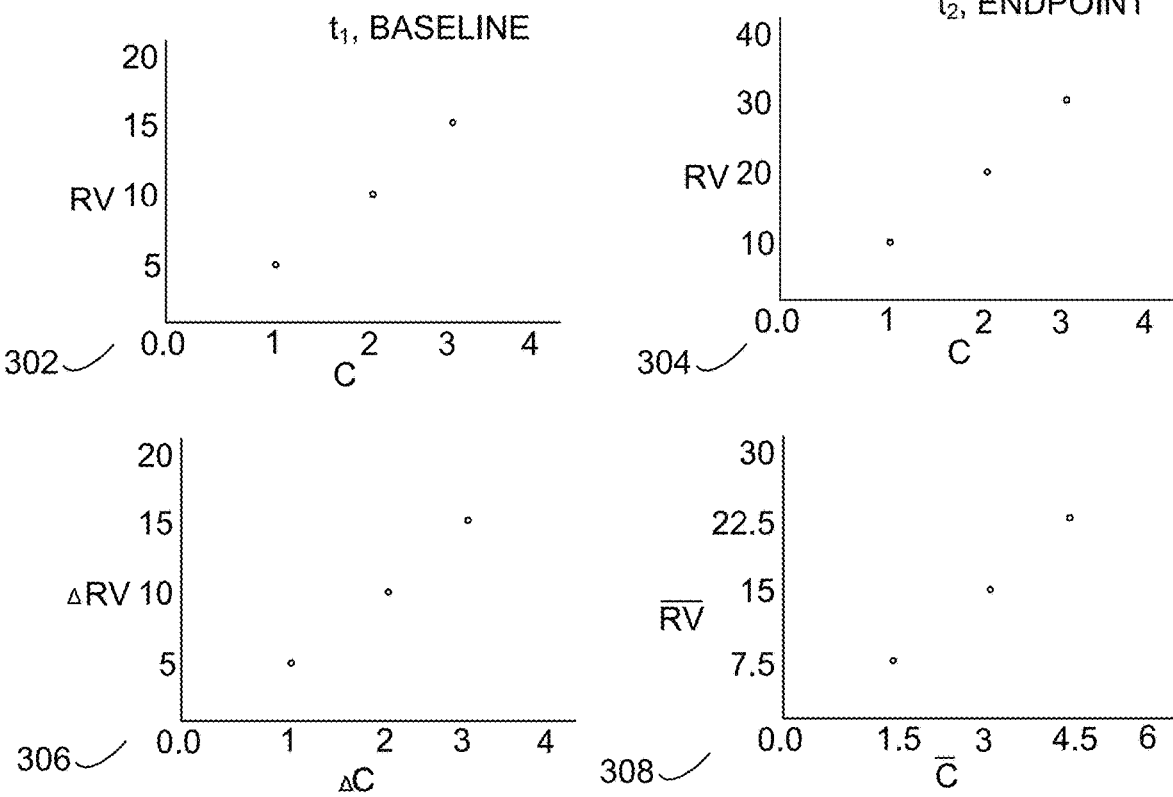
FIGS. 3A-3B depict graphs illustrating a comparison of two quantitative methods and systems to correctly identify and account for the ground-truth fact that supplemental estradiol was beneficial for a plurality of patients.
Figure 3B:
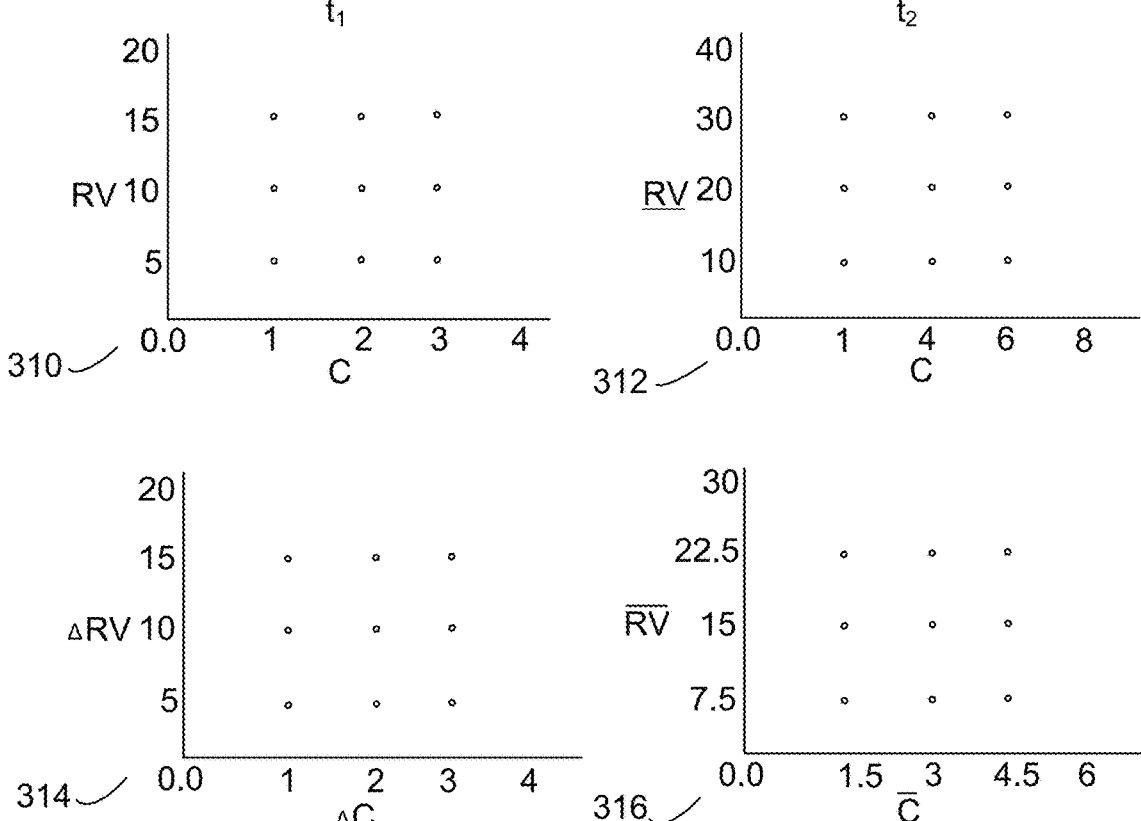

Also, FIG. 3B (Section 5.2) suggests that GAS RCTs can yield false-negative results for a reason other than a lack of statistical power. Finding that a drug is not effective when a drug is effective also could hinder and reduce pharmaceutical industry productivity.

Another approach to targeting the right drug to the right patient at the right dose is the big data approach. This approach often involves big data integration as with electronic medical records, clinical trial data, real-world evidence, and artificial intelligence. A limitation of this approach with artificial intelligence is that existing data lack any equivalent to what this disclosure identifies in Section 9 as EBM-2G quantitative temporal-interaction phenotypes or EBM-2G quantitative temporal-interaction tests for internal function, response, and agency. Without measurement first, as with the specified CASM platform, such information patterns are not yet in the data to be recognized with intelligence, natural or artificial. Measurement, including computation of derived units of measure, such as temporal-interaction scores, often needs to come before additional data processing.

3. The Specified CASM Platform

The specified CASM platform computes temporal-interaction scores that quantify evidence about how individual CAS work in the time dimension. Temporal-interaction scores are expressed in a universally standardized unit of measurement identified as the bagne. The specified CASM platform achieves such universal standardization by computation from multivariate time series data. The scientist's job has been described as figuring out how the world works. The specified CASM platform can often help stakeholders in CAS, including scientists and engineers, to achieve their objectives.

This disclosure defines work differently from how SI defines work with joules as the SI unit of measurement. Physics defines a joule as being equal to the exerted force times the distance over which it is exerted. In contrast, the specified CASM platform quantifies work by computing temporal-interaction scores that quantify evidence for temporal interactions between and among discrete events defined within and over periods of time on two or more action variables. There can be no temporal interaction without action in the action variables. Categorical variables about groups and populations are not action variables about individuals.

This disclosure makes a distinction between relatively stable variables and action variables. Examples of relatively stable variables include each person's unique germline genetic characteristics. Genetic characteristics help identify, distinguish, categorize, and group persons from conception to long after death. Genetic markers often can identify susceptibility to disease and can help predict treatment response. However, genetic markers alone are of limited value for making more subtle distinctions about being healthy, disordered, or diseased. In contrast, action variables can have two or more levels that can vary and fluctuate in level over a series of discrete periods in the individuals' time dimension. According to this disclosure, action variables can be variables about the individual CAS itself or about its environment, endogenous or exogenous.

Genetic differences are relatively stable. EBM-2G extends opportunities to use genetic and other relatively stable markers and variables that identify and distinguish individuals by quantifying evidence for temporal interactions between two or more action variables. EBM-2G includes computing EBM-2G quantitative temporal-interaction phenotypes and tests for patient diagnosis, treatment management and evaluation, and human agency. EBM-2G quantitative temporal-interaction phenotypes and tests offer to expedite genotype-phenotype mapping as needed to identify person-specific predictors of disease susceptibility, treatment response, and optimal safe and effective doses.

The specified CASM platform uses independent action variables to define discrete independent events as being either present or absent for discrete periods. Likewise, the specified CASM platform uses dependent action variables to define discrete dependent events as either present or absent for discrete periods. In contrast to digital series, dimensional independent and dependent variables have more than two levels. The specified CASM platform can accommodate dimensional action variables. CASM can convert all dimensional action variables into digital series sets, without information loss, before further data processing. Accordingly, the specified CASM platform goes beyond how digital computers represent numbers with ones and zeros and may be uniquely digital compared to how other methods, such as statistics, typically process dimensional data. The specified CASM platform is said to be ultra-digital because it converts each action variable time series into a set of digital time series, without necessary information loss, before further processing. Ultra-digitality enables multiparametric patterns of temporal-interaction scores to be expressed in universally standardized units (i.e., bagnes) and estimating the quantitative significance of temporal interaction scores.

For emphasis, the specified CASM platform distinguishes action variables from categorical variables. The statistics discipline uses categorical independent variables far more frequently than time-varying independent variables or independent action variables. The specified CASM platform ensures that both independent action variables and dependent action variables have two or more levels to yield temporal-interaction scores with non-zero magnitudes. There can be no temporal interaction without action or activity in the action variables.

As described above, temporal resolution refers to the time between repeated measurements in the action variable time series. As health-related examples of temporal resolution, brain activity can be measured in seconds or less while verbal reports as of pain in experimental studies could be in five-minute periods for hours. Both drug doses and blood pressure levels could be assessed daily over weeks, months, and years. Assessments of diet, exercise, and weight for obesity studies could be summarized within weeks over months and years. Death and hospitalization rates in populations can be assessed repeatedly in days, weeks, months, and years over decades. Activity within discrete periods can be event counts as when pulse rate is expressed as beats per minute. Ratings about mood and quality of life can be summarized over discrete periods such as days, weeks, or months. Additionally, action variables can quantify levels of activity in various bands as from Fourier analysis. For example, electroencephalograms often are decomposed into bands such as beta, alpha, theta, and delta.

Data to be processed by the specified CASM platform are identified as multivariate time series. The value for each repeated measurement in an action variable time series quantifies the amount of some action or activity within that period. Temporal-interaction scores computed with the specified CASM platform uses at least two repeated measurements of at least two time series for temporal-interaction scores to have non-zero magnitudes. Larger numbers of repeated measurements yield temporal-interaction scores with larger magnitudes when there is a temporal interaction. Temporal-interaction scores with larger magnitudes, positive or negative, quantify more evidence for temporal interactions. Positive temporal-interaction scores quantify evidence that higher levels of one or a set of independent action variable time series are associated with higher levels of one or a set of dependent action variable time series. Negative temporal-interaction scores quantify evidence that higher levels of one or a set of independent action variable time series are associated with lower levels of one or a set of dependent action variable time series.

Temporal-interaction scores are expressed in standard deviation units. A temporal-interaction score with magnitude zero provides no evidence for a temporal interaction between discrete events defined on one or more independent action variables (independent events) and discrete events defined on one or more dependent action variables (dependent events). Magnitudes of temporal-interaction scores can increase indefinitely with the number of repeated measurements in the multivariate time series when there is a temporal interaction.

The bagne is a universally standardized measure of the amount of evidence for interaction over time between two or more action variables. As described above, the universal nomenclature refers to how the computational process applies to action variables about any activity that can be measured repeatedly and CAS of any type rather than about consensual acceptance as of scientific paradigms.

In some embodiments, the bagne is a universal standard unit of measurement for quantifying the amounts of evidence for temporal interactions between and among action variables. It is a demonstrable fact that every temporal-interaction score expressed in bagnes is one score from a standardized discrete probability distribution of all possible scores. This distribution of all possible scores is determined by the multivariate time series data that were processed in combination with the operationally defined CASM scoring protocol used to compute the temporal-interaction scores. The resulting discrete probability distribution is a family of mutually exclusive and exhaustive temporal-interaction scores, said family having a mean of 0 and a standard deviation of 1, unless 0 is the only possible score. The only possible score is 0 when there is no action in independent events, dependent events, or both. For example, both drug dose and blood pressure levels must vary in the time dimension to compute a temporal-interaction score with a non-zero magnitude. Data about static variables and data collected cross-sectionally at one point in time do not provide evidence for temporal interactions as temporal interactions are quantified with the specified CASM platform.

As computed with the bagne as a standardized unit of measurement, temporal-interaction scores apply for individual CAS and sets of action variables. Just as statistical measures of group central tendency and dispersion apply to variables and individuals of many different types, temporal-interaction scores computed with the specified CASM platform apply to many types of variables and CAS. Correlation coefficients, a major statistical tool, often have been misapplied to multivariate time series. Correlation coefficients are misapplied when they violate assumptions about linearity and independent measurements. Also, correlation coefficients are not expressed in standardized units of measurement. Universal standardization, made possible by digitization (Section 12.1), applies when at least one time series operates as an independent action variable, and one time series operates as a dependent action variable-whatever the time series happens to measure.

People often form subjective impressions and learn about temporal interactions from experience gained in the time dimension. Examples include: This drug makes me feel good; milk gives me gas; alcohol makes me tipsy. People often form subjective impressions by examining graphs of two or more time series. In contrast, conventional RCTs (randomized controlled trials) often assess relationships by comparing groups at endpoints. Persons often make predictions and act according to their subjective impressions about temporal interactions. The specified CASM platform can often be a scientific alternative to such subjective impressions. The scientific alternative can be more informative and help contribute to productivity through cumulative knowledge, based on measurement.

The specified CASM platform can be applied for both data mining and hypothesis testing. When used to test a hypothesis, the specified CASM platform scoring protocol should be defined in complete detail before data collection and processing. Pre-specified protocols are already standard good practice as in cross-sectional clinical trials. The same pre-specification hypothesis testing principles apply for both conventional cross-sectional RCT designs and longitudinal EBM-2G RCT designs enabled by the specified CASM platform.

For data mining, the specified CASM platform is a tool to recognize and quantify evidence for temporal-interaction patterns in multivariate time series data. The goal for pattern recognition with the specified CASM platform is to identify scoring options that provide the most evidence for temporal interactions in the processed data as quantified by temporal-interaction score magnitudes, positive or negative. The specified CASM platform builds knowledge by recognizing and quantifying evidence for patterns of temporal interaction about how CAS work in the time dimension.

Patterns of temporal interaction quantified with the specified CASM platform offer a more objective and scientific alternative to subjective judgments or impressions about how CAS work. This advantage of measurement is like how rulers and tape measures are a more objective and scientific alternative to subjective impressions about lengths of objects being long or short, longer, or shorter. Similarly, bathroom scales are a more objective means to measure body weights than subjective impressions about being heavy or light, heavier, or lighter.

The following eleven points exemplify how the specified CASM platform can build knowledge by quantifying evidence for temporal-interaction patterns between the dose of a drug for pain and ratings of pain itself.

One application of the specified CASM platform is to quantify evidence that a drug is safe and effective regarding dependent or response action variables. The following example assumes that it is feasible to collect multivariate time series data about both drug dose, an independent or treatment action variable, and a host of dependent or response action variables that might be affected either beneficially or harmfully by the drug. Doses can be randomized longitudinally to help assure that results are valid for individual patients. This example illustrates a selected subset of capabilities of the specified CASM platform. All the following eleven points about an analgesic would apply during both clinical drug development and clinical practice. All eleven points about the specified CASM platform are different capabilities of the one specified CASM platform. These capabilities include natural facts that need to be accounted for to gain rigorous scientific knowledge to evaluate safety and effectiveness. This discussion assumes that the investigational analgesic already had successively passed carcinogenicity and teratogenicity testing.

First, and perhaps foremost, the specified CASM platform applies to multivariate time series data about individual persons one by one as required to quantify and understand individual differences in how individuals work in the time dimension. Pain tolerance can differ dramatically person by person. Persons respond differently to drugs. Furthermore, persons use a plenitude of different drug types for pain, different drugs work through various mechanisms, have different beneficial and harmful side effect profiles depending on doses, and affect individual persons differently. Targeting the right analgesic to the right person at the right safe and effective dose remains a mostly unsolved problem. Group average effects are not good enough for individuals.

Second, pain can decrease over time as from the healing of an injury. Pain can increase over time because of disease progression as with cancer. The specified CASM platform includes a capability to help separate relatively short-term treatment effects from longer-term trends.

Third, pain ratings are subject to measurement errors and the effects of uncontrolled variables. The specified CASM platform uses information from larger numbers of repeated measurements to help separate treatment effect signals from noise. Longitudinal dose randomization helps assure that benefit and harm scores are valid measures of treatment effect.

Fourth, analgesic pain response can be delayed because drug absorption and distribution take time. The specified CASM platform includes a capability to quantify safety and effectiveness as a non-linear function of response delay.

Fifth, pain response to a drug can persist because drug metabolism and excretion also take time. The specified CASM platform also includes a capability to quantify safety and effectiveness as a non-linear function of response persistence.

Sixth, pain drugs typically have many effects, both beneficial and harmful. The specified CASM platform provides a common metric to integrate and balance a host of beneficial and harmful effects as a function of dose.

Seventh, the safety and effectiveness of pain drugs almost certainly are non-linear. The fact that a pain drug is safe and effective at any one dose does not mean that higher doses are safer and more effective. The specified CASM platform includes a capability to quantify safety and effectiveness as a non-linear function of dose.

Eighth, people can adapt to analgesics as through tolerance and sensitization. The specified CASM platform includes a capability, identified as iterative processing, to detect adaptation in the time dimension.

Ninth, analgesics' safety and effectiveness are often affected in non-additive ways by other drugs, alcohol, and other environmental exposures. The specified CASM platform includes a capability, identified as Boolean independent events, to help account for synergy or antagonism.

Tenth, people have been known not to consume their medications as prescribed. Instead, patients might consume their drugs episodically. Episodic drug consumption can lead to episodes of health response. The specified CASM platform includes a capability to account scientifically for episodes of both independent treatment events and dependent response events.

Eleventh, decision-makers need to know if scores quantifying evidence for safety and effectiveness are quantitatively significant in addition to temporal interaction (benefit and harm) scores being expressed in standardized units of measurement. The specified CASM platform includes the capability to estimate quantitative significance (Sections 4.10 and 12.8).

The first person on an investigational pain drug and other stakeholders can benefit from all eleven capabilities of the specified CASM platform that were just exemplified. Continuing to do so for a person would lead to developing a cumulative body of quantitative scientific knowledge that could be applied to test hypotheses about that person. Hypothesis testing protocols should specify in advance all data collection and data processing operations.

Knowledge of analgesic safety and effectiveness often needs to be extended beyond individual persons studied one by one. Accordingly, universally standardized temporal-interaction scores from two or more persons or other CAS are suitable for statistical aggregation, statistical modeling, statistical analysis, and statistical inference from samples of individuals to populations.

Response, as exemplified above for pain treatment evaluation, is one of three components of work. As already stated, the specified CASM platform uses at least one independent action variable and at least one dependent action variable, which leads to a tripartite definition of work depending upon whether these action variables are internal to or characteristic of either the CAS itself or the environment of that CAS.

FIG. 1A is a block diagram illustrating an operational definition for Complex Adaptive System (CAS) work architecture 100 as quantified with temporal-interaction scores for use with embodiments described herein. Distinctions between (i) internal function 102, (ii) response 104, and (iii) agency 106 are operationally defined. FIG. 1A illustrates the workings and time-dependent mechanisms of individual CAS. In this example, the work architecture 100 is defined in the time dimension with the arrow of time 101. Agency

106 includes human agency. While the following examples refer to human health and medicine, the same principles apply more generally to basic and applied sciences of CAS regardless of type.

FIG. 1A indicates that an individual complex adaptive system is considered to have a boundary that helps distinguish that which is part of or an aspect of an individual complex adaptive system from its environment 108. Cell walls epitomize boundaries for CAS. Anatomy is about individual living systems of many types and distinguishes that which is part of the individual as distinct from the individual's environment 108. Genome sequence information and demographic information are major ways to identify, distinguish, and classify living CAS, including persons.

An indefinite number of action variables, such as the composition of one's microbiome, can be studied as if they are either inside or outside an individual's boundary. Similarly, and by example, the specified CASM platform can be applied to quantify evidence for drug response using various independent action variables. Prescribed drug dose can be used for intent-to-treat analyses. Consumed drug dose can be used to study the health effects of adherence and non-adherence to prescribed treatment regimens. Further, drug or drug metabolite levels in biofluids can be used to score evidence of safety and effectiveness. Boundaries distinguish individual persons from each other, with individuals being countable as in a census. By analogy, state and national economies and other non-physical CAS are considered to have boundaries.

As shown in key 110, circles represent action variable nodes. The nodes (e.g., node 112, node 114, etc.) are heterogeneous as distinct from collections of rule-following self-similar agents, such as birds in flocks or fish in schools. While each node in FIG. 1A is not labeled, it should be understood that each circular shape in FIG. 1A represents an action variable node. Each node (e.g., nodes 112, node 114, etc.) represents a time-dependent action variable as an object of interest regarding an individual complex adaptive system. Some nodes can be measured repeatedly with SI units of measurement. Also, nodes 115, such as for a person can represent verbal reports or rating scale measures such as pain, anxiety, and depression; quality of life measures; and psychometric or sociometric measures. Many time series may result from monitoring CAS.

Each of two or more nodes in FIG. 1A represents a quantity that has been monitored, measured, assessed repeatedly, and sometimes controlled and randomized for different periods in the time dimension to yield, as defined previously in this disclosure (Section 1), multivariate time series data. Multivariate time series data includes streaming multivariate time series that can monitor variables themselves and quantify and monitor temporal interactions in near-real-time (Section 8). 'Experimental multivariate time series data' are obtained while one or more independent variables are under longitudinal randomized experimental control.

This disclosure, including FIG. 1A, makes an operational distinction between genetic variables that identify and distinguish individual CAS such as persons and cancers from nodal action variables that quantify how individual CAS work in the time dimension. In general, genetic variables are assessed only once to identify and distinguish a person from conception to long after death. In contrast, nodal action variables often need to be assessed repeatedly as with multivariate time series to quantify how individual persons work in the time dimension with respect to function 102, response 104, and agency 106.

The fact that the specified CASM platform processes multivariate time series facilitates scientific assessments of temporal phenomena such as delay of effect for internal function, response, and agency as well as effect persistence for internal function, response, and agency. Information deriving from measuring or quantifying temporal interactions as well as benefit and harm can be used to help distinguish causation from mere correlation. Randomized experimental control can be exercised longitudinally as within persons as distinct from cross-sectionally as with GAS RCT designs.

Levels of an indefinite number of nodes, exemplified for biosciences and medicine, are expressed in SI units of measurement for physical quantities such as drug doses, concentrations of biologically active molecules in biofluids, electrophysiological variables, measures of brain activity, and speed and angular momentum of bodily motion as from motion capture technology. Action variables can include activity levels in frequency bands (e.g., gamma, beta, alpha, theta, and delta) as in electroencephalography. Nodes can include repeated ratings of pain, mood, and quality of life not expressed in SI units. Inclusion of nodes at biological, psychological, and social levels of study can help enable integrative medicine.

FIG. 1A uses lines (e.g., line 116) between nodes, often identified as edges in graph theory terminology, to represent temporal interactions. Temporal interactions can be associative or causal. Arrows in FIG. 1A indicate measures capable of providing causal evidence, as distinct from merely associative or correlational evidence. FIG. 1A uses solid lines and arrows between nodes to show positive or excitatory temporal interactions. Temporal-interaction scores are positive when higher levels for one time-series node are associated, potentially causally, with a second node's higher levels. FIG. 1A uses dashed lines and arrows between nodes to show negative or inhibitory temporal interactions. Temporal-interaction scores are negative when higher levels for one time-series node are associated, potentially causally, with a second node's lower levels.

FIG. 1A includes how CAS such as living persons use regulatory control mechanisms to maintain homeostasis as required for survival. Users of the specified CASM platform can also quantify the workings of collective entities such as populations studied as wholes. For example, users can quantify temporal interactions between daily air pollution levels and daily hospitalization or death rates in geographically defined populations.

3.1. Quantifying Evidence for Internal Function with Temporal-Interaction Scores:

FIG. 1A shows internal function 102 as a component of work. Internal function 102 is defined as involving both one or more independent action variable nodes, and one or more dependent action variable nodes that are internal to or characteristic of an individual complex adaptive system. Internal function 102 for internal medicine is exemplified by how endogenous insulin levels help regulate blood glucose levels. Temporal-interaction scores offer to quantify healthy or normal internal function, ordered and disordered mechanisms, regulatory control, coordination, coordinated action, and the like. Temporal-interaction scores also offer to quantify disordered internal function, disordered mechanisms, dysregulation, incoordination, discoordination, and the like. Chronic disorders and diseases involve disordered internal function.

Mathematical functions—a different use of the term function—are idealizations of how quantities relate to each other or interact. In contrast to such idealizations, the specified CASM platform computes empirical, data-driven measures that quantify actual evidence for temporal interactions that quantify how CAS are working in the time dimension. Direct measurement of temporal interactions is especially valuable when complex adaptive systematicity impedes progress and productivity achievable by applying the physical sciences, mathematics to SI units of measurement, approach to basic and applied sciences of CAS. The specified CASM platform enables users to quantify and study temporal interactions between and among other quantities as non-linear functions of analysis parameters such as independent action variable level, dependent action variable level, delay of effect, and effect persistence. Once measured, temporal-interaction scores can be modeled mathematically much as other measurement units are modeled mathematically. Also, temporal-interaction scores about a plurality of CAS in the same category can be aggregated, modeled, and analyzed statistically.

Temporal-interaction scores can quantify ordered and disordered internal function between two or more time series internal to or characteristic of an individual complex adaptive system. In contrast, a particular time series or set of time series of action variable interactants do not quantify internal function. The specified CASM platform uses more than one action variable to quantify internal function in the time dimension. Additionally, multiplex assays and cross-sectional measurements made at only one or a few points in time do not quantify internal function as function is included in FIG. 1A. For example, protein fingerprints do not measure function. Temporal-interaction scores quantify more than what the time-series action variables themselves measure.

A sports analogy might help to illustrate the amount-of-information-advantage of computing temporal-interaction scores compared to just having data about the action variable interactants themselves—the information advantage of quantifying how CAS work in the time dimension. Being a champion golfer takes more than generating action in feet, legs, hips, trunk, arms, wrists, hands, and clubs. The movements need to be in a temporal order. Being a champion takes coordinated, repeatable, and adaptive function. Good coordination can make difficult tasks look easy.

The specified CASM platform can help quantify coordinated action and uncoordinated action. Measurements are advantageously compared to subjective judgments. Motion is but one type of action that can be captured with multivariate time series data. Action also can be, as examples, molecular, electrophysiological, neuronal, physiological, psychological, and social.

Many action variables that could be used to quantify function with CASM instead often are measured one-by-one and only occasionally. Examples, grouped in overlapping categories, include levels of biologically active molecules, levels of electrophysiological variables, levels of signs and symptoms of diseases, levels of mental and physical performance, and levels of quality of life. Measures of temporal interaction can quantify functional and effective connectivity between and among activity or action levels in brain regions and voxels. Measures of temporal interaction can help integrate the physiological, psychological, and social aspects of human activity for the biopsychosocial approach to medicine and brain-behavior relationships.

The specified CASM platform applications include computing quantitative descriptions of normal and healthy or disordered and diseased internal function. These applications include computing mechanism-specific quantitative diagnostic temporal-interaction phenotypes and tests (Section 9.1). The specified CASM platform can compute such phenotypes using the same sets of data collection and data processing protocols for each of many patients or other persons. Then such diagnostic phenotypes can be clustered as with statistical and artificial intelligence methods to form diagnostic and phenotypic taxonomies based on measures of normal and disordered internal function.

Figure 4:
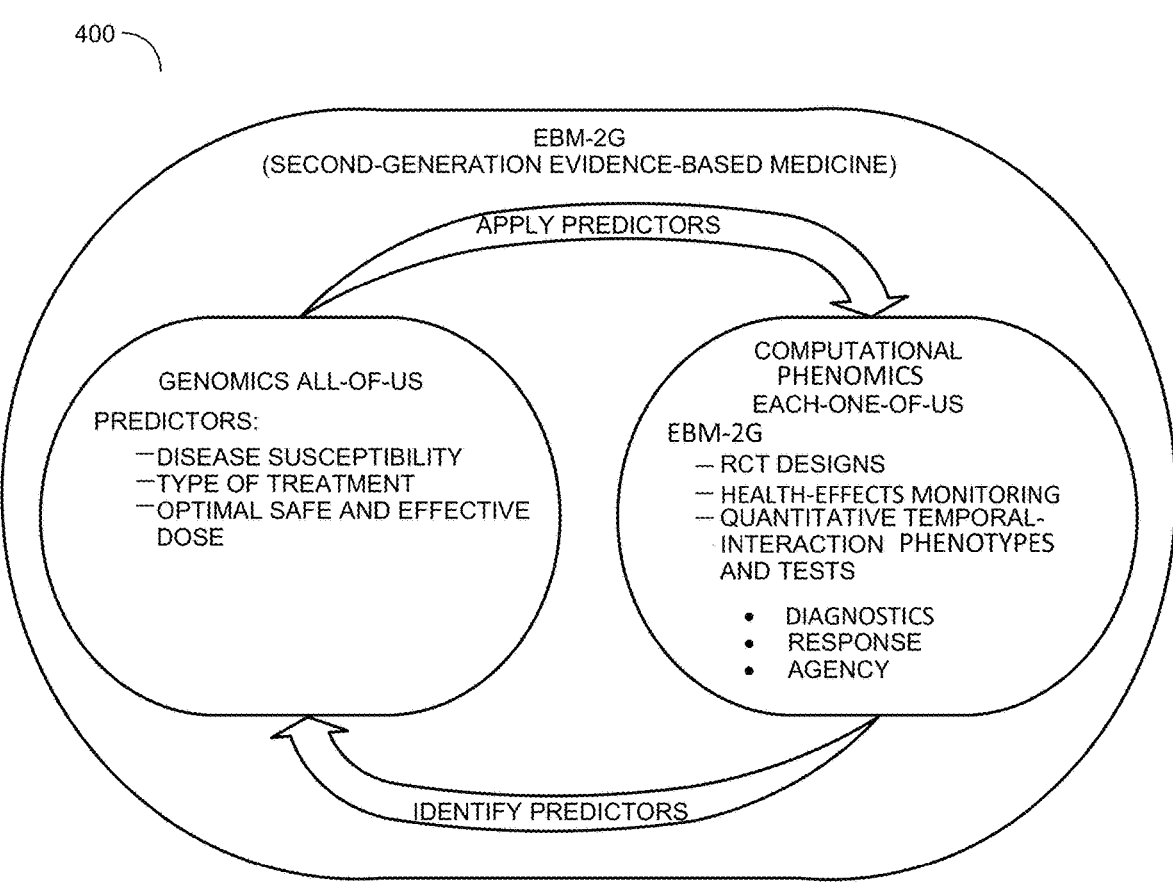
FIG. 4 is a block diagram illustrating a second-generation evidence-based medicine (EBM-2G) flow to identify and apply predictors for individual patients.

In contrast, prevailing diagnostic taxonomies of chronic disorders, as included in the International Classification of Diseases and the Diagnostic and Statistical Manual of Mental Disorders are based on disease signs and symptoms, not mechanisms. Also, EBM-2G quantitative temporal-interaction phenotypes and tests can accelerate the identification of genetic and other predictors of disease susceptibility. The specified CASM platform is needed to improve medical diagnoses and genomic prediction of chronic disorders for EBM-2G (FIG. 4).

Additionally, quantitative temporal-interaction diagnostic phenotypes computed with the specified CASM platform can become targets for drug discovery and development. Contrast quantitative temporal-interaction diagnostic phenotypes as drug targets with molecular drug targets. Unlike molecular drug development targets, temporal-interaction diagnostic phenotypes quantify evidence for mechanisms that can be up-regulated or down-regulated by drugs. CASM can be applied to quantify evidence for such up- and down-regulation. CASM offers to vastly increase the number of druggable targets.

3.2. Quantifying Evidence for Response with Temporal-Interaction Scores:

FIG. 1A also shows how this disclosure defines response 104. The definition of response 104 is when at least one time-series node quantifies levels of an independent action variable that is part of or an aspect of the environment of a complex adaptive system, making such independent action variables exogenous. Additionally, at least one time-series node must quantify levels of a dependent action variable that is a part or aspect of that complex adaptive system itself, making such dependent action variables endogenous.

Examples of independent exogenous action variables for a person include drug doses; nutrient levels; environmental exposure levels such as allergens, pollutants, and radiation; weather; and exercise levels. Additional examples are tasks such as performing mental arithmetic or the finger-to-thumb opposition task. Many treatments are environmental exposures or independent action variables delivered with therapeutic intent. Temporal-interaction scores quantifying evidence for response can be applied to help identify environmental triggers as of asthma attacks and inflammatory responses.

Quantifying treatment response mechanisms include quantifying how treatment might up-regulate or down-regulate internal function as internal function is quantified with temporal-interaction scores. An example is how an insulin-sensitizing drug for diabetes might up-regulate negative temporal interactions between insulin and glucose levels.

Measures of response can be diagnostic. Medicine uses challenge tests. The lactose tolerance test tests for lactose intolerance. The glucose challenge test is used to help diagnose gestational diabetes. Multiple challenge tests are used to help diagnose asthma and allergies. The specified CASM platform can quantify response when environmental exposures, natural or experimental, when both independent and dependent variables are action variables. Measures of treatment response can help confirm diagnostic indications. For example, measurements of glucose response to insulin can help confirm a diagnosis of diabetes. Measures of response can help confirm diagnoses of disordered function.

By extension, clinicians who manage patients to help prevent and control chronic disorders often conduct what can be characterized as informal single-patient experiments in the time dimension as for hypertension and major depressive disorder. Clinicians, in effect, test a hypothesis about an initial diagnosis by prescribing a drug at some initial dose and monitoring signs and symptoms in the time dimension while doses may be increased or decreased. An unsuccessful single-patient experiment might be followed by another experiment on the same patient with a different drug type or dose.

By further extension, people often conduct the same type of experiments on themselves in the time dimension as for prescribed drugs, over-the-counter drugs, nutritional supplements, and beauty products. Such person-own-control experiments often lead to non-adherence to physician-prescribed medications. Products of several types often are abandoned in medicine cabinets, drawers, and cupboards when experiments in the time dimension are perceived to be unsuccessful. Also, persons often adjust their diets according to perceptions about toward and untoward effects.

By still further extension, many species of animals are subject to appetitive or aversive operant conditioning. Operant conditioning can be conceptualized as a form of adaptation involving temporal interactions between and among stimuli, behaviors, rewards, and punishments. Operant conditioning is a type of adaptation which is introduced further in Section 6.3 of this disclosure.

Section 7 of this disclosure introduces how the specified CASM platform helps enable EBM-2G RCTs for individuals and groups by formalizing what clinicians, patients, and other persons do in real life. Evidence for safety and effectiveness can include randomization within individuals in the time dimension, collecting multivariate time series data about independent and dependent action variables, and processing such data with the specified CASM platform to compute universally standardized temporal-interaction scores.

Clinical drug development and medical practice often need to quantify evidence for safety and effectiveness response to investigational and approved drugs on persons. Much healthcare involves targeting the right drug to the right patient at the right safe and effective dose. Good targeting can optimize the ongoing treatment of individual patients while developing cumulative bodies of scientific evidence about treating groups and populations of patients now and in the future—a learning health care system. Additionally, the specified CASM platform can compute quantitative environmental and treatment response temporal-interaction phenotypes and tests (Section 9.2) needed to accelerate the identification of genetic and other predictors of differential response and optimal safe and effective doses of treatments for individual patients.

3.2.1. Temporal-Interaction Benefit-and-Harm Scores:

When used to quantify evidence for response, the specified CASM platform includes a variety of temporal-interaction scores. One variation is identified as benefit-and-harm scores. Benefit-and-harm scores can be used for evaluative studies such as clinical trials. Benefit-and-harm scores are temporal-interaction scores for which positive and negative signs can be reversed as might be needed so that all positive scores quantify evidence for benefit and all negative scores quantify evidence for harm. For example, both higher levels of high-density lipoprotein (good) cholesterol and lower levels of low-density lipoprotein (bad) cholesterol on higher drug doses can be evaluated as being beneficial. The specified CASM platform allows users to identify whether higher levels of a dependent or response variable time series are toward or untoward.

Whether higher levels of a dependent or response variable are toward or untoward can be set according to the clinical significance of treatment effects, patient preferences, and social value. Clinical significance includes using epidemiologic evidence to assess whether higher levels of laboratory or electrophysiological dependent action variable nodes increase or decrease the risk of major untoward or adverse events such as heart attack, stroke, cancer diagnosis or recurrence, and death. For example, personal preferences can account for individual differences in tolerance of pain compared to the tolerance of analgesic side effects such as drowsiness. Social significance involves being able to fulfill social roles, such as being able to do a job or being a parent, spouse, or caregiver.

3.2.2. Temporal-Interaction Benefit-and-Harm Scores, a Common Metric of Value:

Temporal-interaction benefit-and-harm scores can provide a common metric of value much as money is a common metric for various goods and services. One application of this common metric of value is quantifying evidence of safety and effectiveness regarding the effects of treatment action variables such as drug doses on response action variables such as pain and blood pressure levels. The proffered common metric is needed because all treatments and other interventions have multiple effects. Both primary effects and side effects can be both beneficial and harmful. The common metric of safety and effectiveness, enabled by the specified CASM platform, would allow decision-makers to integrate and balance beneficial and harmful effects scientifically. The specified CASM platform computes overall benefit-and-harm scores from benefit-and-harm profiles. Each profile can have a plurality of dependent or response action variable specific benefit-and-harm scores.

Both beneficial and harmful treatment effects can vary in importance by the response action variable. As examples, harmful effects can range from minor irritations to the harmful impacts predictive of life-threatening events. Similarly, beneficial effects can go from being of little importance to being of immense importance. Accordingly, the specified CASM platform allows users to apply importance weights to response action variable specific benefit-and-harm scores before averaging to compute overall benefit-and-harm scores for individuals.

As described elsewhere herein, both safety and effectiveness need to be assessed with two types of dependent, response, or predictive variables-action variables and non-action variables. The specified CASM platform applies directly to action variables. However, it also applies to non-action variables by applying differential weights to response variable specific benefit-and-harm scores while computing overall benefit-and-harm scores. Accordingly, safety in this disclosure refers to the totality of untoward or harmful effects of treatments and other environmental exposures across all response action variables. Likewise, effectiveness refers to the totality of all toward and beneficial effects. Unlike effectiveness, efficacy typically is evaluated with a primary response variable. Overall benefit-and-harm scores are comprehensive (Section 5.4.2.3) to the extent they cover all clinically and personally significant treatment effects.

Conventional treatment evaluation practice uses clinical trialists to have information and knowledge that they do not yet have to design clinical trials apt to be successful. In contrast, the specified CASM platform can help investigators obtain the necessary information to help target the right drug to the right person at the right safe and effective dose, starting with the first person on an investigational drug.

When computing overall benefit-and-harm scores, response-variable specific benefit-and-harm scores can be differentially weighted in accord with clinical significance, patient preferences, and social significance before being averaged to compute patient-specific overall benefit-and-harm scores. Users would be able to drill down to study both response-variable specific and overall benefit-and-harm scores as non-linear functions of multiple analysis parameters such as drug dose, response variable level, delay of response, and response persistence. The specified CASM platform enables users to estimate the quantitative significance of response-variable-specific and overall benefit-and-harm scores for each patient.

Dependent or response variable action variables can be included in evaluations of response before knowing if the temporal interactions between treatment and response action variables are beneficial or harmful. As examples, it may not yet be known if higher levels of a laboratory action variable increase or decrease major untoward health events. After temporal-interaction scores are computed for each of many individuals, it would be possible to study whether the temporal-interaction scores are positively or negatively predictive of major adverse health events such as heart attack, stroke, cancer diagnosis or recurrence, or death. Then temporal-interaction scores could be converted to temporal-interaction benefit-and-harm scores. However, all options should be specified in advance when testing hypotheses.

Temporal-interaction scores computed with the specified CASM platform quantify facts as Section 3 lists eleven facts about response to an analgesic. In contrast, benefit-and-harm scores quantify how these facts are valued, potentially starting at each person's level. The effects of having different values can be explored retrospectively. For example, temporal-interaction scores from clinical trials could be stored in databases. Then decision-makers could apply their own toward and untoward directionalities for response variables together with their differential weights to make treatment decisions in accord with their values as distinct from the values of some other person or group. This approach would avoid conflating or confounding treatment effects with how they are valued. This approach can also contribute to the hyper-personalization of self-care, medicine, and health care to prevent and manage chronic disorders.

When used as a common metric, benefit-and-harm scores can reduce the dimensionality of treatment evaluation problems from many to one. High dimensionality becomes a problem when investigators conduct multiple statistical tests on multiple response variables in one clinical trial. Conducting numerous statistical tests for one clinical trial can lead to false-positive results—a problem identified as data dredging. In contrast, users of the specified CASM platform can compute benefit-and-harm scores as a common metric in evaluative studies. Doing so would reduce dimensionality from many response variables to one overall benefit-and-harm score per person. Evaluation of safety and effectiveness regarding response action variables becomes a one-dimensional problem regarding response action variables. For example, evaluations of drug safety and effectiveness regarding many response or dependent action variables can be integrated and reduced to a one-dimensional problem with one overall benefit-and-harm score for each patient computed across many repeated measurements.

Conventionally, many RCTs for drug development, drug approval, and evidence-based medicine continue to define and test primary hypotheses defined in terms of primary response variables. RCTs that focus on efficacy neglect safety, thereby contributing to avoidable morbidity, mortality, ethical liability, and legal liability. In contrast, the specified CASM platform offers overall benefit-and-harm scores for evaluations of potential treatment action variables regarding many response action variables.

The specified CASM platform can help users avoid problems derived from inappropriate use of composite response action variables and multi-item rating scales as in clinical trials. As examples, composite rating scales for anxiety, major depressive disorder, pain, and quality of life can have ten, twenty, or more items. Rating scales for anxiety and depression typically have overlapping items. Some rating scales have items with differential weights. A customary practice in clinical trial designs is to test primary hypotheses with composite scores computed across all items. This convention reduces the dimensionality of treatment evaluation from many items to one dimension, thereby avoiding multiple statistical tests and false-positive results. However, this approach to dimensionality reduction in treatment evaluations with multi-item rating scales can be likened to putting various fruit types through a blender while still needing to preserve their identities. Irreversible blending impedes targeting.

In contrast, the specified CASM platform offers benefit-and-harm scores as a common metric to evaluate safety and effectiveness, starting at each person's level. Accordingly, safety and effectiveness can be profiled across all rating scale items. Then item-specific benefit-and-harm scores can be differentially weighted as needed before averaging across all items to compute one overall benefit-and-harm score for each person. The item-specific benefit-and-harm scores can be used to improve targeting the right drug to the right patient while overall benefit-and-harm scores, one for each person, can be used to evaluate one primary hypothesis about overall safety and effectiveness in a plurality of persons with one statistical test as for population medicine.

When applied to human health and medicine problems, the specified CASM platform can operate at the individual level to improve each person's health and healthcare. However, strategies that improve personal health will also improve group-average health for population health and public health. In some embodiments, the specified CASM platform may be used to quantify and evaluate how CAS respond to their environments 108.

3.3. Quantifying Evidence for Agency with Temporal-Interaction Scores:

FIG. 1A also shows agency 106 as a component of work in addition to internal function 102 and response 104. Agency 106 is defined as involving one or more independent action variable nodes that are internal to or characteristic of an individual complex adaptive system and one or more dependent action variable nodes in or characteristic of the individual's environment. Every person, and every CAS is an agent somehow and to some degree. Agency 106 includes how individual CAS act on their physical environments and other CAS, including other persons. Quantification of agency has the potential to help people be responsible agents.

Figure 2:
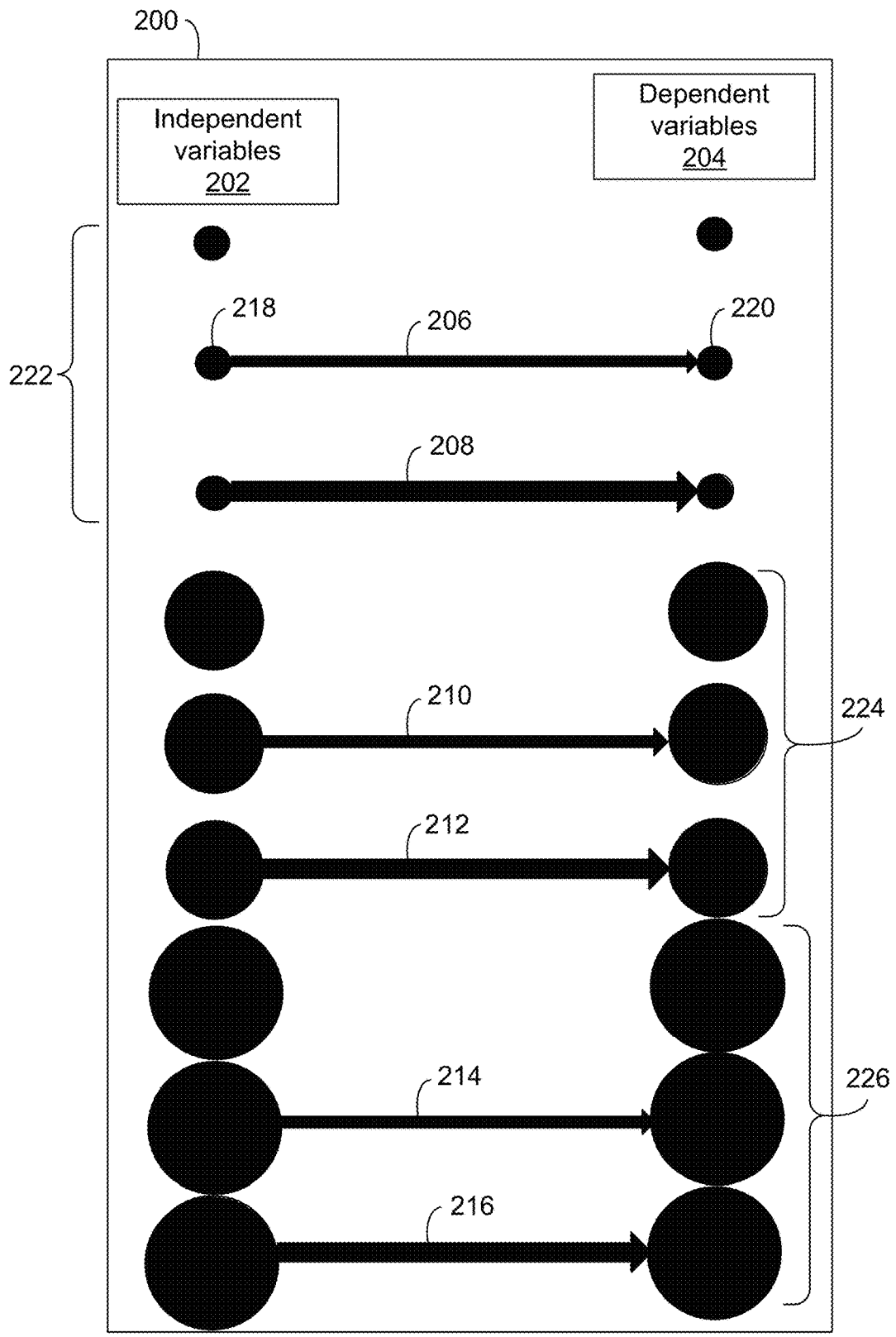
FIG. 2 is an example diagram representing temporal or longitudinal node-edge magnitude independence for an individual complex adaptive system.

3.4. Feedback:

Although not included in FIG. 1A, CAS typically manifest feedback mechanisms and control in the time dimension both (a) within and across the three components of work and (b) levels of study such as physiological, psychological, and social. As examples, attention through feedback modulates responses to visual stimuli. Behaviors related to diet, exercise, and environmental exposures can feedback to affect function and response. Masturbation is a more pointed example of how one's behavior can affect one's function and response. Feedback can contribute to longitudinal node-edge magnitude independence, as illustrated in FIG. 2.

3.5. The Specified CASM Platform Expands the Capabilities of Statistics:

Heuristically, it is valuable to recognize that statistics and the specified CASM platform are two distinct but often complementary and synergistic disciplines.

The statistics discipline is more cross-sectional, describes groups with statistical measures of central tendency and dispersion, and makes inferences from samples of individuals to populations. In contrast, the specified CASM platform is longitudinal and is about individuals. Stakeholders may blur such distinctions before realizing that CASM repurposes simple statistical tools, including hypergeometric probabilities, to measure individuals, as shown in Sections 4.7 and 4.8, Sections 12.5 and 12.6, and FIG. 14 through FIG. 17. Repurposing statistical tools for measuring individuals offers value much as repurposing drugs has provided value for persons, drug development, and medicine.

The statistics discipline processes data resulting from the measurement of individuals. Measurement includes computing quantities of derived or computed quantities such as density and concentration of individual material samples. Similarly, the specified CASM platform computes derived temporal-interaction scores and temporal-interaction benefit and harm scores applying to the individuals themselves but also suitable for descriptive and inferential statistics when there are two or more individuals. The calculation of temporal-interaction scores does require more computation than computing many other derived quantities such as density and concentration. Sections 5.4.2.1 through 5.4.2.4 introduce how the specified CASM platform can provide quantitative measures of treatment response that are reliable, valid, comprehensive, and detailed for each person. Sections 7.2 and 7.3 include descriptions about how benefit and harm scores computed with the specified CASM platform can be described and tested statistically when there are two or more individuals.

The specified CASM platform offers to relieve statistics of certain tasks for which the discipline of statistics is less than entirely suitable when it is possible to collect multivariate time series data inclusive of both independent and dependent action variables regarding many chronic disorders.

A prime and highly consequential example of CASM being more suitable than statistics involves causality assessments regarding CAS generally and applications GAS RCT designs (Section 2) to quantify and evaluate effects of chronic disorder drugs for persons more specifically. One problem is that GAS RCTs assess and evaluate causality with measures of group central tendency and dispersion much as applications of statistical mechanics to gas molecules, studied en masse, help explain the effects of temperature on gas pressure. Thus, decision-makers who chose GAS RCT designs when EBM-2G RCT designs (Section 7) are possible could be accused of studying persons like you more like gas molecules than persons manifesting complex adaptive systematicity (Section 6).

Figure 1B:
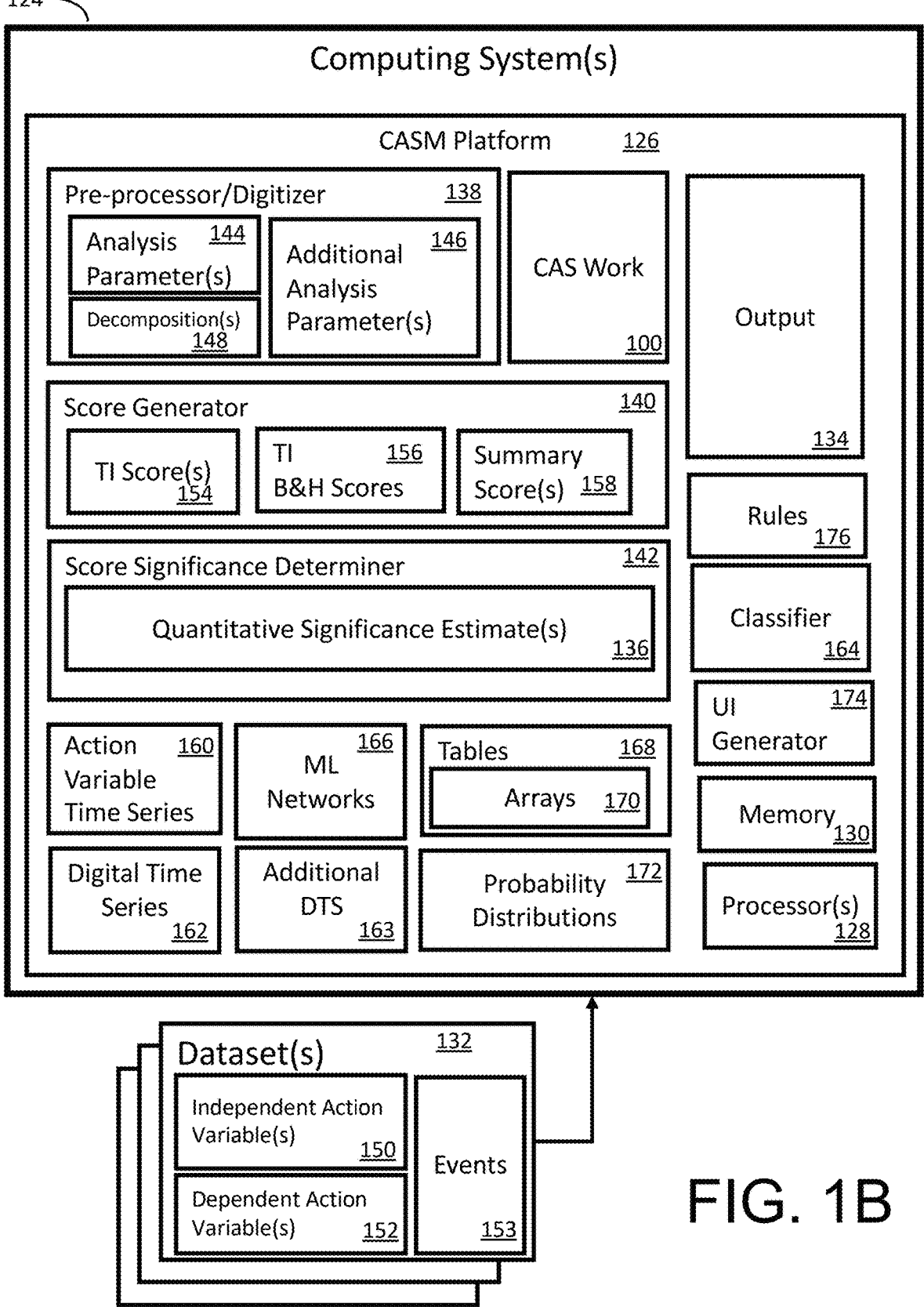
FIG. 1B is a block diagram illustrating an example computing system configured to use Complex Adaptive Systems Metrology (CASM) to generate temporal interaction scores, benefit and harm scores and to estimate their quantitative significance.

FIG. 1B is a block diagram illustrating an example computing system 124 configured to use Complex Adaptive Systems Metrology (CASM) to generate temporal-interaction scores and temporal-interaction benefit-and-harm scores and to estimate the quantitative significance of said scores. For example, the computing system 124 may include or access the CASM platform 126 adapted to function with the CAS work architecture 100 for particular individual CAS. The computing system 126 may include processors 128 and memory 130 to carry out operations described herein.

In some embodiments, the computing system 124 may operate on an individual complex adaptive system or set or sample of CAS associated with one or more datasets 132 (e.g., sets of data) to determine output 134 including, but not limited to temporal-interaction scores, temporal-interaction benefit-and-harm scores, and CASM significance levels of said scores associated with time-dependent variables from a study for an individual or a group of individuals studied as a composite individual CAS. In some embodiments, the output 134 may be generated as a basis for performing further analysis, including further analysis with CASM or with the discipline of statistics for groups and populations of CAS. For example, output 134 may be used to test statistical significance of temporal-interaction scores or temporal-interaction benefit-and-harm scores for pluralities of CAS. Additionally, output 134 may be input to artificial intelligence techniques.

As shown in FIG. 1B, the CASM platform 126 includes a pre-processor/digitizer 138, a score generator 140, and a score significance determiner 142. The pre-processor/digitizer 138 may access and/or generate analysis parameters 144 and additional analysis parameters 146 based on decomposition 148 (e.g., decomposed time series), datasets 132, or additional data accessible to system 124. In some embodiments, the pre-processor/digitizer 138 may modify datasets 132 (e.g., such as multivariate independent action variables 150 and/or multivariate dependent action variables 152) in any number of pre-processing steps according to decomposition 148, for example. The pre-processor/digitizer 138 may also digitize one or more action variable time series 160 (identified in datasets 132) to generate one or more digital time series 162.

The score generator 140 may access raw temporal-interaction (TI) scores and may generate TI scores 154. In addition, the score generator 140 may access raw TI benefit-and-harm (B&H) scores and may generate TI B&H scores 156. The score generator 140 may also determine and/or otherwise generate summary scores 158. The score significance determiner 142 may utilize output 134 based on scores 154, 156, and/or 158 to determine quantitative significance estimates 136.

In some embodiments, the CASM platform 126 may also classify or cross-classify data (e.g., digital time series 162) via a classifier 164, as described in detail below. In some implementations, the CASM platform may employ machine learning (ML) networks 166 to compute particular outputs 134.

The CASM platform 126 may generate tables 168 and arrays 170 in order to standardize raw scores and/or scores such as score 154, score 156, and score 158, and/or to generate probability distributions 172.

The computing system 124 may also include or be communicably coupled to a user interface (UI) generator 174. The UI generator 174 may generate content, such as tables, graphs, data, reports, and the like, for display on a device in communication with system 124. The UI generator 174 may be configured to ensure that the content is generated and accurately rendered within a display screen (not shown).

The computing system 124 may include any number of computing devices that take the form of a number of different devices, for example a standard server, a group of such servers, or a rack server system. In some embodiments, the computing system 126 may be a single system sharing components such as processors 128 and memory 130.

The computing system 124 may include or be communicably coupled to one or more processors 128 formed in a substrate, an operating system (not shown) and one or more memory devices 130. The memory devices 130 may represent any kind of (or multiple kinds of) memory (e.g., RAM, flash, cache, disk, tape, etc.). In some examples (not shown), the memory devices 130 may include external storage, e.g., memory physically remote from but accessible by the computing system 126. The computing system 126 may include one or more modules or engines representing specially programmed software.

In some embodiments, the CASM platform 126 may function as an application executing on a processor 128 of system 124. In some embodiments, the CASM platform 126 may function as an online application or service provided from a server device and accessible on a client device.

In operation, computing system 124 may receive a set of data 132 about an individual complex adaptive system, the set of data may include multivariate time-series action variables (e.g., variables 150 and 152) representing the individual complex adaptive system.

The computing system 124 may pre-process the set of data 132. The pre-processing may be performed by the pre-processor/digitizer 138. The pre-processing may include decomposing a time series into a decomposed time series 148 to remove linear and nonlinear trends before additional data processing. For example, when evaluating the effects of an analgesic longitudinally within a patient, computing system 124 would allow users to distinguish treatment effects from longer-term effects such as on pain from effects of healing or disease progression. The pre-processor/digitizer 138 may also digitize each time series action variable (150, 152) in the set of data that has more than two levels to a set of digital time series 162 comprised of zeros and ones to generate analysis parameters 144. The analysis parameters 144 may include at least an independent action variable level for one or more independent action variables associated with at least a portion of the set of data 132 and a dependent action variable level for a one or more dependent action variables associated with at least a portion of the set of data 132.

The score generator 140 may determine to select computation of either temporal-interaction scores 154 or temporal-interaction benefit-and-harm scores 156. The score generator 140 may then compute (e.g., calculate) the selected score(s).

In some embodiments, the computing system 124 may then determine additional analysis parameters 146 by generating a plurality of additional sets of digital time series 163. The generating of the additional sets of digital time series 163 may include applying operationally defined rules 176 to the digitized set of digital time series 162 for one or more independent action variables or the digitized set of digital time series for one or more dependent action variables.

The computing system 124 may employ the classifier 164 may then cross-classify each digital time series 162 for a respective independent action variable in the one or more independent action variables 150 with each digital time series 162 for a time series for a respective dependent action variable in one or more dependent action variables 152. The cross-classifying may include generating one or more multidimensional arrays of tables 168 where each table has at least one dimension for each of the analysis parameters 144 or the additional analysis parameters 146 and at least one array 170 for a plurality of events 153 associated with one or more independent action variables 150 and one or more dependent action variables 152.

The computing system 124 may compute, for each of the tables 168, either a raw and unstandardized temporal-interaction score or a raw and unstandardized benefit-and-harm score. The computing system 124 may also standardize each raw and unstandardized temporal-interaction score or each benefit-and-harm score so that each standardized score represents one score from a distribution of potential scores defined by the set of data 132 in combination with a CASM scoring protocol.

The computing system 124 may employ score generator 140 to generate a summary score 158 for each multidimensional array 170. The summary score 158 may be based on either the standardized temporal-interaction scores or the standardized temporal-interaction benefit-and-harm scores.

The computing system 124 may determine, based on the generated summary score 158 for each multidimensional array 170, a quantitative significance estimate 136 of the generated summary score 158 for either the standardized temporal-interaction scores or the standardized temporal-interaction benefit-and-harm scores.

4. Overview for Applying the Specified CASM Platform in Eleven Steps

Application of the specified CASM platform involves computing universally standardized scores that quantify the amount of evidence for temporal interactions. Temporal-interaction scores quantify evidence about how CAS work-function internally, respond, and act as agents. The specified CASM platform's application consists of an ordered series of eleven non-obvious and inventive steps for each complex adaptive system. Section 12 presents the steps two through ten in more detail. The following steps include the computation of benefit-and-harm scores and overall benefit-and-harm scores.

4.1. Step 1; Enter Multivariate Time Series Dataset:

The specified CASM platform applies to multivariate time series data as defined in Section 1. A multivariate time series dataset is analogous to a 'data movie' as distinct from a 'data snapshot.' According to this analogy, each action variable corresponds to a pixel. Data movies are a time-ordered series of data snapshots, each snapshot being analogous to a movie frame. Each snapshot or frame would be of the same set of action variables-all action variables measured using the same time frames. Data for time frames of equal length facilitate distinguishing causality from mere correlation—causes before effects—in non-experimental studies. Some specified CASM platform applications can use nested time series as when levels of pain, rated every 5 minutes, are related to temporal-interaction scores between and among neurons and brain regions with action or activity assessed at higher temporal resolution levels.

Compared to real snapshots or photographs, real movies or videos can provide orders of magnitude more information in the time dimension as about a story or sporting game. Similarly, data movies can deliver orders of magnitude more information needed to know, help predict, and manage how CAS work in the time dimension compared to data snapshots and change scores. More specifically, compared to data snapshots, data movies can provide orders of magnitude more information needed to help distinguish and understand scientifically differences between being alive and being dead, between being healthy and productive from being disordered and diseased. Data movies can provide the information needed to help bring molecules to life as components of living CAS. Data movies can help make drug development and medicine more scientific and patient centric.

This snapshot-movie analogy extends to development. The specified CASM platform develops data movies and gains value on data movies' amount-of-information advantage compared to data snapshots. As taken at the times of clinic visits and hospitalizations, data snapshots are short of information needed to quantify evidence for temporal interactions as needed for data-driven scientific understanding of how living and other CAS work in the time dimension. In contrast to point-in-time measurements, sensors, monitoring devices, and self-report electronic diaries provide more temporal information needed to quantify how CAS work in the time dimension (FIG. 1A).

RCTs exemplify the need for basic and applied sciences of CAS to graduate from data snapshots to data movies. RCTs of drugs need to evaluate safety and effectiveness. Many advances in biomedical sciences must translate through successful clinical trials. Then medicines can be approved for marketing by regulatory agencies, accepted by formularies, included in treatment guidelines for EBM, prescribed to patients, paid for by payers, and consumed by patients-all intended to improve the human condition.

Users of the specified CASM platform also can study dependent or response variables as action variables. Examples of response action variables include measures of pain, blood pressure, cholesterol, and mood. Distinguish action variables from baselines, endpoints, and change scores. Legacy GAS RCT designs often define artificial endpoints. Defining artificial endpoints on response action variables confounds artificial endpoints such as blood pressure levels with real endpoints such as death.

In contrast with legacy GAS RCT designs, EBM-2G RCT designs quantify evidence for each person's safety and effectiveness before any statistical aggregation, modeling, analysis, and inference from pluralities of persons to populations (Section 7). EBM-2G RCT designs increase scientific veracity (truthfulness) and help account for personhood's complex adaptive systematicity (Section 6).

GAS RCT designs lack scientific veracity because they rely on data snapshots when data movies are feasible. In contrast, EBM-2G RCT designs gain scientific veracity because they can develop data movies-multivariate time series datasets.

The data-and-information advantage of data snapshots over data movies will be exemplified for RCT designs. For purposes of this disclosure, baseline-to-endpoint change scores are a means to reduce two data snapshots into one data snapshot—a change score data snapshot. Since convention has it that primary hypotheses are defined on primary response variables, the GAS RCT design approach is like using one data snapshot with one pixel for each subject to evaluate a drug. The average cost of this data snapshot is high on a per subject basis. Most clinical trials do collect much more data than subject-specific data snapshots. One problem is that much of these additional data are never used to test primary hypotheses. Section 7.5 describes how some such additional data can be put to effective use while transitioning from GAS RCT designs to EBM-2G RCT designs. Section 6.9 describes how EBM-2G RCT designs can help increase patient-centricity.

EBM-2G RCT designs based on data movies can provide orders of magnitude more information for decision-making than GAS RCTs based on data snapshots. To illustrate, consider the following thought experiment. Suppose there is a need to evaluate the safety and effectiveness of a drug for hypertension.

Further, suppose that five different doses of one type of hypertensive, including placebo as zero-dose, can be randomized in two-week blocks over ten weeks in a single-person, placebo-controlled, double-blind, or masked EBM-2G RCT (Section 7.1). Blood pressure is monitored daily—it has a temporal resolution of one day.

Furthermore, suppose 30 additional response variables are monitored daily. These additional response variables could be about anticipated safety concerns, monitorable laboratory response variables, measures of physical or mental performance, person-reported ratings of mood, and response variables included to explore potential new indications or contra-indications. To illustrate the potential value of new indications, Viagra resulted upon the recognition that a cardiovascular drug bolstered erection. Also, suppose that toward and untoward directionality and relative importance weights for all 31 response variables, based on clinical significance assessments and patient preferences, were collected in advance of RCT data collection.

Such a thought experiment ten-week EBM-2G RCT would result in a data movie with 70 daily time frames and 32×70 or 2240 data points about one person. In contrast, a GAS RCT design would use a single baseline-to-endpoint change-score data-point to test a null hypothesis at the group-average level. The number of time series, 32, is the sum of one time series for randomized dose, one time series for daily blood pressure level, and the 30 additional time-series response action variables. Results from developing this data movie with the specified CASM platform can, as examples, include:

1. An overall benefit-and-harm score computed from all 2,240 data points to quantify evidence for safety and effectiveness for the single person studied in this thought experiment, 2. An estimate of the quantitative significance of this overall benefit-and-harm score to test the null hypothesis of no treatment effect (Sections 4.10 and 12.8). Rejection of the null hypothesis in the positive direction would indicate that benefits outweigh harms. Rejection of the null hypothesis in the negative direction would indicate that harms outweigh benefits, 3. A blood-pressure-specific summary with estimated quantitative significance to test a secondary hypothesis, 4. A benefit-and-harm profile showing summary benefit-and-harm scores across all 31 response variables in universally standardized units (Sections 4.8 and 12.6), 5. A graph showing overall benefit and harm as a function of dose. Knowing the optimal safe and effective dose could be used to guide person-specific continued treatment, and 6. A total of 31 graphs showing benefit and harm as functions of dose-one such graph for each response variable.

The hypotheses in points 2 and 3 above would be conducted with an intent-to-treat analysis. Further, exploratory studies could be performed using daily measures of actual drug consumption as well as with measures of drug or metabolite levels in bodily fluids.

Since the specified CASM platform does not use baselines or endpoints, evidence for safety and effectiveness could be monitored in near real-time over the 10-week clinical trial itself and beyond for as long as there is concern about safety and loss of safety and loss of effectiveness.

Next, in this thought experiment, assume that the above trial was conducted with each of 100 persons in a single-group, multiple single-person EBM-2G RCT (Section 7.2). Then the null hypothesis of no overall safety and effectiveness at the population level could be tested with a single-group t-test on the mean of the overall benefit-and-harm scores. Rejection of the null hypothesis in the positive direction would support the conclusion that the drug is safe and effective for the sampled population. Rejection of the null hypothesis in the negative direction would support the conclusion that the drug is not safe and effective. Note that this single-group t-test would use data from 224,000 data points—2,240 data points from each of 100 persons. The application of the specified CASM platform can simplify statistical aggregation and analyses. All six points listed above could be studied at the group-average level by applying statistics computed from the specified CASM platform measurements.

Furthermore, the specified CASM platform's use helps make it possible to cluster persons using statistical and artificial intelligence methods according to differential responses and optimal doses. Clustering, in turn, can help make it possible to classify persons regarding treatment response and, in turn, helping to identify genetic and other predictors of differential response and optimal safe and effective doses.

So far, in this section of this disclosure, the information advantage of data movies over data snapshots has been portrayed as a multiplicative relationship involving the number of action variables, the number of repeated measurements for each action variable, and the number of persons. This advantage was 2,240 to 1 for one person and 224,000 to 100 for 100 persons, not counting the use of two repeated measurements (baseline and endpoint for blood pressure). The actual potential information advantage of data movies over data snapshots is far greater. The following illustrates this greater advantage. Imagine trying to understand the plot of a real action movie with the frames shown randomly as distinct from temporal order. The information advantage of the frames in one data movie being in temporal order versus being in random order appears to be related to the number of permutations of temporal order in a data movie. The number of permutations is n factorial, where n is the number of repeated measurements or frames. The importance of temporal order to know how living systems work in the time dimension (FIG. 1A) appears to be analogous to the importance of the four nucleotides' spatial order from gene sequencing is to identify and distinguish living CAS.

The specified CASM platform gains value from the data movie frames' being in temporal order. Exemplary capabilities include being able to separate short-term treatment effects from longer-term trends, assess evidence of independent and dependent events that may be episodic, account for delay of effect and effect persistence, and quantify evidence that temporal interactions are causal in non-experimental data. Estimating the quantitative significance of summary temporal-interaction scores, summary benefit-and-harm scores, and overall benefit-and-harm scores are additional capabilities.

4.2. Step 2; Time Series Decomposition and Transformation Options:

The specified CASM platform includes an expandable set of options applied to the time-series action variables before further processing. One option allows users to process linear regression residuals as distinct from the time-series levels directly. For example, distinguish short-term treatment effects from longer-term trends by processing linear regression residuals. More specifically, linear regression residuals can help distinguish analgesic drug effects on pain from longer-term trends such as reductions in pain due to healing after injury or increases in pain from cancer progression. Other sources of long-term trends include sensor drift and economic growth. Another option is polynomial regression residuals. An option identified as 'successive differences' allows users to compute temporal-interaction or benefit-and-harm scores from successive differences between time points as distinct from the time point levels themselves. For example, living systems can be more responsive to changes in hormone levels than levels of the hormones themselves. Another example would be to adjust time series for seasonality before further processing.

When the specified CASM platform is being used to compute scores for hypothesis testing, any and all such examples of time-series decomposition should be specified before data collection and processing. When applied for data mining and pattern recognition, various time-series data decomposition options can be explored to identify CASM scoring protocols that yield scores with the highest magnitudes, positive or negative. Decomposition options such as polynomial regression residuals that overfit time series before further processing with the specified CASM platform would drive down magnitudes of temporal-interaction and benefit-and-harm score magnitudes.

4.3. Step 3; Digitize any and all Dimensional Time Series:

Next, the specified CASM platform enters a series of three steps to define discrete or digital events to be either present or absent within each discrete period or across episodes of discrete periods in one or more action variable time series. The first step in defining digital events is a form of digitization that extends beyond digitization already used to represent numbers in digital computers. This additional form of digitization and digitalization converts each action variable time series for a computerized dimensional or analog time series into a set of digital time series without necessary loss of information.

According to this disclosure, a dimensional or analog time series has more than two levels. In contrast, a digital time series has only two levels, 0 (event absent) or 1 (event present). All information in a dimensional time series can be captured with enough digital series. The specified CASM platform can process time series that are inherently digital. For example, the specified CASM platform can process daily data when drug for each day is either absent (0) or present at any nonzero dose (1) together with seizure events for each day being either absent (0) or present at any nonzero count of seizures (1).

The following simple example illustrates the digitization of analgesic dose as an independent action variable at an ordinal level of measurement when five doses (0 as for placebo, 10, 20, 40, and 80) are potentially randomized weekly and assessed daily. One digital series with both 0s and 1s would contrast all days with dose=0 (0, treatment event absent) with all days when the dose is 10 or more (1, treatment event present). An additional digital series would contrast every day with dose 0 or 10 as treatment event absent (0) with all days when the dose was present at 20 or more (1). Another additional digital series would contrast all days when doses are 0, 10, or 20 (0, absent) from days with doses are 40 or 80 (1, present). Another digital series would contrast every day when the dose was 40 or less (0, absent) from days with the dose was present at dose 80 (1). The original dimensional dose series could be reconstructed from this digital series set—no information is lost at an ordinal measurement level. Digitization at an interval level of measurement would require more digital series.

By extension, a dimensional series with 500 repeated measurements, all with different values, could be represented with 499 digital series at an ordinal level of measurement, each digital series having at least one 1 and one 0. Extension of digitization to the interval level of measurement for a time series with 500 repeated measurements could require many more than 499 digital series. In most cases, digitization of action variables beyond modest numbers of levels would rapidly drive-up demand for computing resources without adding much additional descriptive, explanatory, or predictive power or value.

The need to convert dimensional time series into sets of digital series is not obvious. Most methods for processing time series do not convert dimensional time series into sets of digital series. Part of the value of digitization derives from advantages gained by different and additional opportunities for further data processing to quantify evidence for patterns of temporal interaction.

The specified CASM platform uses analysis parameters. Digitization of one dimensional independent action variable time series creates independent action variable level as a required analysis parameter with one level for each digital time series. Similarly, digitization of one dimensional dependent action variable time series creates dependent action variable level as a required analysis parameter with one level for each digital time series. Levels of both independent and dependent action variable level are required analysis parameters when both variables are dimensional time series. Each additional dimensional time series action variable would require an additional set of digital series, each time series with its own analysis parameter to represent the level.

Digitization of dimensional time series with sets of digital time series offers advanced visions of a digital world as for digital medicine. Digitization of dimensional time-series action variables into sets of digital series is a key to the specified CASM platform. Digitization enables all the following steps.

4.4. Step 4; Apply Optional Analysis Parameters:

The specified CASM platform also uses optional analysis parameters to quantify patterns of evidence for additional factors that need to be accounted for when quantifying evidence about how CAS work in the time dimension. Optional analysis parameters, each with a specified range of optional levels, create digital series in addition to the digital series created by the required analysis parameters for independent and dependent action variable level. Applying operationally defined rules to the previously defined digital series makes each additional digital series. Optional analysis parameters allow a more fulsome accounting of how CAS work as the tripartite operational definition of 'work' as shown in FIG. 1A.

An operational version of the specified CASM platform allows up to six additional optional analysis parameters in addition to the required analysis parameters of independent variable level and dependent variable level. These six optional analysis parameters are (1) episode length and (2) episode criterion to account for independent action variable episodes of events, (3) episode length and (4) episode criterion to account for dependent action variable episodes of events, (5) delay of effect to account for delayed effects of independent events upon dependent events, and (6) effect persistence to account for persistent effects of independent events upon dependent events. Accordingly, this operational version of the specified CASM platform applies up to eight analysis parameters simultaneously; two required plus up to six optional analysis parameters. Each optional analysis parameter has a default level and a range of optional levels. Additional optional analysis parameters, each with its own range of optional levels, can be formed to help account for additional ways that CAS work in the time dimension. Applying operationally defined rules to previously defined digital series creates digital series for all optional analysis parameters.

As examples, analysis parameters for episodes can be applied when hormone secretion is pulsatile, and when periods of mania and depressed mood are episodic. Patients take drugs episodically, often because of non-adherence to prescribed treatment regimens. Non-adherence to prescribed treatment regimens can contribute to episodes of health events. Economies can have episodes of both economic growth and recession.

4.5. Step 5; Define Optional Boolean Events:

Independent action variables often have non-additive effects. Examples include when two or more drugs or two or more proteins have antagonistic or synergistic effects on dependent action variables. For example, sedative and analgesic drugs can interact, sometimes with deadly consequences. The specified CASM platform can account for such phenomena by applying Boolean operations to digital series previously defined with analysis parameters to define Boolean independent events. Examples of Boolean operations include AND, OR, NOT or AND NOT. The specified CASM platform defines and applies Boolean independent events after applying analysis parameters to help account for independent variable level, dependent variable level, delay of effect, the effect persistence, and any additional analysis parameters. This order helps account for facts such as the effects of Boolean events being dose dependent.

Capabilities of the specified CASM platform to apply Boolean independent events can be incredibly valuable for evaluating and optimizing treatment cocktails as when two or more drugs are used in combination.

Like Boolean independent events, the specified CASM platform can define and apply Boolean dependent events to help account for syndromes. Another way to account for syndromes is exemplified as when at least five of nine symptoms need to be present during a period as in diagnosing mental disorders such as major depressive disorder.

4.6. Step 6; Create 2×2 Tables:

Next, the specified CASM platform cross-classifies each digital series for an independent variable with each digital series for a dependent variable to form a 2×2 table for each digital series pair. Boolean event series would be based on sets of action variables. Let the cells of each 2×2 table be labeled a, b, c, and d. The number in each cell is a count of events defined by the pair of digital series where a is a count of periods when an event is present (1) for both digital series, b is a count of periods when an event is absent (0) for the independent variable but present (1) for the dependent digital series, c is a count of periods when an independent event is present (1) but absent (0) for the dependent event, and d is a count of periods when an event is absent (0) for both the independent and dependent digital series.

Events must be determinant, either present or absent, for both digital series to be included in a 2×2 table. Optional analysis parameters can yield indeterminate periods in a digital time series. As examples of indeterminate periods, a delay of effect event of four periods, defined on an independent variable, is indeterminate for the first three periods in a digital series. An episode length-seven event, defined on either an independent or dependent variable, is indeterminate for the first six periods in a digital series.

4.7. Step 7; Compute Raw Temporal-Interaction Scores:

The specified CASM platform computes a raw or unstandardized temporal-interaction score for each 2×2 table by repurposing simple statistical tools and applying them to measure evidence for temporal interactions. More specifically and first, the magnitude or absolute value of a raw temporal-interaction score for a given 2×2 table begins by applying the chi-squared formula. Although the resulting quantity is the sum of the squared differences between the observed and expected cell frequencies, the value is not referred to the chi-squared distribution to assess a probability or significance level. Doing so would be inappropriate because repeated measurements in time series typically are not independent.

Second, the specified CASM platform computes the a-cell's expected value and follows a simple set of rules to compute a raw temporal-interaction or benefit-and-harm score. Scores can be positive, negative, and zero. The raw temporal-interaction score is zero when the observed value of the a-cell equals the expected value of the a-cell.

4.8. Step 8; Universal Standardization of Temporal-Interaction Scores:

The specified CASM platform achieves universal standardization by recognizing that the marginal frequencies; a+b, c+d, a+c, and b+d; of an observed 2×2 table can be used to identify all 2×2 tables that are possible given the marginal frequencies of the observed 2×2 table. Then a raw temporal-interaction score is computed for each of these possible 2×2 tables. If any marginal frequency equals zero, there can be no evidence for temporal interaction. Then the temporal-interaction score would have a value of zero.

Next, the specified CASM platform computes the hypergeometric probability of each possible temporal-interaction score, possible given the observed marginal frequencies, to create a discrete probability distribution of raw scores.

Next, the specified CASM platform computes the mean and standard deviation of the raw scores' discrete probability distribution. It uses the resulting mean and standard deviation to compute the corresponding probability distribution of standardized scores. The universally standardized unit of measurement for temporal-interaction scores in the resulting distribution is called the bagne. All standardized scores in such distributions of potential scores are in bagnes.

Universal standardization means that each observed temporal-interaction score, including each benefit-and-harm score, expressed in bagnes, is one score from a distribution of potential temporal-interaction scores. This distribution has a mean of zero and a standard deviation of one unless zero is the only possible score. Zero is the only possible score when one or more of the marginal frequencies in a 2×2 table is zero. Investigators can examine the distribution of potential scores of which the observed temporal-interaction or benefit-and-harm score is a member. The fact that one can examine such discrete probability distributions holds true whatever the type of complex adaptive system, whatever the independent and dependent variables measure, and whatever individual complex adaptive system is measured.

The unique and valuable capabilities of the specified CASM platform are built upon digitization (Step 3) together with universal standardization (Step 8.)

4.9. Step 9; Summarize:

The specified CASM platform can quantify temporal-interaction patterns in substantial detail. Section 12.8 shows how the specified CASM can quantify one temporal interaction with multiparametric arrays with millions of standardized scores.

Almost invariably, users of the specified CASM platform would need to summarize this detailed information. The fact that all scores in such arrays are expressed in bagnes as a standardized unit of measurement facilitates summarization. For example, the temporal-interaction score with the largest magnitude, positive or negative, summarizes the array. The location of a summary score in an array identifies the conditions that yield the summary score in terms of analysis parameters and analysis parameter levels. Arrays can have extreme scores with equal magnitudes but opposite signs, in which the summary score is set to zero. Also, standardized score arrays can be summarized by analysis parameters one by one or in various combinations. For example, an analgesic's benefit and harm can be summarized as non-linear functions of dose, pain severity, delay of response, and response persistence.

4.10. Step 10; Estimate Quantitative Significance of Temporal-Interaction Scores:

Quantitative significance for the specified CASM platform, CASM significance, is to individual CAS what statistical significance is to groups, samples, and populations of whatever kind. In both cases, results are said to be quantitatively significant when observed results are improbable to have occurred given the null hypothesis of no temporal interaction. For example, the specified CASM platform makes it possible to test the two-tailed null hypothesis of no overall benefit and harm of treatment with an analgesic in an EBM-2G RCT for a person. Rejection of such the null hypothesis in the positive direction would support the alternative hypothesis that beneficial effects outweighed harmful effects for that person. Rejection of the same null hypothesis in the negative direction would support the alternative hypothesis that harmful effects outweighed beneficial effects for that person. Not rejecting the null hypothesis with a two-tailed test would support the alternative hypothesis of no treatment effect, beneficial or harmful. Commonly used levels of quantitative significance include probabilities of 0.05, 0.01, 0.001, 0.0001, etc. Quantitative significance for both methods differ from clinical or personal significance. Section 3.2.2 introduced how the specified CASM platform can account for differences in the clinical significance of treatments on response variables and individual differences regarding personal or patient preferences for various and multiple treatment effects.

The methods and systems that the specified CASM platform uses to estimate the quantitative significance of temporal-interaction scores for individual CAS are related to permutation tests that the discipline of statistics uses for groups, samples, and populations of individuals. Temporal-interaction scores include benefit-and-harm scores computed with the specified CASM platform. Both temporal-interaction scores and benefit-and-harm scores are expressed in bagnes as the standardized unit of measurement.

The discipline of statistics includes the use of permutation tests involving techniques such as the bootstrap, which consists of estimating population statistics by selecting samples with replacement. The jackknife uses random samples of observations to estimate standard deviations and variances.

In contrast, as to the bootstrap and jackknife, the specified CASM platform estimates quantitative significance by permuting the temporal order of action variable levels in one or more time series for one individual. This specified approach builds on the information advantage of measurements in a time series being in temporal order as this information advantage was presented in Section 4.1. It is easier to understand the plot of a real action movie when the frames are shown in temporal order than when the frames are shown in random order.

4.11. Step 11; Apply Results to Said Complex Adaptive System:

Measurement helps solve basic and applied science and commerce problems. The specified CASM platform can help close the enormous gap between what is being achieved and what can be achieved in basic and applied sciences of CAS. SI provides a solid foundation with both basic and derived standardized units of measurement. Sophisticated mathematical and statistical tools use such measures to create theoretical models. The specified CASM platform helps bring high-performance computing and communications infrastructure to bear on knowing and problem-solving tasks.

Nevertheless, all too often, independent action variables such as drug doses are being studied as categorical variables. All too often, dependent action variables such as signs and symptoms of disease are being studied with baseline-to-endpoint change scores-when patients are still alive. All too often, experiments such as GAS RCTs designs are limited to using data snapshots instead of data movies. Data movies can provide orders of magnitude more information needed to know and manage how CAS work as 'work' as operationally defined in FIG. 1A.

More specifically, time often is measured accurately with high precision. Sensors and modern monitoring and dispensing devices yield multivariate time series datasets about action variables that interact over time. However, amounts of evidence for the temporal interactions themselves remain to be measured with universally standardized measurement units. The specified CASM platform quantifies evidence for temporal interactions with the bagne being a universally standardized measurement unit, as explained in Sections 4.8. and 12.6.

The specified CASM platform does apply to multivariate time series data about individual CAS. As such, results apply most directly to the individual complex adaptive system being studied. However, as previously stated in Section 2, universally standardized measures of temporal interaction from a plurality of persons or other CAS are suitable for statistical aggregation, statistical modeling, statistical analysis, and statistical inference from samples of individual CAS to populations.

The specified CASM platform helps supply the missing link between data collection and value as for the health sciences value chain.

5. Quantifying Evidence for Temporal Interactions; A Measurement Imperative

This section offers two potentially paradigmatic examples of why quantifying temporal interactions with the specified CASM platform is a measurement imperative. The specified CASM platform offers to help extend scientific precision and veracity (truthfulness) from systems that are not complex and adaptive to basic and applied sciences of CAS. Extending precision, veracity, and productivity with the specified CASM platform is imperative when there is a need to accelerate scientific knowledge of the workings—internal function, response, and agency—of CAS as these components of work are operationally defined in FIG. 1A.

FIG. 1A, exemplified by living persons with brains, includes how quantitative knowledge about temporal interactions is vital to understanding differences between being healthy and working well; being disordered, diseased, and not working well; and being dead and not working at all. The specified CASM platform is a measurement imperative as to advance from precision medicine to EBM-2G. Unlike the prevailing physical sciences, mathematics-and-statistics-to-SI-units-approach to precision medicine, EBM-2G would also apply the specified CASM platform to address scientifically the complex adaptive systematicity of living systems in addition to their physicality.

Examples in this section demonstrate how and the extent to which it is not feasible to achieve the required knowledge about the workings of CAS by what this disclosure identifies as the math-to-SI-units science paradigm. This paradigm is characterized by applying mathematics, including statistics, to measurements of action variable nodes as nodes are quantified with SI units of measurement. Furthermore, the math-to-SI-units science paradigm, prevailing study designs, and other extant quantitative methods appear to be limited in their capabilities to account for the six components of complex adaptive systematicity introduced in Section 6. In contrast, the specified CASM platform computes universally standardized temporal-interaction scores from multivariate time series, as summarized with eleven steps in Section 4. According to this disclosure, measurement of temporal interactions is imperative to accelerate the pace of scientific advancement from physics and chemistry to basic and applied sciences of CAS. Measurement of 'what is' with the specified CASM platform often is an alternative when it is not feasible or possible to model 'what might be' regarding the temporal workings and mechanisms of individual CAS.

The first example is about advancing beyond levels of two or more potential action variable interactants—signaling proteins, more specifically for this example—at only one or a few sporadic points in time (data snapshots) to actual quantification of evidence for temporal interactions between and among the potential interactants computed by applying the specified CASM platform to multivariate time series (data movies). Concentrations or levels of proteins and other molecules at one or a few sporadic points in time, such as clinical visits, can serve as risk factors for major untoward health events such as heart attack, stroke, and death. However, concentrations and levels say little about how a living system works as operationally defined in FIG. 1A. This first example leads to the specified CASM platform being an increasingly technically feasible alternative and complement to an otherwise if not utterly impossible task of knowing CAS with the math-to-SI-units science paradigm.

The second example is exemplified by clinical trials conducted to evaluate drug safety and effectiveness. Current gold-standard RCT designs use cross-sectional—across subjects—designs to assess evidence for causality. For this second example, every patient benefits from treatment. However, cross-sectional designs' capability to detect the actual treatment effect depends on how baseline hormone levels are ordered across patients. With one such ordering, cross-sectional methods yield valid results. Cross-sectional study designs deliver no evidence for a treatment effect under another feasible arrangement of baseline hormone levels—an invalid or false-negative result.

In contrast, benefit-and-harm scores computed with the specified CASM platform enable within-patient EBM-2G RCT designs that yield valid results for each patient for both orderings of baseline hormone levels. For example, a drug could be found to be not efficacious for a group or population when it is, in fact, highly efficacious for each person. It appears as if current gold standard RCT designs can yield false-negative results for a reason unrelated to a lack of statistical power to detect clinically significant effects.

Across-subjects study designs assess evidence for causality with statistical measures of central tendency and dispersion. Assessing evidence for causality with group-average differences can yield false-negative results. In contrast, computing temporal-interaction scores, including benefit-and-harm scores, with the specified CASM platform would deliver valid results and accelerate progress.

Some yet undetermined proportion of GAS RCTs may fail to detect real treatment effects that the specified CASM platform would detect and quantify. False-negative clinical trial results—failures to detect real treatment effects—could be an important source of lost opportunity costs for the pharmaceutical industry, investors, patients, and other stakeholders. The specified CASM platform can help avoid false-negative results by enabling longitudinal study designs that quantify evidence for causality for each person, as distinct from across subjects with cross-sectional study designs. Within-in person assessments of causality, as different from cross-sectional assessments of causality, are often feasible when both independent or treatment and dependent or response variables can be studied as action variables distinct from categorical variables. Section 7 of this disclosure introduces EBM-2G RCT designs enabled by the specified CASM platform. EBM-2G RCT designs have multiple advantages, including avoidance of false-negative results The following two examples illustrate two different paradigms for basic and applied sciences of CAS—with and without measurement of evidence for temporal interactions with the specified CASM platform.

5.1. Extend Precision and Veracity to CAS Sciences with the Specified CASM Platform:

The math-to-SI-units science paradigm achieves precision for systems that are not complex and adaptive by applying mathematics and statistics to fundamental and derived SI units of measurement that quantify physical properties. Mathematical formulae and models often quantify interactions, relationships, and dependencies between and among physical quantities expressed with SI units of measurement.

Many efforts to make medicine more precise operate primarily at the molecular level with SI units of measurement. For example, systems biology has enormous potential. However, this potential is limited to the extent that systems biology focuses on omic action variables levels without measuring temporal interactions per se. Examples of omic action variables include transcripts, proteins, metabolites, glycomes, and lipids.

Omic action variables can be monitored as nodes, as generally described in FIG. 1A and FIG. 2. There is a distinction between genetic characteristics used to identify and distinguish individuals from action variables involved in how individual CAS work in the time dimension.

By way of a non-limiting example, let N represent the number of subjects in a study. The big-N approach to gaining the power needed to identify genomic predictors of disease as for the All of Us Research Program appears to be an extension of the big-N approach to achieving statistical significance in GAS RCTs. The big-N approach often depends on investigating many people as expensive subjects. Many subjects can achieve statistical significance at an excessive cost. One risk of the big-N approach is that it could identify predictors and achieve statistical significance for effects too small to be of clinical significance. Section 7.4 of this disclosure includes demonstrating how the specified CASM platform often makes it possible to gain predictive power and statistical significance by increasing the number of repeated measurements of action variables for each person as distinct from increasing the number of subjects or persons. Section 6 of this disclosure introduces how the specified CASM platform helps account for six components of complex adaptive systematicity, including the importance of individual differences.

FIG. 2 is an example diagram 200 representing temporal or longitudinal node-edge magnitude independence for an individual complex adaptive system. FIG. 2 illustrates what this disclosure holds to be a technical problem limiting the math-to-SI-units science paradigm's ability to extend precision, veracity, and productivity from systems, including planetary systems and complicated systems, that are not complex and adaptive to the workings of CAS. FIG. 1A illustrated work 100 as to how living brains and persons function internally (e.g., function 102), respond to their environments (e.g., response 104), and act as agents (e.g., agency 106). FIG. 2 uses the same node-edge graph descriptors used in FIG. 1A. Both figures include time-dependent mechanisms by which CAS work, such as differentiating multiple mechanisms by which a person can become hypertensive, diabetic, or clinically depressed.

In contrast to nodes for independent variables 202 and dependent variables 204 being mathematically related as they are with the math-to-SI-units science paradigm, FIG. 2 represents temporal or longitudinal node-edge magnitude independence for an individual complex adaptive system such as a person, a dyad, or a brain. Longitudinal node-edge magnitude independence is far more characteristic of persons and brains than planetary systems, aircraft, and electromechanical devices. Comparatively, longitudinal node-edge magnitude independence has made the workings of CAS challenging to know, explain, predict, manage, and control with the math-to-SI-units science paradigm that does not explicitly use metrology to quantify evidence for temporal interactions. The specified CASM platform helps address the need to know, explain, predict, manage, and control how CAS work with universally standardized temporal-interaction scores that help account for longitudinal node-edge magnitude independence. Complex adaptive systematicity is a manifestation of longitudinal node-edge magnitude independence.

FIG. 2 illustrates how temporal-interaction score magnitudes for both positive (excitatory) and negative (inhibitory) edges, shown by arrows (e.g., arrow 206, arrow 208, arrow 210, arrow 212, arrow 214, and arrow 216) to indicate causality, can be mostly independent of action variable levels or magnitudes represented as nodes and shown by circles (e.g., circle 218 and circle 220 between arrow 206). Circle size represents node magnitudes. Arrow-line width represents magnitudes of temporal-interaction edges. Since each node represents a time series, node size represents some average level, such as the mean, across all repeated measurements in a time series. The absence of an arrow between two nodes in FIG. 2 indicates no temporal interaction. For simplicity, FIG. 2 shows three levels of both temporal interaction and node magnitude. For example, three different sized nodes (e.g., circles) are shown to indicate node magnitude. That is, the six nodes (e.g., circles) within bracket 222 are a first size to indicate a first level. Similarly, the six nodes (e.g., circles) within bracket 224 are a second size to indicate a second level. In addition, the six nodes (e.g., circles) within bracket 226 are a third size to indicate a third level. In a similar fashion, three different arrow sizes are depicted to indicate a different level of temporal interaction. In particular, arrows 206 and 214 are a first size representing a first level of temporal interaction. Similarly, arrows 210 is a second size representing a second level of temporal interaction. Finally, arrows 208 and 212, and 216 are a third size representing a third level of temporal interaction. Innumerable additional magnitudes for both nodes and edges typify the workings and mechanisms of CAS.

A familiar example illustrates the meaning of longitudinal node-edge magnitude independence. Consider two people in need to communicate by speaking and listening, as a dyad comprised of two interacting persons but the dyad functioning and studied as one complex adaptive system. Let each person be a node (e.g., node 115 of FIG. 1A). Let the effectiveness of spoken communication (e.g., getting a message through, being understood, effective signaling) regarding loudness of speech and hearing sensitivity be an edge between the two people in the dyad. Loud speech can overcome poor hearing. Sensitive hearing can hear faint speech. Innumerable combinations of speech loudness and hearing sensitivity can result in the same level of effective or ineffective communication or signaling.

A fundamental problem of knowing CAS, illustrated by FIG. 2, is that the math-to-SI-units science paradigm appears not to be adequate to the extent that there is longitudinal node-edge magnitude independence. The temporal interaction between the nodes cannot be known adequately by deriving a mathematical formula that relates node levels in the manner that gravitational attraction can be known, even when action variable node magnitudes are expressed in SI units of measurement. In summary, sciences for entities that are not complex and adaptive can advance very well by measuring nodes and relating them mathematically and statistically. In contrast, the math-to-SI-units science paradigm appears to be impeded to the extent that CAS manifest longitudinal node-edge magnitude independence. The specified CASM platform addresses this limitation and deficiency with universally standardized temporal-interaction scores (Sections 4.8 and 12.6) capable of accounting for complex adaptive systematicity (Section 6).

The longitudinal node-edge magnitude independence depicted in FIG. 2 has critical applications for living CAS because living systems are replete with messaging, communication, and signaling systems. These include cell signaling, nervous system signaling, and hormonal signaling. Regulatory control systems use signaling to help maintain homeostasis as necessary for survival.

Nodes, as illustrated in FIGS. 1A and 2, include effectors and receptors that interact in the time dimension. Many diseases and disorders such as cancer, autoimmunity, and diabetes involve cell signaling. Type 2 diabetes develops when insulin, a signaling molecule, is present, but receptors in muscle and brain lack insulin sensitivity. Individual brains can be studied as signal processing systems with inputs 118 and outputs 120. Normal mental and physical function and neuropsychiatric disorders involve nervous system signaling. Ordered and disordered reproductive cycles exemplify hormonal signaling.

As described elsewhere herein, capabilities of the math-to-SI-units science paradigm appear to be limited as for living systems to the extent that individual CAS manifest longitudinal node-edge magnitude independence (FIG. 2). In contrast, the specified CASM platform provides a technical solution to overcome a technical problem such as in the field of disease management and diagnosis. The technical solution overcomes the long neglected or ignored longitudinal node-edge magnitude independence to gain actionable scientific knowledge about health and disease.

For example, protein-protein signaling interactions in the time dimension exemplify multiple sources of longitudinal node-edge magnitude independence. The node size in FIG. 2 could represent protein concentrations and arrows, or lack of arrows, mean excitatory or inhibitory protein-protein signaling. Quantitative knowledge of protein-protein temporal interactions is essential to basic and applied sciences of living systems. However, longitudinal node-edge magnitude independence makes knowing the interaction between protein A and protein B far more challenging than assessing and accounting for gravitational attraction to travel from the Earth to its moon and back.

Two broad classes of protein-protein interaction network assessment methods can be compared regarding their ability to help clinicians and other stakeholders make actionable near-real-time decisions to prevent, diagnose, and treat persons subject to chronic health disorders and disease. Other stakeholders include the pharmaceutical industry and the members of the quantified-self community.

One broad approach, exemplified above for protein-protein interaction networks, is the math-to-SI-units science paradigm. Much of systems biology has been comprised of efforts to predict and explain biology with physics and chemistry and without quantifying evidence for temporal interactions per se. The math-to-SI units science paradigm includes quantifying physical contacts between and among proteins. This physical-contact approach involves investigating protein-protein interactions in terms of, as examples, electrostatic forces, hydrogen bonding, and the hydrophobic effect.

The math-to-SI-units science paradigm is of immense value for molecular engineering and other physics and chemistry-based strategies to develop drugs for improving health and other desired outcomes. However, the math-to-SI-units science paradigm would have to account for many factors—genetic differences, protein folding, post-translational modifications, and the combinatorial explosion of these factors, and temporal factors—to be of high clinical utility. Accounting for all this is what Section 5 identified as a nearly if not completely impossible task.

In contrast to the math-to-SI-units science paradigm for quantifying interactions, the specified CASM platform offers a distinct and potentially complementary approach to quantifying temporal interactions. FIG. 1A offers an operational definition of how patients and other CAS work (function internally, respond, and act as agents) in the time dimension. Chronic disorders typically are disorders of internal function that need to be diagnosed more adequately. Treatment evaluation is of response. Clinicians exemplify agents.

To be adequate for clinicians needing to make near-real-time decisions about diagnosis and treatment of individual patients in a manner that accelerates the pace of progress toward proposed EBM-2G study designs and quantitative methods should account for:

1. Temporal phenomena that include episodes of independent and dependent events, delay of effect, the effect persistence, nested time series, Boolean independent events, and Boolean dependent events (Sections 4.5 and 12.3).

2. Longitudinal node-edge magnitude independence, as portrayed in FIG. 2.

3. The six components of complex adaptive systematicity identified in Section 6. These are the importance of individual differences, complexity, adaptivity, non-linearity, stochasticity, and emergence.

4. The quantitative significance of temporal-interaction scores, including benefit-and-harm scores that quantify evidence of safety and effectiveness of treatments to help prevent and manage chronic disorders. Sections 7.4 and 12.8 present how the specified CASM platform estimates quantitative significance.

The specified CASM platform can help medicine measure its way to precision, veracity, and better outcomes at a lower cost.

The specified CASM platform offers to extend the math-to-SI-units science paradigm to the extent that it is feasible to collect multivariate time series data for action variable nodes. Vast quantities of multivariate time series data about individual CAS wait for adequate processing with the specified CASM platform. Examples include data from intensive care patient monitoring, functional brain imaging, gene expression monitoring, and metabolite monitoring. Functional brain imaging data includes data from the Human Connectome Project (http://www.humanconnectomeproject.org/data/).

The second broad class of approaches to assess protein-protein and other temporal-interaction networks is time-series methods other than CASM. Time-series methods are being applied to assess cell cycle control with gene expression data. Gene expression, in turn, guides protein formation. The specified CASM platform is a multivariate time series method.

Various time-series methods have been proposed and applied to time-series data. These include the use of correlation coefficients, measures of mutual information, and variations of Granger causality. All such methods need to be compared to the specified CASM platform's capabilities regarding their capabilities to account for the four items identified above.

FIG. 2 illustrates a distinction between activity levels, portrayed by node size, and levels of interactivity (temporal interaction), portrayed by linewidth. Representing node magnitudes can be captured by measurement at one or more points in time. However, protein concentrations are action variables (Section 1) for CAS in a manner and to an extent that masses are not. Action variables for CAS appear to manifest a far higher degree of longitudinal node-edge magnitude independence, as portrayed in FIG. 2, than systems that are not complex and adaptive. Accordingly, temporal interactions between proteins cannot be captured with mathematical formulae to the extent that CAS manifest longitudinal node-edge magnitude independence.

Longitudinal node-edge magnitude independence (FIG. 2) tends to make the workings (FIG. 1A) of CAS intractable by applying mathematics to SI units of measurement.

Nevertheless, there is a need for quantitative knowledge about how CAS work. The specified CASM platform offers to help supply the required quantitative knowledge by computing universally standardized (Sections 4.8 and 12.6) temporal-interaction scores from multivariate time series (data movies, Section 4.1) collected in the time dimension.

This disclosure takes temporal interactions in CAS to be facts of nature that need to be accounted for scientifically. Measurement of temporal interactions with the specified CASM platform offers to help make temporal interactions mathematically tractable much as SI units of mass and distance help make gravitational attraction mathematically tractable. The specified CASM platform offers new measures to model, explain, and predict with mathematics and statistics. The specified CASM platform has the potential to extend the import and value of mathematics and statistics (Section 3.5). Measurement of edges has the potential to improve basic and applied sciences of CAS as much as the measurement of nodes.

The following example illustrates that the specified CASM platform can help account for longitudinal node-edge magnitude independence, while the math-to-SI-units science paradigm does not. Adding to the masses of planetary bodies increases their gravitational attraction-direct dependence that has been expressed with the precision of a mathematical formula. In contrast, adding a constant to all measurements in one or more action variable time series does not affect the temporal-interaction scores, including benefit-and-harm scores, computed with the specified CASM platform. Longitudinal node-edge magnitude independence does not mean that there is no temporal interaction as between signaling proteins. It just means that the temporal interaction cannot be captured in a mathematical formula involving signaling protein concentrations. The way out of this dilemma is to quantify evidence for temporal interactions with the specified CASM platform.

Returning to the hearing example presented earlier in this section: Accurate communication can be more critical than the loudness of voice and hearing sensitivity. The specified CASM platform helps quantify evidence for effective signaling and signal transduction. The measurement of nodes is not sufficient. Precision medicine focuses on identifying variables and molecular nodes. EBM-2G would help capitalize on genomics by measuring how living systems work (FIG. 1A) to account for longitudinal node-edge magnitude independence (FIG. 2). Capitalizing on genomics includes computation of EBM-2G quantitative temporal-interaction phenotypes and tests (Section 9) needed to accelerate genotype-phenotype mapping.

The specified CASM platform quantifies evidence for temporal interactions that exist. However, such temporal interactions often are not adequately accounted for in a sufficiently practical manner, by physics and chemistry laws.

The problem of longitudinal node-edge magnitude independence has been exemplified primarily for protein-protein signaling interactions for living systems when diagnosing chronic disorders of internal function (FIG. 1A). A related problem appears to exist for treatment evaluation of response. FIG. 1A includes definition of response.

5.2. Avoid False-Negative Clinical Trial Results:

Advances in biomedical sciences and drug development often must be found safe and efficacious in clinical trials before they can be marketed, prescribed, and consumed to improve the human condition. Clinical trials often evaluate response (FIG. 1A). The example of false-negative clinical trial results included in this section is offered as applying to evaluations of drugs indicated to prevent and manage chronic health disorders, diseases, and related health conditions that affect length and quality of life.

The current gold standard RCT design for drug development, regulatory marketing approval, and EBM assesses the evidence for causality using cross-sectional study designs and quantitative methods. For example, a cross-sectional placebo controlled RCT could randomize subjects to a placebo (dose zero) group and one or more non-zero dose groups. A primary response variable for hypothesis testing often is assessed at both baseline and endpoint for each subject. Then a null hypothesis of no treatment effect could be tested with statistical measures of group central tendency and dispersion. Rejection of the null hypothesis in the toward or favorable direction would support the conclusion that the drug is efficacious.

False-negative results could occur if the RCT was under-powered—had too few subjects to detect a clinically significant treatment effect. False-negative RCT results—not demonstrating that a drug is efficacious when it is, in fact, efficacious—are failures as when patients are awaiting cures and investors are awaiting returns. The example in this section is about an entirely different reason why current gold standard RCT designs might be failing to detect clinically significant treatment effects.

FIG. 3B identifies a set of conditions under which current gold-standard cross-sectional GAS RCT designs (Section 2) might be failing to detect within-patient treatment effects that are clinically significant. Furthermore, it appears that conventional gold standard cross-sectional RCT designs often can create unnecessary and avoidable conflicts for clinicians about what source of evidence to trust and accept while making decisions about the ongoing care of individual patients with complex and heterogeneous chronic disorders. Clinicians can be encouraged to practice scientific medicine by acting according to conventional EBM treatment guidelines based on conventional cross-sectional RCT designs. However, clinicians often manage patients in accord with longitudinal evidence gained while providing care to individual patients. For example, clinicians can informally monitor and evaluate evidence for safety and effectiveness for individual patients over a time series of adjustments in both types and doses of treatment. These two sources of evidence can support different decisions about how individual patients should be treated. In contrast, the specified CASM platform offers to help make medicine more scientific and cost-effective by increasing and strengthening longitudinal evidence for safety and effectiveness.

FIG. 3A and FIG. 3B use hypothetical data 300 for nine patients to illustrate a fundamental problem. In a non-limiting example, let both plasma estradiol concentrations and the quality-of-life response variables be assessed at both baseline and endpoint for each patient. Let the higher quality of life scores be toward or beneficial. Let estradiol concentrations include both endogenous and exogenous estradiol combined. Notice that both FIGS. 3A-3B show that supplemental estradiol doubled both estradiol concentrations and quality of life response variable levels for each patient. Hormone supplementation benefited each patient as a ground truth fact.

At issue are the relative capabilities of two categories of quantitative methods and systems to correctly identify and account for the ground-truth fact that supplemental estradiol was beneficial for each patient in FIG. 3A and FIG. 3B. FIG. 3A and FIG. 3B compare results obtained with two quantitative methods and systems.

FIG. 3A: Both cross-sectional, across patients, quantitative methods and systems used by conventional gold standard RCT designs and longitudinal, within-patient, methods and systems enabled by CASM yield correct results.

FIG. 3B: Only longitudinal, within-patients, quantitative methods and systems enabled by the specified CASM platform and quantifying evidence for benefit and harm (safety and effectiveness) with universally standardized scores quantifying evidence for temporal interactions between treatment and health action variables yield correct results. In contrast, conventional cross-sectional methods and systems fail to yield correct results. Obtaining the correct result includes avoiding false-negative results—concluding that treatment was not efficacious when, in fact, the treatment was efficacious.

FIGS. 3A and 3B show the same numbers. The only difference at baseline is how the quality-of-life response variable data are ordered. For FIG. 3A, all three patients with estradiol concentrations of 1 at baseline had a quality-of-life response-action-variable level 5, all three with concentration 2 had a response-action-variable level 10, and all three with concentration 3 had a response-action-variable level 15. The response variable level was directly dependent upon estradiol concentration. Under this condition, all four cross-sectional scatter plots 302, 304, 306, and 308 in FIG. 3A involving estradiol concentrations, response variable levels, changes in concentrations, changes in response variable levels, average concentrations, and average response variable levels correctly show perfect linear relationships.

The benefit-and-harm score for each patient shown in the top portion of FIG. 3A is 1. When there are only two repeated measurements, the maximum magnitude for a temporal-interaction score, including a benefit-and-harm score, is 1. A positive score quantifies evidence of benefit. A negative score quantifies evidence of harm. The only possible score would be 0 when there is no change in treatment or response action variable levels. The magnitudes of temporal-interaction scores, including benefit-and-harm scores, could increase indefinitely with more repeated measurements. The benefit-and-harm scores in FIG. 3A correctly quantify evidence for the ground-truth fact that estradiol supplementation was associated with improved quality of life for each patient. Note that the preceding sentence says associated and not caused because no randomized experimental control was exercised for the data in FIG. 3A and FIG. 3B. Section 7 about EBM-2G RCT designs adds within-person or longitudinal randomized experimental control of doses in the time dimension to ensure that benefit-and-harm scores are valid.

As shown in FIG. 3B, the numbers are the same at baseline as in FIG. 3A. The only difference at baseline is that each of the three patients at a given dose experienced each of the three quality of life response action variable levels. In other words, estradiol concentrations and response variable levels were completely independent at baseline. Such independence is not unreasonable because of longitudinal node-edge magnitude independence (FIG. 2). Patients with the same estradiol concentrations could experience different quality of life levels. Under this condition of independence and unlike the scatter plots in FIG. 3A, none of the cross-sectional scatter plots 310, 312, 314, 316 in FIG. 3B indicates the ground-truth-fact treatment effect.

In contrast to the scatter plot results for FIG. 3A, the scatter plot results of FIG. 3B show no evidence for the treatment effect—that the doubling of estradiol level doubled the quality-of-life score for each patient. All these cross-sectional scatter plot results show false-negative results. In contrast, all the benefit-and-harm scores for both FIGS. 3A and 3B have values of 1. The within-persons benefit-and-harm scores are correct regardless of how the estradiol concentrations and quality of life response variable levels were paired at baseline in FIG. 3.

There appears to be no way of knowing how many RCTs conducted since 1948 might have yielded false-negative results. Clinicians and other stakeholders have yet to have ready access to the specified CASM platform software to quantify evidence for the safety and effectiveness of treatments and other exposures for individual patients and other persons.

Note the paradox that Section 2 of this disclosure appears to expose. Clinicians often use longitudinal methods to assess treatment effects and manage patients with difficult-to-control chronic disorders and diseases-typically without systematically collecting and processing time-ordered data about treatment and health. For example, clinicians often start treatments, adjust doses, and stop treatments according to ongoing subjective judgments about the safety and effectiveness of treatments for their individual patients. Apparently, as part of an effort to become more scientific, clinicians and other stakeholders have largely embraced conventional GAS RCT designs (Section 2) capable of yielding false-negative results (FIG. 3B) and other problems. How often might clinicians have been correct with their informal methods and subjective judgments about individual patients? In contrast, formal methods, including current gold standard RCTs, can yield invalid results for individual patients. Furthermore, it is widely accepted that longitudinal evidence for individual patients can trump GAS RCT results such as when longitudinal evidence indicates that a patient is having a serious adverse reaction to an approved treatment, calling for treatment to stop or change.

The specified CASM platform offers clinicians a chance to be better clinicians, mainly by doing what they already do, only more scientifically. Both clinicians and EBM-2G would do more to evaluate treatment effects for individual patients longitudinally with the same study designs and quantitative methods. Both clinicians and EBM-2G would put individual patients first.

The scatter plots 302-308 of FIG. 3A are valid indicators of the beneficial treatment effect. In contrast, the scatter plots at the bottom of FIG. 3B are invalid even though they use the same cross-sectional methods as FIG. 3A. Hormone supplementation doubled quality of life scores for all patients in both FIGS. 3A and 3B. In contrast to the cross-sectional methods used for the scatter plots, the specified CASM platform that embodies longitudinal methods provided valid results for all patients in FIG. 3A. FIG. 3B suggests that conventional gold standard RCT designs can yield false-negative results. As such, FIG. 3B illustrates one way that RCTs can fail. Section 5.5 identifies cultural barriers to quantifying evidence for safety and effectiveness before statistical aggregation, modeling, and inference from samples to populations. However, there appears to be little or no recognition that (a) RCTs needing to evaluate safety and effectiveness and (b) could measure and test safety and effectiveness (c) should measure and test safety and effectiveness as with the specified CASM platform.

Together, FIGS. 2, 3A and 3B portray two of many ways longitudinal science with the specified CASM platform can be more rigorously scientific than cross-sectional science when there is a need to know, predict, and manage CAS.

Current parallel-group or cross-sectional RCT designs represent group-average science (GAS), as introduced in Section 2 of this disclosure. GAS provides group-average results that need not apply to any individual. Conceivably, clinicians and other decision-makers could improve health and lower costs when armed with more multivariate time series data and the specified CASM platform.

In contrast to current GAS RCT designs, Section 7 presents core principles of EBM-2G RCT designs, enabled by the specified CASM platform. EBM-2G RCT designs offer to avoid false-negative RCT results, account for the fact that patients and other persons are CAS, integrate safety and effectiveness evaluations, dramatically increase power to detect real treatment effects, help integrate clinical research with clinical practice, improve scientific reproducibility, and reduce costs. Section 6 addresses complex adaptive systematicity. Section 7.4 includes demonstrating how the specified CASM platform uses information from larger numbers of repeated measurements to increase statistical significance for populations.

5.3. Advancing to Second Generation Evidence-Based Medicine (EBM-2G):

This disclosure coined 'second generation evidence-based medicine' (EBM-2G) at the beginning of Section 2 as a successor to precision medicine and its predecessors. EBM-2G is about gaining precision, veracity, and productivity by expanding the scientific evidence base for medicine and medical decision-making. More specifically, EBM-2G offers to fill a "lacuna" comprised of medicine needing to account scientifically for the complex adaptive systematicity of personhood (Section 6) by overcoming longitudinal node-edge magnitude independence (FIG. 2) and risk of false-negative clinical trial results (FIG. 3B). The specified CASM platform offers to advance EBM-2G with EBM-2G RCT designs (Section 7), EBM-2G health-effects monitoring (Section 8), and EBM-2G quantitative temporal-interaction phenotypes and phenotype tests (Section 9).

5.4. Extending Precision Medicine for Oncology to EBM-2G as for Neurology and Psychiatry:

EBM-2G quantitative temporal-interaction phenotypes and phenotype tests need to be studied especially for their potential to extend precision medicine from cancer to EBM-2G for neuropsychiatric disorders in addition to cancer. Progress toward precision oncology appears to have been faster than progress toward precision neurology and precision psychiatry. Though illustrated in the context of neuropsychiatric disorders, the same points often apply to other chronic disorders and diseases.

The CASM platform described herein can be used to distinguish problems that arise from differences in any potential inherent difficulties of the subject matters (e.g., oncology versus neurology versus psychiatry) from problems derived from limitations and deficiencies of study designs and quantitative methods that investigators bring to bear on their respective subject matters. For example, oncology has a history of addressing real endpoints such as death as for survival analysis. Survival time is important. However, investigators in neurology and psychiatry create reliability and validity problems when defining artificial endpoints on response action variables such as pain and depression rating scale scores. Levels of pain and depression are apt to fluctuate day-by-day, week-by-week. In contrast, going from being alive to being dead is a one-way passage to a real endpoint. Artificial endpoints, created to fit the limited capabilities of statistics and GAS RCT designs, are counterproductive because they limit the number of repeated measurements that can be used to increase the reliability of evaluating treatment effects.

Similarly, the discipline of statistics is far more suitable for categorical independent variables than independent action variables. A person having or not having a total prostatectomy or bilateral oophorectomy as for cancer treatment is a real categorical independent variable. Investigators create problems as when drug dose, which can change and be randomized longitudinally in the time dimension, is studied as a categorical independent variable instead of an independent action variable.

Cancer is becoming more of a manageable disease as both independent action variables such as drug doses or levels of other biologically active molecules and response action variables such as circulating tumor cells or circulating DNA can be studied as response action variables and processed with the specified CASM platform. Differential effects on survival times could be used to set directionality (i.e., toward, or beneficial and untoward, or harmful) and importance weights for multiple dependent response action variables.

5.4.1. Advancing Diagnoses for Neuropsychiatric Disorders:

The problem of longitudinal node-edge magnitude independence portrayed in FIG. 2 applies to all three of these disciplines. However, this problem appears to be exacerbated as one moves from oncology to neurology and psychiatry. Reasons for longitudinal node-edge magnitude independence were exemplified above by how genetic differences, protein folding, and protein post-translational modifications appear to contribute to longitudinal node-edge magnitude independence. Such reasons, illustrated with proteins, apply to all three disciplines. For example, neurotransmitter systems (e.g., cholinergic, glutamatergic, serotonergic, dopaminergic, histaminergic) involve signaling proteins and receptor proteins. However, moving from this molecular level to an electrophysiological level appears to offer additional causes of longitudinal node-edge magnitude independence.

Let each node for the within-person portion of FIG. 1A be a neuron, brain voxel in functional brain imaging, or a brain region. Longitudinal node-edge magnitude independence, which can vary by degree, derives from the fact that activity of each neuron, brain voxel, or a brain region can be affected by hundreds or thousands of time-dependent excitatory and inhibitory inputs from other neurons, brain voxels, or brain regions. Furthermore, conditioning, learning, and other forms of adaptation can affect degrees of independence. Longitudinal node-edge magnitude independence could be expected to increase as one moves from molecules to behaviors, moods, and cognition, as suggested by mind over body.

The specified CASM platform would have the potential to accelerate the pace of progress in precision neurology and precision psychiatry beyond the rate of improvement in precision oncology. There appears to be more available or readily available multivariate time series data about brains than for precision oncology. The storehouse or backlog of multivariate time series data from functional brain imaging in the Human Connectome Project database exceeds the amount of multivariate time series about gene expression and protein levels, especially for human data. As mentioned in Section 2 and addressed more fully in Section 6.4, non-linearity is a complex adaptive systematicity component. Nevertheless, investigators are still using correlation coefficients to process multivariate time series functional brain imaging data. Correlation coefficients are suitable for assessing cross-sectional linear 'interactions' as between height and weight with pairs of measurements that are independent because of being collected from different individuals. In contrast, correlation coefficients are unsuitable for processing multivariate time series from brains. Brains epitomize CAS.

5.4.2. Advancing Treatment Evaluation as for Neuropsychiatric Disorders:

Evaluations of antidepressants epitomize limitations and deficiencies of GAS RCT designs compared with the EBM-2G RCT designs. EBM-2G RCT designs (Section 7) avoid false-negative results (FIG. 3B) and help account for the complex adaptive systematicity of personhood (Section 6).

Let a GAS RCT design for an antidepressant have one placebo group and one active treatment group being used to test a null-hypothesis of no beneficial treatment effect on one primary response variable assessed at both baseline and endpoint. Such GAS RCTs can provide helpful information at the population level, especially if the RCT sample is a random sample of a well-defined population. However, GAS RCTs typically use convenience samples, not random samples.

Also, GAS RCTs that embody the one-size-does-not-fit-all problem provide very little information about how anyone responded in the RCT or how any other individual patient in the target population would respond. Low informativeness about individual response is problematic because clinician decision-makers treat patients one by one, not populations. Clinicians need rigorous scientific information that applies to the individual patients whom they diagnose and treat. The specified CASM platform can help provide rigorous scientific knowledge required to treat individual patients while also accelerating population health and facilitating learning healthcare systems. Clinicians can help integrate their roles as clinicians and investigators.

Unlike GAS RCTs, EBM-2G RCTs are designed to provide results that (i) reliable, (ii) valid, (iii) comprehensive, and (iv) detailed for each person. EBM-2G RCTs treat patients as persons, not subjects. EBM-2G RCTs assess evidence for causality before statistical aggregation, analysis, and inference.

Unlike GAS RCTs, EBM-2G RCTs can provide the information needed to help target the right drug at the right safe and effective dose to the right person. EBM-2G RCTs can provide EBM-2G quantitative treatment response phenotypes required to help identify any genetic or other predictors of differential response or optimal safe and effective doses. Each of these four criteria mentioned above will be addressed briefly in turn.

5.4.2.1. Person-Specific Reliable Measures of Treatment Response:

Assessments of depression are subject to measurement error and effects of uncontrolled events and conditions such as changes in personal relationships, employment, and death as of a pet or family member. Assessments of response action variables typically are subtler and far less reliable than assessments of vital status (alive or dead) as for cancer. Baseline-to-endpoint-change-scores, often used for chronic disorder RCTs, are not reliable indicators of treatment effect to the extent of measurement error and uncontrolled variables may have affected response variable levels in addition to treatment effects. Unreliability of change scores drives up sample size requirements to detect clinically significant effects in GAS-RCTs. Large samples drive up costs, often increase sample heterogeneity, and impede targeting.

Clinical trialists who adhere to defining artificial baselines and endpoints on response action variables forego opportunities to use larger numbers of repeated measurements and the specified CASM platform to obtain reliable treatment response evaluations. The specified CASM platform can use information from many time-ordered repeated measurements to increase reliability without giving any of the repeated measurements special status as artificial baselines or artificial endpoints. Section 7.4 illustrates how more repeated measurements increase statistical significance without confounding effects of individual differences with treatment effects (Sections 3.2.2. and 5.5.).

5.4.2.2. Person-Specific Valid Measures of Treatment Response:

For decades, it has been recognized that between 30 to 40% of depressed patients respond to placebo. Less widely recognized is that GAS RCT designs do not distinguish true responders to active treatment from responders on active treatment who would have responded to a placebo. Responders to active treatment are a heterogeneous group. Heterogeneity impedes prediction and targeting.

GAS-RCTs are not designed to provide valid within-patient indicators of treatment effect. Instead, GAS-RCTs compare groups to assess causality. In contrast, EBM-2G RCTs achieve validity by using longitudinal within-patient randomization of two or more doses in the time dimension. Longitudinal dose randomization may also make it harder for patients and clinicians to break the blind in RCTs.

Clinical trialists who adhere to assessing causality by randomizing subjects to different dose groups, including placebo as dose zero, instead of randomizing two or more doses to different periods for each person, forego opportunities to obtain valid response measures for each person.

5.4.2.3. Person-Specific Comprehensive Measures of Treatment Response:

It has long been widely recognized that treatments typically have multiple beneficial and harmful effects. This fact of nature calls for tradeoffs as between experiencing pain and experiencing drowsiness and not being able to drive safely while on the drug. Nevertheless, clinical trialists typically test primary hypotheses defined on primary response variables such as pain.

Evaluating treatments as if they have only primary effects lacks scientific truthfulness and veracity. Treatment evaluations need to be comprehensive. Decision-makers choose drugs and doses, not treatment effects. Selecting a medication at a given dose can be likened to accepting a whole basket of poisons and remedies-some far more severe and critical than others. Money offers a common metric of cost and value for various goods and services, like benefit-and-harm scores.

Any one RCT does need to test one predefined primary hypothesis to avoid false-positive results and the need for Bonferroni type corrections for multiple tests. Unfortunately, the practice of defining primary hypotheses on primary response variables as in status quo GAS RCT designs extracts a terrible price. The specified CASM platform offers a choice. Safety and effectiveness can be balanced with a common metric of value, as introduced in Section 3.2.2. The specified CASM platform enables comprehensive person-specific integrated scientific evaluations of safety and effectiveness to balance benefits against harms across multitudes of response action variables.

More specifically, the specified CASM platform offers opportunities for RCTs to use just one test for testing null hypotheses about drugs being neither safe nor effective across multitudes of safety and effectiveness response action variables. Also, the specified CASM platform can estimate quantitative significance for each person (Sections 4.10 and 12.8) in EBM-2G single-person RCT designs (Section 7.1.) as well as individual and statistical significance in EBM-2G single-group, multiple single-person RCT designs (Section 7.2) and EBM-2G parallel, multiple single-group, multiple single-person RCT designs (Section 7.3). Rejection of a null hypothesis in the positive or beneficial direction would support the conclusion that benefits outweigh harms. Rejection of a null hypothesis in the negative or harmful direction would support the conclusion that harms outweigh benefits. With the specified CASM platform, such hypotheses can be tested starting at the level of each patient or other person. In turn, and as described in the next section, users of the specified CASM platform would be able to drill down to explore detailed evidence for safety and effectiveness regarding each response variable for each person. Response variable specific effects need not lose their identities when using overall benefit-and-harm scores.

The following are four overlapping advantages of defining primary hypotheses on benefit-and-harm scores regarding response action variables as distinct from defining primary hypotheses directly regarding the response variables per se.

First, the specified CASM platform allows evidence for safety and effectiveness to be integrated and balanced scientifically for response action variables starting at each person's level. In contrast, conventional evaluations of safety and effectiveness can be likened to a barter economy. For example, drug labels are apt to include information about group-average efficacy as from GAS RCTs. Treatment guidelines often are based on a meta-analysis of GAS RCT results. In contrast, safety information in drug labels is apt to include extensive lists of adverse event rates for placebo and one or more active treatment doses. Patients and drug effects are known to be heterogeneous. Decision-makers are left with between-the-ears processing of different worlds of evidence with varying scientific rigor levels and about diverse health effects. Reliance on GAS RCTs adds some modicum of scientific rigor. However, decisions about treating individual patients and consuming drugs remain mainly based on subjective impressions and clinical judgments of limited reproducibility.

Second, defining primary hypotheses on primary response variables impedes the identification of new drug indications. This convention has spawned drug rescue and re-purposing as widely exploited opportunities. However, such opportunities indicate avoidable failures in initial targeting.

Third, the specified CASM platform would enable drug developers to begin the evaluation of potential drugs with a strategy figuratively described as using a funnel properly with the broad side up. Clinical trialists could begin clinical drug evaluation programs by quantifying evidence for benefit and harm over as many safety and effectiveness response variables as feasible. Then they could use accumulating bodies of benefit-and-harm scores to learn safety and effectiveness profiles across pluralities of response variables for individual persons. This approach could be described as a learn-as-you-go approach to targeting the right drug to the right patient at the right safe and effective dose. Needing to know primary response variables in advance to design successful RCTs can be likened to using a funnel upside down. It also can be described as needing to know what one has yet to learn to be successful. Needing to know what one has yet to learn invites failure. Figuratively, good targeting begins by using a funnel broad side up, not upside down.

Fourth, the specified CASM platform offers to simplify statistical analyses for RCT designs greatly, including for EBM-2G RCTs, otherwise mostly intractable. For example, Section 7.2 introduces the single-group, multiple single-person, randomized trial design. The null hypothesis of no overall benefit and harm could be tested with a single-group t-test on the mean. This test applies even if the trial involved a plurality of longitudinally randomized doses of the same type of drug, a plurality of response action variables to evaluate safety and effectiveness, tens or hundreds of patients, and multiple weeks of daily treatment and health data as from dispensing and monitoring devices.

Clinical trialists who adhere to defining primary hypotheses on primary response variables flout common knowledge about drugs having multiple effects. They also forego opportunities of using a common metric to obtain integrated evaluations of safety and effectiveness that are comprehensive of the many ways that treatments can affect health. Section 3.2.2 of this disclosure introduce benefit-and-harm scores as a common metric to evaluate safety and effectiveness regarding pluralities of dependent action variables. The specified CASM platform offers to increase cost-effectiveness and productivity in basic and applied sciences of CAS.

5.4.2.4. Person-Specific Detailed Measures of Treatment Response:

The primary information yield from a GAS RCT for this depression example is often a statement about an average difference between a placebo group and a single-dose active treatment group in a baseline to endpoint change for a primary response variable being statistically significant. Typically, results about a few secondary hypotheses are also presented.

Clinical trialists who adhere to GAS RCT designs forego opportunities to assess the statistical significance of overall benefit-and-harm scores that evaluate safety and effectiveness across pluralities of response action variables simultaneously together with more than two doses. Also, clinical trialists forego opportunities to obtain results such as the following:

1. The quantitative significance of an overall benefit-and-harm score that assesses safety and effectiveness for each person (Sections 4.10 and 12.8.) and according to each person's preferences for various health effects,
2. A benefit-and-harm profile that summarizes evidence for safety and effectiveness regarding a multitude of response action variables for each person,
3. A group-average benefit-and-harm profile obtained by averaging the person-specific benefit-and-harm profiles,
4. Person-specific and group average graphs showing overall benefit and harm and response variable specific benefit and harm as functions of drug dose,
5. Person-specific and group-average graphs showing overall benefit and harm and response variable specific benefit and harm as functions of delay of response and persistence of response.

The information yield of EBM-2G RCT designs for both individual persons and populations can vastly exceed GAS RCT designs' information yield.

Also, EBM-2G RCT designs can have substantial practical and cost advantages, including the following.

1. EBM-2G RCT designs are especially suitable for rare disorders and diseases. More disorders and diseases are becoming rare as diagnostic specificity increases.
2. GAS RCT designs essentially require clinical trialists to know what they have yet to learn to design a successful RCT. They need to know which patients to include, which patients to exclude, what the primary response variable should be, and the optimal safe and effective dose. In contrast, EBM-2G RCTs can be ultra-adaptive as with ongoing evaluations of safety and effectiveness as functions of time and dose.
3. EBM-2G RCTs enable within-person randomized titration of optimal safe and effective dose.
4 EBM-2G RCT designs can use larger numbers of repeated measurements to increase quantitative significance for both individual patients and groups. Repeated measurements, collected with dispensing and monitoring devices, can be less expensive than recruiting large samples of unfortunate subjects.

5.4.2.5. Improve Targeting of Drugs as for Neuropsychiatric Disorders:

The early impetus for the present inventor to invent the specified CASM platform was the need for better information to target and evaluate neuropsychiatric drugs.

Many patients suffer from mixtures of anxiety and depression. Various antidepressants have different mechanisms of action, and different side effect profiles. Likewise, multiple anxiolytics have different mechanisms of action and different side effect profiles.

Depression and anxiety disorders form syndromes. According, antidepressants and anxiolytics have been evaluated in RCTs with composite rating scales. As examples, one version of the Hamilton Depression Rating Scale (HAM-D) has 17 items rated with a combination of 3-point and 5-point scales. There is a substantial overlap between the depression and anxiety composite rating scales. As examples, the HAM-D includes items for psychic and somatic anxiety. The HAM-A contains an item about depressed mood. Both scales assess insomnia. Each item in both scales can be studied as a response action variable.

Primary hypotheses in GAS RCTs typically are formulated in terms of total composite rating scale scores to avoid a multiplicity of statistical tests. A major problem that impairs targeting the right antidepressant or anxiolytic to the right patient at the right safe and effective dose is that GAS RCT designs are incapable of providing measures of treatment effect that are reliable (Section 5.4.2.1), valid (5.4.2.2), and dose-specific for each item (Section 5.4.2.4) and across all items (Section 5.4.2.3) for each patient. In contrast to GAS RCT designs, EBM-2G RCT designs can provide all of these in addition to being able to test one primary hypothesis with one statistical test in RCTs with more than one person. Also, EBM-2G RCTs can estimate CASM significance for each person (Sections 4.10 and 12.8). Use all this information to improve targeting and patient care.

5.5. Cultural Barriers to Creative Destruction and EBM-2G:

Cultural barriers to scientific and technical progress in medicine are not inherent in the subject matter under study. Instead, cultural barriers derive from methodology and methodology standards being applied to the subject matter. Cultural barriers can lead to neglect of attention to root cause scientific and technical problems that include at least five types of conflation or confounding. GAS RCTs often unnecessarily confound:

1. Effects of individual differences such as genetic differences with treatment effects (Section 2),
2. True responders to active treatment with responders on active treatment who would have responded to placebo (Section 5.4.2.2),
3. Dose with the type of treatment (Section 2),
4. Treatment effects with how they are valued (Section 3.2.2), and,
5. Artificial endpoints with real endpoints (Section 2).

Furthermore, EBM-2G would avoid problems with node-edge magnitude independence (FIG. 2), false-negative clinical trial results (FIG. 3B) and targeting problems that derive from a failure to use a common metric of benefit and harm to help evaluate safety and effectiveness.

According to this disclosure, cultural barriers include standards based on an outmoded methodology for basic and applied bioscience that can be overcome by invention, innovation, technology development, and measurement by the specified CASM platform. The following are three examples of such often-counterproductive cultural barriers and some incentives engendered by standards that have become outmoded due to advances in technology, including data collection, data processing, and communication infrastructure, together with the specified CASM platform. More specifically, the following selected standards impede creative destruction and EBM-2G.

1. The CONSORT (Consolidated Standards of Reporting Trials) statement (http://www.consort-statement.org/).
2. The United States Food and Drug Administration offers "Clinical Trials Guidance Documents" available at (https://www.fda.gov/regulatory-information/search-fda-guidance-documents/clinical-trials-guidance-documents).

3. The vision of the Patient-Centered Outcomes Research Institute is: "Patients and the public have information they can use to make decisions that reflect their desired health outcomes." Here is PCORI's mission statement: "PCORI helps people make informed healthcare decisions, and improves healthcare delivery and outcomes, by producing and promoting high-integrity, evidence-based information that comes from research guided by patients, caregivers, and the broader healthcare community" available at (https://www.pcori.org/about-us/our-vision-mission).

All three of these standards are ripe for creative destruction that includes the specified CASM platform. In contrast to all three of these standards, the specified measurement platform can help advance patient-centricity for individual patients and population research (Section 6.9).

6. Accounting for Complex Adaptive Systematicity

When applied to CAS, quantitative methods, study designs, and scientific paradigms need to be assessed and evaluated regarding their capabilities to account for complex adaptive systematicity. This disclosure has coined 'complex adaptive systematicity' to identify characteristics, taken as a set, that help distinguish CAS from entities, including complicated systems, that typically less complex and adaptive than, as examples, persons and many other living systems.

Persons and personhood personify complex adaptive systematicity. Accordingly, and by example, the specified CASM platform offers to advance EBM, based mainly on one-size-fits-all GAS RCT designs, to EBM-2G that would quantify and phenotype how individual persons work (internal function, response, agency; FIG. 1A) in the time dimension.

The specified CASM platform offers to extend SI by quantifying evidence for temporal interactions that help describe, predict, explain, and manage how individual CAS function internally, respond, and act as agents (FIG. 1A). Furthermore, the specified CASM platform quantifies temporal interactions in a manner that helps account for complex adaptive systematicity—characteristics that help distinguish CAS from entities of far lesser complex adaptive systematicity. The following six sections address why and how the specified CASM platform helps account for six manifestations of complex adaptive systematicity. These six are the importance of scientifically accounting for:

1. Individual differences,
2. Complexity,
3. Adaptivity,
4. Non-linearity,
5. Stochasticity, and
6. Emergence.

According to this disclosure, complex adaptive systematicity manifests itself not only in how an individual CAS functions internally but also to how it responds to its environment, including treatments, and how it acts as an agent on its environment, as illustrated in FIG. 1A. Quantifying evidence for temporal interactions in a manner that helps account for complex adaptive systematicity offers to advance basic and applied sciences of how CAS work in the time dimension.

As introduced in Section 2, basic and applied sciences of CAS can be described as suffering from measurement deficiency anemia. The specified CASM platform offers to help cure measurement deficiency anemia so that, for example, EBM-2G helps account for the complex adaptive systematicity of personhood. CASM helps account for complex adaptive systematicity in a manner that is not specific to type of complex adaptive system.

6.1. Individual Differences:

"One size does not fit all" continues as a problem in medicine as of the year 2021. Many such "one size does not fit all" type problems in science and commerce have been solved mainly for physical entities without complex adaptive systematicity. As examples, applications of SI units of measurement have largely solved problems of fitting shoes to feet, eyeglass prescriptions, and assembly line parts. However, despite countless claims about personalized or individualized treatments and services, the 'one size does not fit all' metaphor continues to apply to persons and other CAS. The specified CASM platform offers to mitigate substantially 'one size does not fit all' type problems for entities with complex adaptive systematicity. CASM can help users know how the world works.

The importance of individual differences appears to be the most widely recognized and popular of the six components of complex adaptive systematicity identified in Section 6. Accordingly, public presentations of antecedents to the specified CASM platform have identified portions of the specified CASM platform as the science of individuality measurement algorithm (SIMA). The specified CASM platform extends and improves upon SIMA. The specified CASM platform includes means to help address all six manifestations of complex adaptive systematicity. Persons and brains, as examples, exhibit all six manifestations of complex adaptive systematicity as real-world facts.

Furthermore, the need to account for complex adaptive systematicity, including the importance of individual differences, appears to compound as one advances from cells, organs, organ systems, to whole persons studied at biological, psychological, and social levels. The specified CASM platform offers to help overcome the limitations and deficiencies of reductionism as a scientific paradigm. For example, accounting scientifically for genetic and other molecular markers is an important beginning, but just a start, to account for complex adaptive systematicity scientifically with the specified CASM platform. In contrast to reductionism, the specified CASM platform offers to help advance robust systems science by quantifying temporal interactions, excitatory and inhibitory, in a manner that helps account for complex adaptive systematicity. For example, smartphones and other devices, such as wearables, can collect what this disclosure identifies as multivariate time series data. Section 4.1 describes how multivariate time series data can provide orders of magnitude more information than essentially cross-sectional data to understand individuals scientifically.

Section 4.3 describes how the specified CASM platform must convert each dimensional time series into a digital series set, without necessary loss of information, before computing temporal-interaction scores with the bagne being the final standardized unit of measurement (Sections 4.8, and 12.6.).

6.2. Complexity:

FIG. 2 about node-edge magnitude independence offers to understand why and to what extent knowing of parts is not enough to understand the "whole system's behavior," as shown in FIG. 1A about the tripartite definition of work. Characterizations of CAS are replete with mentions of 'interaction.' The specified CASM platform addresses interactions directly by quantifying multiparametric (Sections 4.3 and 4.4, 12.1. and 12.2) temporal-interaction patterns per se. After direct measurement by computation, temporal-interaction scores can be modeled mathematically in ways that may not be possible in modeling with SI units of measurement alone.

Also, temporal-interaction scores from two or more individuals can be aggregated, modeled, and analyzed statistically. This data-driven empirical approach contrasts with modeling how parts of CAS interact before or without quantifying evidence for the temporal interactions per se. Mathematical models of interactions in CAS, based on SI units of measurement, could be validated in terms of the extent that such models conform with measures of temporal interaction computed with the specified CASM platform.

The specified CASM platform applies when it is possible to collect multivariate time series about parts and aspects of the CAS itself and its environment. Unlike some approaches to studying CAS, the specified CASM platform does not assume that interacting parts are self-similar agents following simple rules. Parts of living systems (e.g., proteins, lipids, sugars, metabolites) are not self-similar, often interact in the time dimension, and may not follow rules.

This disclosure already has included mentions of specific capabilities to account for complexity in addition to quantifying evidence for patterns of temporal interaction between one independent action variable time series and one dependent action variable time series. As examples, benefit-and-harm scores, introduced in Section 3.2, help account for the fact, for instance, that any one type of drug almost invariably has multiple beneficial and harmful effects across pluralities of dependent or response action variable time series. Benefit and harm scores offer a common metric of value much as money is a common metric of cost.

A capability of the specified CASM platform identified as Boolean independent events (Sections 4.5 and 12.3) helps account, for example, that two or more different types of drug or other environmental exposures can have synergistic or antagonistic effects. Similarly, Boolean dependent events can help account, for example, that some diseases such as clinical depression can be studied as syndromes.

6.3. Adaptivity:

Longitudinal node-edge magnitude independence, illustrated by FIG. 2, helps allow CAS, such as persons with brains, to be adaptive in ways that complicated systems such as high-performance aircraft have yet to become. Adaptivity gives living systems resilience in the face of environmental change and perturbation. Persons can adapt to gain competence with fresh ideas and innovation.

Classical conditioning, instrumental or operant conditioning, extinction, and habituation can be conceptualized as involving up-regulation and down-regulation of temporal interactions between and among stimuli and responses. Longitudinal node-edge magnitude independence can help enable learning and adaptation in CAS.

Living CAS often come to respond differently in the time dimension as through operant conditioning and classical conditioning and other forms of learning, extinction, and habituation. According to the response component of FIG. 1A, stimuli and tasks can be studied as independent time-series action variables, and behaviors can be studied as dependent time-series action response variables. Forms of adaptation, such as learning and extinction, involve strengthening or weakening temporal-interaction measures in the time dimension. There are additional forms of adaptation. For example, persons can become either sensitized or tolerant as to drugs for pain. These are examples of adaptivity according to this disclosure.

The specified CASM platform includes specific capabilities to quantify evidence for adaptivity. One of these is iterative processing. Iterative processing involves processing the action variable time series anew after the addition of data for additional times. For example, temporal interactions can be quantified anew after adding data for each new time or frame in a data movie (Section 4.1). If there is no temporal interaction, the resulting temporal-interaction scores will hover around zero. If a positive temporal interaction exists or begins to emerge, the temporal-interaction scores will increase steadily, under rather wide-ranging conditions, as the number of repeated measurements increases. Upward magnitude inflections in a graph of temporal-interaction scores as a function of time or repeated measurement occasion would indicate a strengthening of dependent events' dependence, positive or negative, on independent events. Downward magnitude inflections would mean a weakening of dependence, positive or negative, of dependent events on independent events.

Similarly, if a negative temporal interaction exists or begins to emerge, the negative temporal-interaction scores will tend to increase steadily in magnitude as the number of repeated measurements increases. Downward inflections in a graph of negative temporal-interaction scores as a function of time or repeated measurement occasion would indicate the strengthening of dependent events' inverse dependence on independent events. Upward inflections would mean a weakening of dependence of dependent events on independent events.

The specified CASM platform offers an additional means to study adaptivity. For example, functional connectivity measures between and among brain regions may be different before and after learning.

6.4. Non-Linearity:

Characterizations of CAS often mention forms of non-linearity of spatio-temporal interactions between and among multitudes of diverse parts, component systems, and multiple levels of organization. Nested levels of organization in biology include cells, tissues, organs and organ systems, organisms, populations, communities, ecosystems, and biosphere. Levels of organization as for persons include biological, psychological, and social. Despite the importance of interactions, there is a paucity of means to quantify evidence for non-linear temporal interactions.

Brains provide a fitting example of the need for the specified CASM platform to quantify evidence for temporal interactions. Brains epitomize CAS. Modern technology provides a deluge of multivariate time series-data movies-waiting to be processed or developed with the specified CASM platform. For example, functional magnetic resonance imaging (fMRI) of brains can yield data for tens to hundreds of thousands of brain-region-specific or voxel-specific time-dependent potential interactants with a temporal resolution of approximately two seconds or less for minutes or hours. The multivariate time series data from fMRI epitomize the data movies needed to know, explain, help predict, and manage CAS. Multiple technologies, in addition to fMRI, yield data movies. Electroencephalography and magnetoencephalography also yield data movies of action variables for processing with the specified CASM platform.

Recent reports continue attempts to increase the capabilities of correlation coefficients to elucidate brain function. Correlation coefficients are a proper tool to study linear relationships when cross-sectional data are normally distributed and when pairs of measurements such as height and weight are independent because of being collected from different individuals. None of these conditions typically apply to data movies or multivariate time series as for brains. Accordingly, correlation coefficients lack face validity to quantify evidence for functional connectivity as in brains. Understanding, explaining, helping predict, and managing how individual brains function internally is a different and more demanding and challenging kind of problem than getting to know, for example, how height and weight correlate in populations. The use of correlation coefficients to process fMRI multivariate time series data about action variable interactants is improper to the extent that brain function manifests complex adaptive systematicity and that repeated measurements are not independent and normally distributed.

Furthermore, correlation coefficients have been limited to nonexistent capabilities to distinguish causation from mere correlation. Quantification of how brains work in the time dimension involves innumerable action variables-molecular, neuronal, and electrophysiological—for myriad brain regions or voxels. The specified CASM platform has the potential to increase the value of technologies that collect multivariate time series data about CAS.

Responses to treatments, such as drugs, almost certainly are non-linear. Demonstration that a drug is safe and effective at a given dose may not mean that a higher dose is safer and more effective.

6.5. Stochasticity:

Stochasticity in brains and other living systems does appear to have roots in quantum mechanics. For example, gene expression is a fundamentally stochastic process, with randomness in transcription and translation leading to significant cell-to-cell variations in mRNA and protein levels. Cloned cells can have different developmental trajectories. Further for example, stochastic variations in protein levels can, in turn, affect temporal interactions between and among proteins as these can affect how living systems work at physiological, psychological, and social levels of study.

Stochastic models often are contrasted with deterministic models. However, the specified CASM platform is not a model. The specified CASM platform does not attempt to model how CAS work (FIG. 1A). Instead, the specified CASM platform is data-driven. The process for computing universally standardized temporal-interaction scores (Sections 4.8 and 12.6) includes identifying all possible raw scores together with each of their hypergeometric probabilities by random chance. In this sense, the specified CASM platform is inherently stochastic, as are CAS. However, processing the same data with the same CASM scoring protocol will yield identical temporal-interaction scores, including benefit-and-harm scores, unless some error has occurred. CASM scoring protocols are specified in terms of options available within the specified CASM platform.

Furthermore, the process to estimate the quantitative significance of temporal-interaction scores with the specified CASM platform (Sections 4.10 and 12.8) is based on large numbers of random permutations of action variable levels. Estimating CASM significance too is stochastic.

Each measurement in a multivariate time series dataset of action variable levels processed by the specified CASM platform is subject to measurement error, including random measurement error and effects of uncontrolled variables. The specified CASM platform uses information from larger numbers of repeated measurements to distinguish evidence for true signaling from random noise.

6.6. Emergence:

According to this disclosure, emergent properties of CAS derive from longitudinal node-edge magnitude independence (FIG. 2) and components of complex adaptive systematicity other than emergence itself. Accordingly, emergent properties cannot be adequately captured and quantified by applying mathematics to SI units of measurement. Emergent properties need to be quantified as with the specified CASM platform to help investigators advance as through molecular, biological, physiological, psychological, and social levels of study as for EBM-2G. Without the specified CASM platform, investigators seeking to be rigorously scientific have tended to be stuck at the molecular level of inquiry as for precision medicine. Reductionism prevails without measurement that helps account for complex adaptive systematicity.

In contrast, this disclosure has already defined a host of specific and actionable deficiencies and scientific and technical root causes of deficiency that impede EBM, precision medicine, and other antecedents of EBM-2G. These deficiencies involve what has been repeatedly identified in this disclosure as 'limitations and deficiencies' of status quo approaches to patient diagnosis and treatment evaluation for chronic disorders.

More specifically, to measure temporal interactions with universally standardized measurement units is to know temporal interactions (Sections 4.8 and 12.6) that describe and help predict how CAS work in the time dimension (FIG. 1A). Benefit-and-harm scores, as used to quantify evidence for safety and effectiveness, are a subset of temporal-interaction scores. The specified CASM platform helps overcome longitudinal node-edge magnitude independence (FIG. 2) and avoid false negative clinical trial results (FIG. 3B) while helping to account scientifically for the complex adaptive systematicity of personhood. Personhood includes the biological, psychological, and social aspects of the biopsychosocial model.

Two extreme examples illustrate the need to measure emergent properties with temporal-interaction scores in a manner that helps account for complex adaptive systematicity. Suppose that it would be possible to quantify all the mouse's molecular components immediately before and after decapitation. Any molecular differences between these two times are not apt to reveal the massive difference between the mouse being alive and dead. However, decapitation would be a significant disrupter of functional and effective connectivity throughout the body. Differences between being healthy and well versus being ill and diseased are apt to be similar, though more subtle and less extreme.

The molecular approach to precision medicine often involves quick freezing or chemically fixing plasma, blood, and tissue samples from patients and other living systems. Such samples can provide valuable information at the molecular level of study. However, such samples offer little information about the emergent properties of the persons or other living systems from which they were obtained. Death appears to end of temporal interactions of being human as temporal interactions were used to define work in FIG. 1A.

Decapitation also does end action in action variables often used to help determine vital status. Such action variables include respiratory rate, heart rate, blood pressure, temperature, and items in the Glasgow Coma Scale. However, these are vital signs as distinct from descriptions and explanations of vital status per se. Measures of brain electrical activity, also action variables, have been used to help assess brain death. Detailed explanations of vital status and brain death offer to be more medically actionable that vital signs.

Here is another example of the need to study emergence scientifically. Anesthesia can induce dramatic, relatively rapid, and reversible changes in consciousness. Conceivably, applications of the specified CASM platform to fMRI brain imaging data would do more to elucidate the physiological basis of consciousness than the misuse of correlation coefficients as discussed in Section 5.4.1.

Consciousness appears to be at the apex of a hierarchy of emergent properties of individual persons being CAS. Less extreme examples include coordinated action and regulatory control, as introduced in Section 3.1. Many chronic disorders and diseases can be studied in terms of ordered and disordered coordinated action and regulatory control.

6.7. A New Paradigm for Data-Driven Sciences of Complex Adaptive Systems:

The specified CASM platform is offered as a heretofore missing component of a new paradigm for data-driven basic and applied sciences of CAS. This new paradigm helps account for longitudinal node-edge magnitude independence, as illustrated in FIG. 2, and complex adaptive systematicity. CASM helps enable this new paradigm in two distinct but related ways. One of these ways involves quantifying evidence for temporal interactions in the presence of complex adaptive systematicity that was exemplified by being able to quantify protein-protein and brain region temporal interactions to the extent that physical science methods are not sufficient and productive. Another of these ways is by enabling RCTs that quantify evidence for safety and effectiveness across a plurality of response action variables for individual patients and mechanism-specific diagnoses of chronic disorders.

One application of this new paradigm is to help enable EBM-2G.

6.8. EBM-2G Helps Account for the Complex Adaptive Systematicity of Personhood:

One cardinal feature of EBM based on GAS RCT designs was neglecting individual differences in treatment response. EBM earned the recognition of supporting one-size-fits-all medicine as a term of opprobrium. The specified CASM platform offers to help science be more progressive by accounting for individual differences and complexity, adaptivity, non-linearity, stochasticity, and emergent system properties.

Precision medicine, an emerging dominant successor to EBM as of the year 2021, offers to help account for individual differences. However, precision medicine operates primarily at the molecular level of explanation and study. Accordingly, precision medicine neglects how living CAS work in the time dimension (FIG. 1A), longitudinal node-edge magnitude independence (FIG. 2), the problem of false-negative RCT results (FIG. 3B), non-molecular individual differences, and additional manifestations of complex adaptive systematicity of personhood. The five additional manifestations of complex adaptive systematicity identified are complexity, adaptivity, non-linearity, stochasticity, and emergence. To illustrate such neglect with an extreme example, results of genetic screening tests do not include ascertainment of vital status per se.

Genomics does provide a vast resource of potential predictors that remains mostly untapped.

EBM-2G would be based on evidence comprised of both genetic differences and other potential predictors that can be assessed at a single point in time together with EBM-2G quantitative temporal-interaction phenotypes and phenotype tests, computed by applying the specified CASM platform to multivariate time series data.

EBM-2G offers to be scientific medicine more complete. EMB-2G would be based on both SI units of measurement and universally standardized measurement units that quantify evidence for temporal interaction and benefit and harm.

6.9. Patient-Centricity:

Here are just ten ways that EBM-2G with the specified CASM platform can help make treatment evaluations more scientific and patient-centric. The specified CASM platform enables and allows:

1. Longitudinal randomized experimental control of dose in the time dimension for individual patients and other persons enhances the old idea of assessing patient response to drug challenge, de-challenge, and re-challenge as a basis of evidence about causality.
2. The use of longitudinal evidence applies equally to both safety and effectiveness evaluations regarding treatment action variables' effects on treatment response action variables.
3. Both patient safety and effectiveness can be evaluated with the same new and higher standards of scientific excellence.
4. The use of multivariate time series data about treatment and health from pill packs and dispensing and monitoring devices build upon less formal methods for gathering experience and collecting data.
5. Measures computed by applying operationally defined CASM scoring protocols to multivariate time series data are more objective, reproducible, and scientific than subjective impressions and clinical judgments.
6 Universal standardization (Sections 4.8 and 12.6) and overall benefit-and-harm scores allow integrated and balanced scientific evaluations of safety and effectiveness, beginning at each patient's level of study. Testing primary hypotheses based on overall benefit-and-harm scores is an alternative to using primary response variables. A drug has more than one effect.
7 Evaluations of safety and effectiveness as functions of dose allow identifying optimal safe and effective doses for individual patients.
8. The specified CASM platform can distinguish treatment effects from longer-term trends such as from spontaneous recovery or disease progression (Section 4.2). Patients need not be stable as called for by multiple efforts to advance N of 1 RCT designs.
9. The specified CASM platform can evaluate evidence for safety and effectiveness as functions of delay and persistence of response (Sections 4.4 and 12.2.2). Treatment effects need not appear quickly upon initiating treatment or stop quickly upon stopping treatment.
10. Universally standardized benefit-and-harm scores are more objective and scientific than subjective impressions and judgments.

Clinicians treat individual patients, mostly one by one. Health records and experience for individual patients accrue in the time dimension. Accordingly, clinicians, patients, and other stakeholders often form subjective impressions about the safety and effectiveness of individual patients' treatments.

In contrast, treatment guidelines often are based on the results of GAS RCTs that have averaged out the effects of individual differences. At issue is how to account for individual differences. Longitudinal and cross-sectional evidence often leads to conflicting evidence that can lead to different decisions, behaviors, and outcomes. Clinicians can feel pressured to discount their clinical experience and judgment, potentially to their patients' detriment.

7. EBM-2G Randomized Controlled Trial (RCT) Designs

EBM-2G RCT designs evaluate response, as FIG. 1A illustrates, as one part of the tripartite definition of work. The specified CASM platform makes all EBM-2G RCT designs possible. EBM-2G RCT designs often are feasible when both independent or treatment variables and dependent or response variables can be studied as action variables. Section 1 defines action variables. EBM-2G RCT designs use longitudinal (temporal, within-person) randomized experimental control. EBM-2G RCT designs yield experimental multivariate time series data defined in Section 1. The specified CASM platform can evaluate evidence for safety and effectiveness for both action and, with importance weights, non-action response variables (Section 3.2.2).

EBM-2G RCT designs, enabled by the specified CASM platform, can help target the right drug to the right patient at the right safe and effective dose. Targeting with EBM-2G includes accounting scientifically for both molecular differences and the complex adaptive systematicity of personhood. To illustrate causality, gender and genetic differences affect responses to analgesia. To exemplify personhood, preferences, and tradeoffs involving pain-relieving and sedative effects on an analgesic drug can vary both across patients and within patients over time such as before going to work or going to bed.

Additionally, EBM-2G RCT designs help overcome longitudinal node-edge magnitude independence (FIG. 2) and risk of false-negative RCT results (FIG. 3B). Furthermore, EBM-2G RCT designs can yield EBM-2G quantitative treatment response temporal-interaction phenotypes (Section 9.2) that are needed to identify subgroups of responders and accelerate the identification of genetic and other individual differences that predict differential response and optimal safe and effective doses. In contrast, GAS RCT designs are incapable of yielding quantitative treatment response temporal-interaction phenotypes that are reliable and valid for individuals.

Among a litany of other limitations and deficiencies set forth in previous sections, GAS RCTs (Section 2) conflate or confound treatment effects with how they are valued. Historically, pharmaceutical companies selected and defined primary hypotheses on primary response variables in accord with pharmaceutical company interests. Pharmaceutical companies have begun to show interest in the topic of patient-centricity. PCORI took some preliminary steps toward patient-centricity by seeking input about what response variables to use for studies, including RCTs, for treatment approval and EBM. However, PCORI has yet to do much to disrupt CONSORT compliant GAS RCT designs.

Conducting GAS RCTs with more patient-centered response variables offers more patient centricity. However, GAS RCT designs limit patient-centricity by not accounting for individual differences for either causality or patient preference profiles as well as other manifestations of complex adaptive systematicity (Section 6). Unlike with the specified CASM platform, GAS hinders patients who seek to make explicit tradeoffs as among pluralities of beneficial and harmful effects, as introduced in Section 3.2.2. Furthermore, PCORI methodology standards neglect safety. Historically, safety and effectiveness evaluations operate in two different worlds of evidence.

The primary root scientific and technical cause of problems deriving from confounding treatment effects with how treatment effects are valued is the long-standing convention of clinical trialists to define primary hypotheses on primary response variables or endpoints. Treatments typically have multiple effects, beneficial and harmful. Different patients and other stakeholders often have different preferences for the same treatment effects. The interests of those who market drugs can differ from the interests of those who consume drugs. Those who define primary hypotheses on response action variables (Section 1) or artificial endpoints (Section 4.1) impose their values on everyone else.

Instead of defining primary hypotheses on primary response action variables, EBM-2G RCT designs evaluate safety and effectiveness by using a common metric to quantify evidence for benefit and harm regarding a plurality of response action variables (Section 3.2.2). Defining a primary hypothesis on a primary response action variable is, in effect, acting as if a treatment has only one effect that matters. In contrast, most treatments have multiple effects, beneficial and harmful. The convention of defining primary hypotheses on primary response variables largely precludes patient-centricity and contributes mightily to drug safety problems including death. Quantifying evidence for safety and effectiveness with the specified CASM platform offers advanced patient-centricity, patient safety, and drug targeting.

The specified CASM platform offers to help end confounding treatment effects with how they are valued. Avoid confounding by making a clear and actionable distinction between using temporal-interaction scores to quantify evidence for treatment effects as facts of nature from using benefit-and-harm scores that also account for how patients and other stakeholders value treatment effects. Implement this distinction for each person before any statistical aggregation, analysis, and inference from sample to population effects.

As explained in Section 3.2.1, benefit-and-harm scores are temporal-interaction scores that have been modified to account for patient preferences, clinical significance, and other values. Section 3.2.2 describes how a plurality of response action variable specific benefit-and-harm scores in profiles can be differentially weighted to account for differences in importance while computing overall benefit-and-harm scores used to access safety and effectiveness.

The following three sections introduce a series of three EBM-2G RCT designs. Each of the subsequent EBM-2G RCT designs builds on the capabilities of each previous EBM-2G RCT design. EBM-2G RCT designs would largely supersede GAS RCT designs when both independent or treatment variables and dependent or response variables can be studied as action variables (Section 1).

7.1. EBM-2G Single-Person RCT Designs:

GAS RCT designs provide only group-average responses. GAS RCT designs confound effects of individual differences, including genetic differences, with treatment effects by permanently averaging-out effects of individual differences (Section 2). Such confounding impedes both optimal pharmacotherapies for individual persons and identification of predictors of differential response.

Furthermore, EBM-2G single-person RCT designs, enabled by the specified CASM platform, are the foundation for overcoming the limitations and deficiencies of GAS RCTs as already identified in this disclosure. These largely unrecognized or neglected limitations and deficiencies include the five types of confounding listed in Section 5.5, possibilities of false-negative RCT results as illustrated in FIG. 3B, and failure to account scientifically for the six components of complex adaptive systematicity identified in Section 6.

The specified CASM platform increases both the capabilities and the conditions under which single-person RCT designs, by whatever name (e.g., N of 1, n-of-1, one-person, single-patient, single-subject), can be applied.

Sections 4.10 and 12.8 describe how each EBM-2G single-person RCT could test the null hypothesis that a particular drug type is neither safe nor effective for the person being treated. Rejection of such a null hypothesis in the negative direction would indicate that safety problems outweigh effectiveness. Rejection of such a null hypothesis in the positive direction would indicate that effectiveness outweighs safety problems.

Ideally, each EBM-2G single-person RCT would be conducted with pre-specified, operationally defined protocols of two types.

1. Data collection protocols should include complete operationally defined guidelines for collecting the multivariate time series data to be processed. Data collection protocols would include identification of all time-series action variables and how they are to be measured, the temporal resolution of the data (Section 1), the longitudinal randomization plan for one or more independent or treatment action variables (Section 2), and the number of repeated measurements of all action variables for each person.

2. CASM scoring protocols that operationally define computation of all benefit-and-harm scores using the specified CASM platform. These protocols would include options such as those identified in Sections 4.2, 4.3, 4.4, 4.5, and 4.10.

As described in Section 5.5, CONSORT has played a role in making the evidence base for medicine more scientific. However, the specified CASM platform offers to outmode many applications of GAS RCT designs, the reporting of which is addressed by CONSORT. CONSORT is based on the 'standard' two-group parallel design. These are what this Section 2 identifies as GAS RCT designs. However, CONSORT does include multiple extensions. One extension is for "within person trials." "The CONSORT extension for within-person trials is meant to extend CONSORT checklist items to facilitate the reporting of trials of conditions that can affect two or more body sites of the same kind such as when one eye is treated, and one eye is not treated. These are a useful and efficient tool because the comparisons between interventions are within persons. Although this extension uses "within person" terminology, neither this nor any other CONSORT compliant clinical trials can account scientifically for the complex adaptive systematicity as introduced in Section 6.

Another CONSORT extension is about "N-of-1 trials." "N-of-1 trials provide a mechanism for making evidence-based treatment decisions for an individual patient." However, CONSORT compliant N-of-1 trials cannot provide any of the six examples of information about safety and effectiveness, as listed in Section 4.1.

CONSORT compliant clinical trials do not use a common metric to evaluate safety and effectiveness (Section 3.2.2). To illustrate, the CONSORT extension about "N-of-1 trials" includes a diagram. Diagrams have been developed to help authors visually depict both an individual participant's progress through an N-of-1 trials and the flow of multiple participants through a series of trials. Users are left to evaluate evidence for effectiveness subjectively. In contrast, the specified CASM platform can quantify temporal interaction evidence scientifically. To illustrate, the diagram included in the CONSORT extension for N-of-1 trials appears to show a total of 48 repeated measurements—a total of 28 repeats for run-in and washout times and 20 repeats when active treatment was present at some unspecified non-zero dose. Assuming higher outcome measurement levels are favorable and toward, these data's benefit score is 27.36 standard deviation units—bagnes when computed with the specified CASM platform (Section 4.8).

Measurement of temporal interaction evidence for safety and effectiveness with the specified CASM platform helps make it possible to model safety and effectiveness mathematically and statistically. Measurement of temporal interaction evidence for safety and effectiveness also makes it possible to conduct many EBM-2G group RCTs using sets or series of N-of-1 or single-person EBM-2G RCTs (Section 7.2).

7.2. EBM-2G Single-Group, Multiple Single-Person, RCT Designs:

These designs offer to evaluate the overall safety and effectiveness of individual drug types during drug development, reformed drug approval, and EBM-2G.

EBM-2G single-group, multiple single-person, RCT designs are comprised of a plurality of EBM-2G single person RCT designs (Section 7.1). Accordingly, clinical trialists can benefit from all the information about safety and effectiveness for each person, as exemplified by the six points in Section 4.1.

Additionally, and since there is a plurality of persons in each EBM-2G single-group, multiple single-person RCT, benefit-and-harm scores can be aggregated, modeled, and analyzed statistically. Statistical hypothesis testing should be in accord with a pre-specified statistical protocol in addition to the data collection and CASM scoring protocols identified in Section 7.1.

Each EBM-2G single-group, multiple single-person RCT could test the null hypothesis that a particular drug type is neither safe nor effective for the sampled population. Test such a null hypothesis with a single-group t-test on mean overall benefit-and-harm scores. Rejection of such a null hypothesis in the negative direction would indicate that safety problems outweigh effectiveness. Rejection of such a null hypothesis in the positive direction would suggest that effectiveness outweighs safety problems.

Scores provided by the specified CASM platform make it possible to compute group averages for all six of the person-specific points listed in Section 4.1. Each EBM-2G single-group, multiple single-person RCT can provide group averages, as illustrated by an example.

1. The group average overall benefit-and-harm score assessed across six differentially weighted response variables affected either beneficially or harmfully, 2. A group average safety and effectiveness profile comprised of an average universally standardized benefit-and-harm score for each of the six response variables, 3. Group average overall safety and effectiveness as a function of five analgesic doses, including zero, that also identifies the group average optimal safe and effective dose given the data for a plurality of persons, 4. Group average safety and effectiveness as a function of dose for each of the six safety and effectiveness response variables, 5. Group average response-variable specific and overall safety and effectiveness as functions of four levels of delay of response, and 6. Group average response-variable specific and overall safety and effectiveness as functions of four levels of persistence of response.

Benefit-and-harm scores from EBM-2G single-group, multiple single-person RCTs are amenable to additional types of exploratory statistical analyses. As examples, cluster analysis could be used to identify subgroups of safety and effectiveness responders. Factor analysis could be used to identify treatment effect factors. For example, dry mouth, dry eyes, blurred vision, urinary retention, and constipation appear to form an anticholinergic factor for some drugs such as tricyclic antidepressants.

Additionally, EBM-2G single-group, multiple single-person RCTs yield EBM-2G treatment response temporal-interaction phenotypes (Section 9.2). Such phenotypes can be used with additional data, such as genetic data, to identify individual differences predictive of differential response and optimal safe and effective doses.

7.3. EBM-2G Parallel, Multiple Single-Group, Multiple Single-Person, RCT Designs:

These designs enable integrated comparative safety and effectiveness research regarding treatment and response action variables (Section 1). Such designs would attempt to reject the primary statistical null hypothesis of no difference in overall safety and effectiveness between two or more types of treatment. For example, a t-test for independent groups can be used to compare the overall safety and effectiveness of two drug types. The null hypothesis would be no difference in overall safety and effectiveness. Rejection of the null hypothesis would indicate that one drug is safer and more effective than the other drug. Additionally, each drug could be tested individually (Section 7.2).

The specified CASM platform helps enable integrated action variable 'comparative safety and effectiveness' as distinct from having to meld safety and effectiveness from different worlds of evidence collected with varying standards of scientific excellence. For example, evidence about efficacy from GAS RCTs typically has been based on statistical testing of primary hypotheses defined in terms of primary response variables and endpoints. In contrast, safety often has been based on rates and proportions of spontaneous reports by clinicians and patients.

Each person in an EBM-2G parallel, multiple single-group, multiple single-person RCT can be doubly randomized. Persons can be cross-sectionally randomized into two or more groups defined by types of treatment. Each person would also be longitudinally randomized to receive two or more doses of the same kind of drug into two or more periods.

Parallel, multiple single-group, multiple single-person RCT designs offer to provide all the information about each person as exemplified in Section 7.1 and all the information about each group, as presented in Section 7.2.

Additionally, parallel, multiple single-group, multiple single-person RCT designs offer to provide information about group comparisons as exemplified here for two groups.

1. The group-average difference in overall benefit-and-harm scores assessed across six differentially weighted response variables affected either beneficially or harmfully,
2. The group-average differences in safety and effectiveness profiles comprised of a group-average difference in universally standardized benefit-and-harm score for each of the six response action variables,
3. The group-average differences in overall safety and effectiveness as a function of five analgesic doses, including zero, that also identifies the group-average differences in optimal safe and effective dose given the data for a plurality of persons,
4. The group-average differences in safety and effectiveness as a function of dose for each of the six safety and effectiveness response variables,
5. The group-average response-variable specific and overall safety and effectiveness as functions of four levels of delay of response, and 6. The group-average response-variable specific and overall safety and effectiveness as functions of four levels of persistence of response.

EBM-2G RCT designs offer to provide more information to make better decisions because the decisions improve health and lower costs by targeting the right drug to the right person at the right dose and away from persons who would be harmed.

7.4. Quantitative Significance and Power:

This disclosure uses 'quantitative significance and power' to include two conceptually related but distinct capabilities.

1. Statistical significance and power for making inferences and drawing conclusions from random samples to statistical populations of similar individuals, and
2. CASM significance and power for making inferences and drawing conclusions about individual CAS such as persons.

EBM is mostly based on GAS RCTs that use statistical significance and power. In contrast, EBM-2G would be based on CASM significance and power as well as statistical significance and power when there is a plurality of persons. EBM-2G is an example of two being better than one-better decisions about both each person and the population.

Distinguish quantitative significance from clinical, personal, and social significance (Section 3.2.1). The specified CASM platform uses differential weights to help account for differences in the clinical, personal, and social significance of treatment effects regarding various response action variables when computing overall benefit-and-harm scores to evaluate overall safety and effectiveness.

Historically, concepts of significance and power for hypothesis testing and inference have been addressed almost exclusively regarding the discipline of statistics about groups, samples, and populations as for GAS RCT designs and other cross-sectional experiments. In this context, a result has statistical significance when the probability of the observed data is low given that the null hypothesis is true.

Relatedly, the power of a binary hypothesis test is the probability that the test rejects the null hypothesis when a specific alternative hypothesis is true. Statistical tests use data from samples to assess, or make inferences about, a statistical population.

Quantitative significance and power are about avoiding error. In statistical hypothesis testing, a type I error is the rejection of a true null hypothesis (also known as a "false positive" finding or conclusion), while a type II error is the non-rejection of a false null hypothesis (also known as a "false negative" finding or conclusion). Much of statistical theory revolves around the minimization of one or both of these errors. Using larger sample sizes of subjects has been a major means of reducing type I and type II errors.

The medical statistics discipline has made medicine more scientific. However, the statistical approach has limitations and deficiencies that include the five types of confounding and conflation identified in Section 5.5, the possibility of false-negative RCT results illustrated by FIG. 3B, and failure to account scientifically for the complex adaptive systematicity of personhood (Section 6). By example, statistics and EBM have become the basis of one-size-fits-all medicine, first mentioned herein in Section 2.

Section 4.10 introduces how the specified CASM platform estimates the quantitative significance of temporal-interaction scores and benefit-and-harm scores about individual CAS. The specified CASM platform helps make empirical studies of individual CAS possible. For example, Section 7.1 introduced EBM-2G single-person RCT designs. Sections 7.2 and 7.3 introduce how group RCTs can evaluate safety and effectiveness (Section 7) as statistically aggregated and analyzed sets or series of EBM-2G single-person RCT designs.

The specified CASM platform uses a different approach to increase quantitative significance and power-larger numbers of repeated measurements of action variables for everyone. Larger numbers of repeated measurements allow randomized experimental control to be exercised longitudinally in the time dimension. The specified CASM platform can use larger numbers of repeated measurements to help overcome the random error of measurement of time-series action variables and effects of action variables not controlled by longitudinal randomization. The specified CASM platform helps enable EBM-2G as an exemplary application.

In addition to using larger numbers of subjects, statistical significance and power can be increased by increasing the reliability of statistically analyzed measures. Not only do larger numbers of repeated measurements increase CASM significance and power, but larger numbers of repeated measurements also increase the reliability of temporal-interaction scores as well as benefit-and-harm scores for evaluating safety and effectiveness—other factors being equal. Accordingly, the specified CASM platform offers to increase statistical significance and power in both EBM-2G single-group, multiple single-person RCTs (Section 7.2) and EBM-2G parallel, multiple single-group, multiple single-person RCT (Section 7.3).

FIG. 5 is a table 500 illustrating example results from a simulation that shows how using larger numbers of repeated measurements of time-series action variables offer to increase statistical significance when benefit-and-harm scores are computed from data with larger numbers of repeated measurements. Results in the "With CASM (Benefit & Harm Scores)" section of FIG. 5 were computed with CASM.

For simplicity, the simulation that yielded the results shown in FIG. 5 used only one treatment action variable and one response action variable. The entire simulation used 32 repeated measurements for each of 64 subjects. Each response variable repeated measurement for each subject was a random normal deviate except when treatment was present. When treatment was present, a small constant was added to the random normal deviate. This constant represented a treatment effect signal. The random normal deviates simulated random noise from measurement errors for the response variable and the effects of uncontrolled variables that might affect response variable levels. For example, suppose this simulation was about evaluating the effect of an antihypertensive drug on blood pressure. In that case, uncontrolled variables could have included stress, anxiety, diet, and exercise on blood pressure that could vary together with treatment in the time dimension.

The "p-values (levels of statistical significance)" were obtained using two types of t-tests for two categories of RCT design. For the "Without CASM" or GAS-RCT column, the p-values were for a t-test for two independent groups using baseline-to-endpoint change scores for two parallel and equal groups. One group was treated and one not, using the first (baseline) and last (artificial endpoint, Section 2) random normal deviates for the response variable. As expected, the "p-values" in the "Without CASM" column quantify higher significance as the "Number of Subjects" increased from 4 to 8, 16, 32, and 64 subjects.

The "p-values" in the "With CASM" portion of the results table are for a two-tailed, single-group t-test on the mean benefit-and-harm score. This portion of the simulation results in FIG. 5 are for an EBM-2G single-group, multiple single-person RCT design (Section 7.2). All "p-values" were for results in the positive direction. Similarly, to the "Without CASM" results, the "p-values" for two repeated measurements in the "With CASM" section also quantify higher significance as the "Number of Subjects" increases. However, observe how the p-values in the "With CASM" section tend to show increased statistical significance as the number of repeated measurements processed with CASM increases from 2 to 4, 8, 16, and 32 repeated measurements. The column labeled "4" repeated measurements was obtained using the first two and the last two repeated measurements for each subject in the dataset. Similarly, the column labeled "8" used the first four and the last four repeats. The column labeled "32" used all repeated measurements.

The "Simulation Results" in FIG. 5 show the specified CASM platform, can achieve substantial increases in statistical significance compared to both GAS RCT designs and EBM-2G single-group, multiple single-person RCT designs with smaller numbers of repeated measurements. Larger numbers of repeated measurements increased statistical significance by increasing the reliability of the benefit-and-harm scores computed with CASM. In effect, CASM and statistics operated synergistically to increase statistical significance.

In general, repeated measurements as obtained with drug dispensing and monitoring devices and health monitoring devices and electronic diaries can be expected to be less expensive than accruing larger numbers of subjects. The specified CASM platform can help save time and money for drug development and EBM-2G.

The "Simulation Results" in FIG. 5 also show tradeoffs that clinical trialists can make when they have a fixed or limited budget for data collection. If a clinical trialist needs reliable and valid results for each person, then it would be advantageous to apply the specified CASM platform with more repeated measurements for each person and fewer persons. If a clinical trialist needs results that are more representative of some population, then she or he could use fewer repeated measurements and more persons. Ideally, it would be better to use both more persons and more repeated measurements for each person.

7.5. Transitioning to EBM-2G RCT Designs:

EBM-2G RCT designs offer to improve drug development productivity and healthcare cost-effectiveness by increasing scientific veracity. Additionally, this approach provides patient-specific evaluations of safety and effectiveness that are reliable; valid; comprehensive of multiple beneficial and harmful effects; and detailed as about dose-response relationships, delay of response, and response persistence. Nevertheless, it can be challenging to transition from legacy clinical trial designs to EBM-2G clinical trial designs. Fortunately, the specified CASM platform affords users abundant opportunities to conduct exploratory studies with readily available data.

Opportunities for exploratory studies include reprocessing data from pre-clinical studies and early phase clinical studies. Early-phase clinical studies often are conducted with healthy subjects in overnight facilities with intensive laboratory and electrophysiological monitoring from one to several days. Such studies often include repeated measurements of drug and drug metabolites in bodily fluids. Since the specified CASM platform processes data with independent or treatment action variables as distinct from categorical independent variables, investigators could quantify evidence for safety and effectiveness as functions of drug or drug metabolite levels starting at the level of each person or subject. Available data might not be ideal without longitudinal randomized experimental control. Additionally, repeated measurements often are collected sporadically instead of periodically. Periodically repeated measurements would facilitate studies of safety and effectiveness as functions of delay and persistence of response.

Furthermore, the specified CASM platform can quantify evidence for safety and effectiveness according to the intent-to-treat principle as well as with indicators of actual drug consumption as collected with medication event monitoring systems. Accordingly, this would facilitate studies of how compliance and non-compliance with prescribed treatment regimens may affect safety and effectiveness.

7.6. Expanding and Inventing from EBM to EBM-2G:

EBM is about putting populations first as with GAS RCT designs that confound treatment effects with effects of individual differences, including genetic differences (Section 2).

Constructing an evidence base for EBM-2G for chronic disorders of internal function can be likened to creating a two-way street between individuals and populations. This approach offers to help integrate clinical research and clinical practice for chronic disorders that account for about 85% to 90% of health care expenditures in the United States. Both Sections 7.2 and 7.3 show how users of the specified CASM platform can test hypotheses about overall safety and effectiveness in populations while still being able to drill down to person-specific and response-variable-specific information about safety and effectiveness. It is possible to compute within-patient indicators of treatment effect that are more reliable, valid, comprehensive, and detailed for each person before any statistical aggregation and analyses about groups and populations Sections 5.4.2.1 through 5.4.2.4. However, the cultural barriers to more informative, high-veracity, and high-productivity science are formidable (Section 5.5).

In contrast to applying the specified CASM platform, EBM constructs its evidence base mostly on GAS RCT designs that put populations, not individuals, first. Additionally, EBM-2G offers to help account scientifically for the complex adaptive systematicity of personhood.

EBM-2G is expansive in at least three ways compared to EBM.

1. EBM-2G is based on data movies. In contrast, EBM has been mostly based on data snapshots, including change scores. Data movies can offer orders of magnitude more information (Section 4.1) about how individual persons work in the time dimension (FIG. 1A). Compared to EBM, EBM-2G draws from a much more bottomless well of evidence.

2. EBM-2G can use both longitudinal and cross-sectional randomized experimental control. In contrast, EBM is limited to cross-sectional randomized experimental except for some ABAB type crossover designs.

3. EBM-2G can use both CASM significance for making inferences about individuals and statistical significance for making inferences from samples of individuals to populations. In contrast, EBM is mostly limited to statistical significance for making inferences from samples of individuals to populations.

EBM-2G is digital in a way that EBM is not (Section 4.3). In contrast, EBM is analog in the way it processes dimensional variables. Digitizing dimensional variables before further data processing enables multiple new capabilities, much as digital photography does compared to film photography. Additional capabilities include being able to quantify safety and effectiveness as functions of dose and response variable level (Sections 4.3 and 12.1); account for episodes of events, delay of response, and response persistence (Sections 4.4 and 12.2); and account for Boolean events (Sections 4.5 and 12.3). Additionally, digitization of dimensional action variables allows for universal standardization of temporal-interaction and benefit-and-harm scores as units of measurement.

EBM-2G computes the EBM-2G quantitative temporal-interaction phenotypes, and tests (Section 9) needed to accelerate genotype-phenotype mapping. Because of this constellation of capabilities, EBM-2G has the potential to supersede EBM, personalized medicine, P4 medicine, and molecular medicine for the prevention and management of chronic disorders that become evident and often need to be treated in the time dimension.

8. Effects Monitoring, EBM-2G Health-Effects Monitoring

Clinical trial data typically are processed in batches, often at the end of a trial. The specified CASM platform also can be used to process data in batches as for EBM-2G RCT designs.

Additionally, the specified CASM platform can process multivariate time series data for action variables repeatedly as new data become available (iterative processing) to quantify and monitor evidence for any temporal interactions for individual CAS, including persons.

Effect monitoring as involving health can be described in either of two ways. One means of description is to emphasize one or more time series acting as independent action variable time series. The second means of description is to highlight one or more dependent action variable time series. Either way, independent and dependent action variables are broadly defined (Section 2).

To exemplify this distinction, diet, exercise, drug consumption, and exposures to allergens and pollutants can affect health. When the emphasis is on independent action variables, one could describe this as diet effects monitoring, exercise effects monitoring, drug effects monitoring, allergen effects monitoring, or pollutant effects monitoring. Alternatively, all these collectively can be described as health-effects monitoring by shifting the emphasis to dependent action variables. EBM-2G health-effects monitoring, as used in this disclosure, refers to this second means of description. Additionally, health could be studied as an independent action variable to study and monitor, as examples, how mental or physical health may affect social role functioning as for parenting or job performance.

Effects monitoring is an inclusive term that applies when the specified CASM platform is applied to monitor the effects of one or more independent action variables on one or more dependent action variables about an individual CAS of any type. Effects monitoring includes EBM-2G health-effects monitoring with independent environmental and treatment action variables and dependent or response health or health-related action variables. Non-limiting examples of time series, that can be studied as independent environmental and treatment action variables for EBM-2G health-effects monitoring, include drug consumption, diet, exercise, allergens, pollutants, behaviors, stimuli, and climate variables. Non-limiting examples of time series, that can be studied as dependent or response action variables, include signs and symptoms of a disease; measures of wellness, health, and mental and physical performance; and measures of quality of life, including social role functioning.

Persons often monitor health and wellness together with variables that may affect health and wellness because they want to improve health and wellness. However, the resulting multivariate time series, by themselves, may not be actionable because the data, by themselves, say little if anything about causation. Statistical measures of central tendency, dispersion, and correlation are of little value for elucidating causation at each person's level, and when relationships between and among action variables are not linear. Statistics do not substitute for the temporal-interaction scores or benefit-and-harm scores. In contrast, EBM-2G health-effects monitoring with the specified CASM platform helps make monitoring of the action variables actionable by quantifying the temporal interactions, including benefit and harm, that describe and help predict causation.

Ways to monitor effects, including health effects, is with moving or expanding windows of experience as with 20, 50, 100, or 200 repeated measurements. Then CASM significance of temporal-interaction scores and benefit-and-harm scores can be estimated (Sections 4.10 and 7.4) to help provide quantitative evidence for decision-making about individuals much as statistical significance provides quantitative evidence for decision-making about groups, samples, and populations.

A related application of EBM-2G health-effects monitoring would be during EBM-2G RCTs. This approach can be developed for ultra-adaptive EBM-2G RCTs, providing that appropriate care is taken to avoid false-positive RCT results resulting from repeated testing.

Although effects monitoring has been presented in the context of response to environmental action variables, effects monitoring also applies to internal function and agency as internal function, response, and agency, as FIG. 1A portrays the tripartite definition of work. For example, the specified CASM platform can be applied to monitor the effects of one hormone on the secretion of other hormones.

9. EBM-2G Quantitative Temporal-Interaction Phenotypes and Phenotype Tests

Conventional precision medicine lacks high fidelity phenotypes and phenotype tests. In contrast, EBM-2G can accelerate drug development and healthcare that provides better outcomes at lower costs with high fidelity phenotypes and phenotype tests. High fidelity phenotypes and tests would help overcome longitudinal node-edge magnitude independence (FIG. 2), avoid the risk of false-negative RCT results (FIG. 3B), and account for the complex adaptive systematicity of personhood (Section 6).

In addition to molecular phenotypes and surrogate measures often used in conventional precision medicine, the specified CASM platform enables 'temporal-interaction phenotypes.' Temporal-interaction phenotypes quantify multiparametric patterns with temporal-interaction scores as evidence about how individual CAS such as persons work in the time dimension. FIG. 1A illustrates the operational definition of 'work' used in this disclosure. FIG. 2 shows longitudinal node-edge magnitude independence. Nodes in both figures include repeated measurements of molecular phenotypes for action variables. More inclusively, action variables for EBM-2G can be at the physical, molecular, cellular, electrophysiological, behavioral, psychological, social, and quality of life levels of study. Edges in FIGS. 1A and 2 represent temporal interactions that can be quantified with the specified CASM platform. Temporal interactions can be quantified when it is possible to obtain time-series data for independent and dependent action variable nodes.

Temporal-interaction phenotypes use universally standardized temporal-interaction scores (Sections 4.8 and 12.6) to quantify edges in graphs with time-series nodes. Precision quantitative temporal interaction phenotypes are computed by applying the specified CASM platform to multivariate time series data (Section 1).

Section 4.1 discussed the data snapshot/data movie analogy. Accordingly, structural and molecular phenotypes typically are based on data snapshots ascertained at specific points in time, such as at the time of a clinic visit or hospital admission. In contrast, temporal-interaction phenotypes are based on data movies (multivariate times series) that can have orders of magnitude more information to know and phenotype persons and other living systems compared to structural and molecular phenotypes captured with data snapshots. Temporal-interaction phenotypes require at least one time series to operate as an independent variable and at least one time series to operate as a dependent variable. Both independent and dependent variables are broadly defined (Section 1).

In turn, temporal-interaction phenotypes often would need to be tested to estimate the probability that an observed temporal-interaction score or benefit-and-harm score was not the result of random chance. In some embodiments, each temporal-interaction phenotype test would be comprised of three primary components:

1. An operationally defined protocol for collecting multivariate time series data for both independent and dependent variables;
2. An operationally defined CASM platform scoring protocol for computing temporal-interaction scores, including benefit-and-harm scores, from the multivariate time series data, with complete and detailed information about Steps 2 through 9 in Section 4; and
3. An operationally defined protocol for estimating the CASM significance of the resulting summary temporal-interaction score or summary benefit-and-harm score (Sections 4.10 and 12.8).

Temporal-interaction phenotypes are quantitative and dimensional as distinct from being categorical. As categorical examples, patients may be diagnosed as either having or not having Type II diabetes based, at least in part, on evidence about insulin resistance. Similarly, patients have been classified as either responders or non-responders to a specified type of drug. In contrast, temporal-interaction phenotypes are quantitative and dimensional, to help account for degrees of insulin resistance and degrees of treatment response. The CASM significance feature of the specified CASM platform (Sections 4.10 and 12.8) would be used to estimate that a specified summary temporal-interaction score or benefit-and-harm score (Section 4.9) is not due to random chance.

Here are three major categories of temporal-interaction phenotypes and phenotype tests. These correspond to the tripartite definition of work shown in FIG. 1A.

1. EBM-2G quantitative diagnostic temporal-interaction phenotypes and phenotype tests,
2. EBM-2G quantitative environmental and treatment response temporal-interaction phenotypes and phenotype tests, and
3. EBM-2G quantitative agency temporal-interaction phenotypes and phenotype tests.

Although quantitative phenotypes and tests are exemplified in the context of EBM-2G for persons, the same concepts and methods apply to basic and applied sciences of CAS.

Temporal-interaction phenotypes and tests include challenge tests conducted by applying the specified CASM platform. Challenge tests administer substances or other exposures to test response. As examples, challenge tests have been used for diabetes and other chronic disorders, including asthma. Challenge tests quantify response to probes such as glucose, insulin, exercise, and cold air. Some drugs can be used as diagnostic probes to assess responses to confirm or disconfirm diagnostic hypotheses. Challenge tests that include applications of the specified CASM platform offer reliability, validity, and more detailed information by using larger numbers of repeated measurements and within-person longitudinal randomized experimental control with two or more levels of the challenge substance or exposure.

9.1. EBM-2G Diagnostic Temporal-Interaction Phenotypes and Phenotype Tests:

Section 5.4.1 about neuropsychiatric disorders exemplified how many diagnoses of chronic disorders could be improved by applying the specified CASM platform to multivariate time series, including functional brain imaging data. This approach results in diagnostic phenotypes that are reliable and mechanism-specific that can, in turn, improve targeting the right drug to the right person at the right safe and effective dose.

A cardinal feature of EBM-2G diagnostic temporal-interaction phenotypes, measured by applying the specified CASM platform, is that they would quantify evidence of temporal order and disorder per se as distinct from how the International Classification of Diseases (ICD) and the Diagnostic and Statistical Manual (DSM) of mental disorders are based on signs and symptoms of disorder (Section 2). Additionally, EBM-2G diagnostic temporal-interaction phenotypes would help account for the complex adaptive systematicity of personhood (Section 6).

As EBM-2G diagnostic temporal-interaction phenotypes are being developed and deployed, it will become increasingly important and valuable to determine whether or not or to what degree a person meets the criteria for an EBM-2G diagnostic temporal-interaction phenotype. EBM-2G diagnostic temporal-interaction phenotype tests serve this purpose. Ideally, each EBM-2G diagnostic temporal-interaction phenotype test would be comprised of all three components identified in Section 9.

Additionally, diagnostic temporal interaction phenotypes and phenotype tests can be targets of drug discovery and development. As examples, drugs could be developed and approved regarding their abilities to up-regulate or down-regulate temporal interaction phenotypes such as between and among hormone levels and brain region activity levels.

9.2. EBM-2G Quantitative Environmental and Treatment Response Temporal-Interaction Phenotypes and Phenotype Tests:

Section 5.4.2 and its five subsections focused on neuropsychiatric disorders to exemplify the need to improve targeting of drugs for chronic disorders by applying the specified CASM platform to obtain person-specific measures of treatment response that are reliable, valid, comprehensive of multiple beneficial and harmful effects, and detailed as about dose.

Furthermore, EBM-2G RCT designs would quantify EBM-2G quantitative treatment response temporal-interaction phenotypes. All six points listed in Section 7.1 exemplify the type of information included in an EBM-2G treatment response temporal-interaction phenotype. Additionally, EBM-2G health-effects monitoring (Section 8) can identify EBM-2G quantitative environmental and treatment response temporal-interaction phenotypes such as about diet, allergens, and other environmental exposures. As EBM-2G quantitative environmental and treatment-response temporal-interaction phenotypes are being developed and deployed, it will become increasingly important and valuable to determine whether or to what degree a person meets the criteria for an EBM-2G quantitative environmental or treatment-response temporal-interaction phenotype. EBM-2G quantitative environmental and treatment-response temporal-interaction phenotype tests serve this purpose. Ideally, each EBM-2G quantitative environmental and treatment response temporal-interaction phenotype test would be comprised of all three components identified in Section 9.

Results of a test about a particular person's response better predicts that same person's continued response than group-average results from hundreds or thousands of subjects in GAS RCTs. EBM-2G quantitative treatment response temporal-interaction phenotype tests offer to reduce costs of treatments for patients that are not helped and reduce safety problems and costs of patients for whom harms outweigh benefits.

9.3. EBM-2G Quantitative Agency Temporal-Interaction Phenotypes and Phenotype Tests:

FIG. 1A shows that the tripartite definition of 'work' used for this disclosure includes agency as well as internal function and response. Agency for the specified CASM platform is when one or more action variable time series that are internal to or characteristic of an individual complex adaptive system operate as independent variables and one or more time series external to the complex adaptive system or characteristic of its environment operate as dependent variables.

Agency includes behaviors of individual CAS, including persons, when monitored behaviors operate as independent variables when processed by the specified CASM platform together with monitored dependent variables. Monitored dependent variables that can be of distinct types and from different disciplines. Non-limiting examples include physical, chemical, physiological, psychological, social, and economic dependent action variables. Accordingly, the resulting universally standardized (Section 4.8) temporal-interaction scores (Section 3.1), as well as benefit-and-harm scores (Sections 3.2.1 and 3.2.2), quantify evidence for agency.

Applications of the specified CASM metrology platform help extend the scope of EBM from (1) diagnoses of disordered internal function and (2) evaluations of response as with GAS RCT designs (Section 2) to EBM-2G that includes (1) diagnosis of disordered internal function per se, (2) evaluations of response as with EBM-2G RCT designs (Section 7) and (3) scientific assessments of agency as of patients, clinicians, and other stakeholders. Examples of agency include persons taking more or less responsibility for their own health and wellness (self-care) and pay for performance-plans (Section 3.2.2).

In some embodiments, each EBM-2G quantitative agency temporal-interaction phenotype test would include all three components identified in Section 9.

EBM-2G quantitative agency-on-self-care temporal-interaction phenotype tests have been exemplified for persons as for EBM-2G. Essentially the same approach can be applied to additional types of CAS such as firms, companies, and organizations seeking to improve their performance.

9.3.1. EBM-2G Quantitative Agency-on-Self-Care Temporal-Interaction Phenotypes and Phenotype Tests:

Persons are agents for their own self-care. Section 2 has already discussed how persons who recognize and appreciate their uniqueness might seek to participate in and take more responsibility for their health and wellness through self-care. Self-care includes many persons in the quantified-self community who already monitor their health, wellness, fitness, and performance as well as environmental exposures, treatments, and behaviors that may affect health, wellness, and performance.

EBM-2G health-effects monitoring (Section 8) with the specified CASM platform helps transform information in such monitoring data into actionable knowledge about causation.

The impact and value of EBM-2G health-effects monitoring can be assessed in at least two fundamentally separate ways. A cross-sectional evaluation would be to randomize persons into two distinct groups. Each person in both groups would monitor health, wellness, and performance as well as environmental exposures, treatments, and behaviors that may affect health, wellness, fitness, and performance. However, only one group would also apply EBM-2G health-effects monitoring. Then the two groups could be compared regarding their health, wellness, and performance. In effect, this would be a GAS RCT in which EBM-2G health-effects monitoring would be investigated, much like GAS RCTs evaluate drugs. This approach would be valued, much like GAS RCTs have been valued. However, GAS RCT designs have limitations such as not accounting scientifically for the complex adaptive systematicity of personhood (Section 6). For example, the effects of health-effects monitoring are apt to vary by person much as drug effects vary by person.

An alternative longitudinal approach to evaluating EBM-2G health-effects monitoring's impact and value would be with EBM-2G RCT designs (Section 7). Again, health-effects monitoring could be investigated as an intervention much as pharmacotherapy can be studied. Since persons participating in EBM-2G RCTs of health-effects monitoring could be expected to learn what causes what, it would be essential to separate short-term effects of EBM-2G health-effects monitoring from longer-term trends (Section 4.2). Users of this approach would be able to conduct an EBM-2G quantitative agency-on-self-care temporal-interaction phenotype test on each person. These tests would compare and contrast health, wellness, fitness, and performance for periods when EBM-2G health-effects monitoring was present with periods when EBM-2G health-effects monitoring was absent. Again, ideally such tests would be comprised of all three components identified in Section 9.

9.3.2. EBM-2G Quantitative Agency-on-Others-and-One's-Environment Temporal-Interaction Phenotypes and Phenotype Tests:

These are the same as EBM-2G quantitative agency-on-self-care temporal-interaction phenotype tests except that the monitored dependent action variables would be about the environment of the complex adaptive system. The environment of a complex adaptive system can include other CAS of the same or different kinds.

10. All-of-Us Plus Each-One-of-Us Equals EBM-2G

FIG. 4 is a block diagram illustrating a second-generation evidence-based medicine (EBM-2G) flow 400 for applying predictors to identify predictors for individual patients.

The All of Us Research Program is a major initiative by the United States NIH available at (https://allofus.nih.gov/about/all-us-research-program-overview). This Program includes collecting a vast quantity of genomic data about 1,000,000 or more persons. FIG. 4 uses 'All of Us' to represent both genomics generally and the genomics contribution to EBM-2G.

However, genomics is necessary but not enough to achieve EBM-2G. EBM-2G also needs the specified CASM platform to compute quantitative temporal interaction phenotypes about the 'each one of us' portion of FIG. 4. Applications of the specified CASM platform include EBM-2G RCT designs (Section 7), EBM-2G health-effects monitoring (Section 8), and EBM-2G quantitative temporal-interaction phenotypes and tests (Section 9). FIG. 4 represents all of these with computational phenomics.

The problem for genomics is lack of adequate phenomics. Diagnostic taxonomies such as ICD and DSM together with GAS RCT designs (Section 2), established long before genomes were decoded, do not provide high-fidelity phenotypes. High-fidelity phenotypes would help overcome longitudinal node-edge magnitude independence (FIG. 2), avoid the risk of false-negative RCT results (FIG. 3B), and account scientifically for the complex adaptive systematicity of personhood (Section 6). High-fidelity phenotypes offer to accelerate genotype-phenotype mapping. The specified CASM platform allows users to compute the required high-fidelity phenotypes. High-fidelity phenotypes are quantified with a new category of computed measures-universally standardized temporal-interaction scores and benefit-and-harm scores. The specified CASM platform capitalizes more rapidly on genomics. Sections 4.8 and 12.6 present universal standardization.

Broad spectrum diagnostic phenotypes such as autism spectrum disorder, type 2 diabetes mellitus, bipolar disorder, and schizophrenia are not mechanistically specific enough to identify high power predictors, genetic or otherwise. High specificity for both genomics and phenomics offers to increase predictive power.

The arrows in FIG. 4 show how its two parts are related in a mutually beneficial and synergistic manner. 'Each one of us' needs help from 'all of us' as for healthcare to help identify genetic predictors of what is best for 'each one of us' as indicated by the top arrow. Additionally, 'each one of us' has something of value to offer 'all of us' once our high-fidelity phenotypes are computed by application of the specified CASM platform to multivariate time series data about ourselves and other persons. It could be advantageous for persons to offer both their genotypes and their EBM-2G quantitative temporal-interaction phenotypes.

The specified CASM platform helps genomics fulfill its promise in the form of EBM-2G. More generally, the specified CASM platform helps advance basic and applied sciences of CAS.

11. The Reproducibility Crisis and Measurement Deficiency Anemia

Science is amid a reproducibility crisis. For example, the United States NIH has expressed concern about scientific rigor and reproducibility. However, there appears to be no focus in medicine on the role of measurement and metrology to quantify how persons work in the time dimension (FIG. 1A), including clinical trials that need to measure evidence for action variable benefit and harm for individuals to evaluate safety and effectiveness for both individuals and populations. One factor contributing to lack of reproducibility is outmoded experimental design. EBM-2G RCT designs (Section 7) often need to supersede GAS RCT designs when EBM-2G RCT designs are an option because both independent and dependent variables can be studied as action variables, distinct from categorical variables.

12. Computational Details

This section provides additional details and demonstrations about major steps 3 through 10 in the Section 4 CASM overview.

12.1. Digitize any and all Dimensional Time Series:

This section provides more details about Section 4.3. The specified CASM platform's unique capabilities to quantify how individual CAS work in the time dimension (FIG. 1A) derives from the fact that the specified CASM platform digitizes any and all dimensional time series before computing temporal-interaction or temporal-interaction benefit-and-harm scores. Dimensional time series have more than two distinct levels or values.

FIG. 6 is a table 600 illustrating example digitization at an ordinal level of measurement for two different time series, dose, and response variable level. Liken the advantages of digitization for processing multivariate time series data to advantages of digital photography compared to film photography.

FIG. 6 shows digitization at an ordinal level of measurement for two different time series, dose, and response variable level. Dose has four levels (0 or placebo, 20, 40, and 80) and yields three digital series that include both 1s and 0s. The response variable has 12 levels and yields 11 digital series that include both 1s and 0s. Another option would be for the specified CASM platform to digitize time series at an interval level.

Let FIG. 6 be about using three non-zero doses of an antihypertensive, an independent action variable, to control blood pressure, a dependent or response action variable. Let lower levels of blood pressure be toward and beneficial. The rows indicated with circle 10 in FIG. 6 show that when doses of the antihypertensive were 40 or more, blood pressure never was 91 or higher. Such a pattern is not apt to be random. As shown in Sections 12.4, 12.5, and 12.6, these two series will yield a standardized temporal-interaction benefit-and-harm score with a magnitude of 8.92 standard deviation units or bagnes.

There are additional ways to digitize time series as part of the specified CASM platform. Digitization can be performed without the necessary loss of information. However, digitization that results in large numbers of digital series for each dimensional time series rapidly drives up demand for computing resources. Furthermore, experience suggests a limited value deriving from high levels of dimensional resolution. Accordingly, the specified CASM platform's software embodiments could reduce the dimensional resolution to reduce computing resources demand. Existing software embodiments use an option of either seven or thirteen levels of dimensional resolution.

Independent action variable level and dependent action variable level are required analysis parameters whenever independent or dependent action variables have more than two levels.

12.2. Apply Optional Analysis Parameters:

This section provides more details about Section 4.4. Section 12.1 presented how the specified CASM platform represents each dimensional series with a set of digital series. Next, this section is about applying rules to the required digital series, creating additional and optional digital time series to find more complicated patterns of temporal interaction in multivariate time series. As examples, users of the specified CASM platform can generate additional digital time series for optional analysis parameters that account for temporal phenomena such as episodes of events, delay of response, and response persistence.

12.2.1. Episodes of Events:

The specified CASM platform allows users to study any effects of episodes of independent events on episodes of dependent events. Present embodiments of the specified CASM platform enable users to use up to four optional analysis parameters to account for episodes. These are independent variable episode length (IVEL), independent variable episode criterion (IVEC), dependent variable episode length (DVEL), and dependent variable episode criterion (DVEC). The default level of each of these four analysis parameters is one when users do not select additional levels.

To illustrate the value of being able to study independent action variable episodes, consider a patient having been prescribed a specified daily dose of a drug to lower high blood pressure. Patients have been known not to comply or adhere to prescribed treatment regimens. Non-adherence can affect blood pressure control. Quantifying effects of patient non-adherence to prescribed treatment regimens has been identified as an important but still largely unmet need. The specified CASM platform would allow users, for example, to study how episodes of drug consumption might affect episodes of blood pressure events.

FIG. 7 is a table 700 illustrating an example of how an embodiment of a CASM platform is configured to study up to 36 combinations of episode length and episode criterion for independent events and episodes of dependent events. In particular, FIG. 7 illustrates how a current embodiment of the specified CASM platform can study up to 36 combinations of episode length and episode criterion for independent events and episodes of dependent events. As one example, it is possible to study possible effects of taking an antihypertensive on any five, an instance of IVEC, of seven days in a moving window of time, an instance of IVEL. More specifically, evidence of temporal-interaction benefit and harm can be quantified as functions of the level of all four optional analysis parameters used to define episodes of events. Such information can help decision-makers identify what level of adherence optimizes safe and effective treatment across multiple response action variables as when an antihypertensive causes side effects.

12.2.2. Delay of Effect and Effect Persistence:

The value of delay of effect and effect persistence will be illustrated in drug development and use. Drug responses can be delayed based, at least in part, on time taken for drug absorption and/or distribution. Drug effects can persist based, at least in part, on time taken for drug metabolism and/or excretion. Adsorption, distribution, metabolism, and excretion can occur at different rates. Accordingly, delay of response and response persistence need to be investigated as independently as possible. Although the delay of effect and effect persistence are being illustrated for response as FIG. 1A operationally defines response, delay of effect and effect persistence also apply to internal function and agency. For example, there are delayed effects for internal bodily function such as when it takes time for secretion of one hormone to affect secretion of other hormones and when it takes time for activity in one brain region to affect activity in other brain regions.

FIG. 8 is a table 800 illustrating an example of how a CASM platform detects and quantifies evidence for delay of response. In particular, FIG. 8 illustrates the use of mock data to demonstrate how the specified CASM platform detects and quantifies evidence for delay of response. The data for the top part of FIG. 8 is for one independent variable (IV) and seven dependent variables (DV) time series with delays of response to the IV of 0 through 6 time periods, respectively.

FIG. 9 is a table 900 illustrating an example of how a CASM platform correctly identifies and quantifies the response delays of FIG. 8. In particular, FIG. 9 shows how the specified CASM platform correctly identifies and quantifies the response delays in FIG. 8, with summary scores having the largest magnitudes. This same approach applies to all combinations of digital time series resulting from the digitization of analog or dimensional time series (Section 12.1).

FIG. 10 is a table 1000 and a table 1002 illustrating an example of how a CASM platform correctly identifies and quantifies evidence for effect persistence (P). In particular, FIG. 10 demonstrates example tables 1000 and 1002 showing how the specified CASM platform correctly identifies and quantifies evidence for effect persistence (P).

FIG. 11 is a table 1102 illustrating example mock data 1100 for use in demonstrating how users of a CASM platform obtain correct results investigating delay of response and response persistence simultaneously. In particular, the top table 1100 of the FIG. 11 shows the data with a delay of response=1 and response persistence=3. The bottom table 1102 of FIG. 11 shows temporal-interaction scores as functions of the optional analysis parameters called delay of response and response persistence. The summary temporal-interaction score has a value of 10.5663 standard deviations units, bagnes when computed with the specified CASM platform. This score's location in the 2-dimensional array of standardized temporal-interaction scores correctly identifies the levels of delay of response and response persistence that yield the most evidence for the temporal interaction.

12.3. Define Optional Boolean Events:

This section provides more detail about Section 4.5. Two or more independent or predictor action variables often act together to affect a dependent or predicted action variable. For example, two distinct types of drugs might interact to have effects of distinct types or magnitudes than either type of drug alone. For example, clonidine for blood pressure and propranolol for anxiety can interact to have dangerous effects on blood pressure. Drug-drug interactions illustrate a form of non-linearity (Section 6.4). Users of the specified CASM platform can use Boolean operation AND independent events, defined on required and optional analysis parameters and their digital series, to investigate such phenomena.

FIG. 12 shows mock data 1200 and benefit-and-harm scores 1202 for two distinct types of drugs that appear to interact to increase occurrences of an adverse event defined on a dependent variable (DV). The specified CASM platform transforms any dimensional or analog time series into sets of digital series, as described in Sections 4.3 and 12.1. Users can investigate Boolean events across all digital series that represent analog or dimensional time series.

The specified CASM platform can also investigate Boolean-dependent events as for syndromes using additional Boolean operators (OR, NOT, AND NOT), and more time series. Also, Boolean dependent events can be based on counts across multiple response variables. For example, one definition of a major depressive episode comprises experiencing at least 5 of 9 signs or symptoms nearly every day. This Boolean dependent event could be used to evaluate antidepressants.

12.4. Generate 2×2 Tables:

This section provides more detail about Section 4.6. FIG. 13 is a table 1300 and a table 1302 illustrating an example of generating of a 2×2 table using the two digital time series identified by circles 10 in FIG. 6. Values in each of the four cells of the 2×2 table are counts of time periods for [1,1]; [0,1]; [1,0]; and [0,0].

The specified CASM platform generates multidimensional arrays of 2×2 tables. Each 2×2 table results from the combination of one digital series for one or more independent (treatment) action variables and one or more dependent (response) action variables. Dimensions of such 2×2 tables correspond to analysis parameters such as drug dose, response variable level, IVEL, IVEC, DVEL, DVEC, delay of response, and response persistence.

12.5. Compute Raw Temporal-Interaction Scores:

This section provides more detail about Section 4.7. The specified CASM platform computes a raw or unstandardized temporal-interaction score or a raw temporal-interaction benefit-and-harm score for each 2×2 table by:

1. Computing the magnitude or absolute value of the raw temporal-interaction score or temporal-interaction benefit-and-harm score,
2. Computing the expected value of the a-cell of the 2×2 table, and
3. Applying a three-part rule.

FIG. 14 is an example process 1400 including a set of equations and determinations for computation of a raw temporal-interaction benefit-and-harm score using a 2×2 table. In particular, FIG. 14 illustrates all three of these steps for computation of the raw temporal-interaction benefit-and-harm (B&H) score using the 2×2 table in Section 12.5. The raw B&H score=16.000 because higher levels of the dependent action variable, blood pressure, were considered untoward, as described in Section 12.1.

12.6. Mathematical Standardization of Temporal-Interaction Scores:

This section provides more detail about Section 4.8. Standardization increases the value of measurement. Accordingly, as introduced in Section 1, NIST has set forth SI units of measurement. The specified CASM platform provides a universal mathematically standardized unit of measurement for temporal-interaction scores and temporal-interaction benefit-and-harm scores. CASM standardization is based entirely on mathematics, including probabilities.

FIG. 15 is an example table 1500 illustrating an example standardization of a raw temporal-interaction benefit-and-harm score. In particular, FIG. 15 demonstrates the standardization of the raw temporal-interaction benefit-and-harm score shown in Section 12.5 from the observed 2×2 table shown in Section 12.4.

Column 1 identifies all 2×2 tables possible given the observed 2×2 table's marginal frequencies. The first 2×2 table in Column 1 happens to be the observed 2×2 table.

Column 2 shows the raw temporal-interaction benefit-and-harm score for each possible 2×2 table as computed according to Section 12.5.

Column 3 shows the probability of obtaining each possible raw temporal-interaction benefit-and-harm score by random chance. These are hypergeometric probabilities re-purposed for the specified CASM platform and computed with the equation 1600 shown in FIG. 16. FIG. 16 is an example equation 1600 for determining hypergeometric probabilities re-purposed for a CASM platform. Although illustrated for temporal-interaction benefit-and-harm scores, the computations in FIG. 16 also apply to temporal-interaction scores.

Column 4 shows the universally standardized temporal-interaction benefit-and-harm score for each possible 2×2 table. Achieve universal standardization as shown in FIG. 17. FIG. 17 is an example process 1700 for generating universal and mathematically standardized temporal-interaction scores.

Each temporal-interaction score and each temporal-interaction benefit-and-harm score computed with the specified CASM platform is one score from a distribution of potential scores having mean=0 and standard deviation=1 unless 0 is the only possible score. Zero is the only possible score when there is no variation in the dependent action variable, the independent action variable, or both.

12.7. Summarize:

This section provides more detail about Section 4.9. The specified CASM platform can yield huge multidimensional arrays of standardized temporal-interaction scores. Array size depends mainly on options users select when creating CASM scoring protocols (Section 1). For example, an operational software embodiment of the specified CASM platform can yield up to an 8-dimensional array of 6,531,840 standardized scores to quantify evidence for a temporal interaction between one independent action variable and one dependent action variable. This number, 6,531,840, is the product ($12 \times 12 \times 36 \times 36 \times 7 \times 5$) of all available levels in a particular software embodiment as follows.

1. 12 levels of the independent or predictor action variable
2. 12 levels of the dependent or predicted action variable
3. 36 is a total for two analysis parameters used to define episodes of independent events, as identified in Section 12.2.1 and FIG. 7.
4. 36 is a total for two analysis parameters used to define episodes of dependent events
5. 7 levels for delay of effect, 0 through 6
6. 5 levels for effect persistence, 1 through 5.

Fortunately, standardization (Section 12.6) makes it easy to summarize entire arrays by identifying the temporal-interaction or temporal-interaction benefit-and-harm score with the largest magnitude, positive or negative. The summary score's location in a multidimensional array identifies all analysis parameter levels and Boolean events that provide the most evidence for temporal interaction.

Sometimes more than one set of conditions yield the same summary score, all of which can be identified. The specified CASM platform can yield small summary scores of equal magnitudes but opposite signs on some occasions. Summarize these as 0.

Multidimensional arrays often can be summarized in their entirety with a single summary score. Additionally, arrays can be summarized across each analysis parameter or any combination of analysis parameters. Typically, temporal-interaction scores as functions of analysis parameters are not linear (Section 6.4). One practical application of summarization for EBM-2G is to help identify optimal safe and effective drug doses for individual patients.

12.8. Estimate Quantitative Significance of Summary Temporal-Interaction Scores:

This section provides more detail about Section 4.10 that already introduced CASM significance. Increasing CASM significance about individuals improves statistical significance as in EBM-2G RCT group designs (Section 7). This section applies to both temporal-interaction scores and temporal-interaction benefit-and-harm scores.

Section 12.7 showed how users of the specified CASM platform could interrogate vast search spaces for temporal interaction patterns. A total of 6,531,840 options is a vast search space for a temporal interaction or relationship between two time series.

The specified CASM platform can be used in either a data mining and pattern-recognition mode or a hypothesis-testing mode. Vast search spaces can be helpful while mining data. However, vast search spaces can lead to false-positive results. Accordingly, it is essential and valuable to estimate the quantitative significance of summary temporal-interaction scores when testing hypotheses. Hypothesis testing includes estimating the quantitative significance of results from EBM-2G single-person RCT designs (Section 7.1) and EBM-2G quantitative temporal-interaction phenotypes and phenotype tests (Section 9). One strategy to increase CASM quantitative significance when testing hypotheses is to limit search-space size.

The practical value of combining data mining and hypothesis testing that includes the specified CASM platform and statistics (Section 3.5) can be illustrated for EBM-2G drug development as during the transition from preclinical research to clinical research with persons. This transition is a time of great uncertainty about indications, contraindications, and doses.

The method and system to estimate the quantitative significance of temporal-interaction and temporal-interaction benefit-and-harm scores are based on permutation tests. Permutation tests have been used in the discipline of statistics to use results from samples of individuals to test hypotheses about populations. In contrast, the specified CASM platform uses permutation tests to test hypotheses about individual CAS themselves. Permutation tests performed with the specified CASM platform are an extension from Section 12.1 through Section 12.7 just above.

Permutation tests with the specified CASM platform include four main steps.

1. Randomly permuting the temporal order of one or more of the time series from which the temporal-interaction summary score or temporal-interaction benefit-and-harm score was computed,
2. Computing a summary score by applying the same specified CASM platform scoring protocol that was used to obtain the observed summary temporal-interaction or observed temporal-interaction benefit and harm summary score to the permuted data to obtain a permuted data temporal-interaction score or temporal-interaction benefit-and-harm score summary score,
3. Repeating the two previous steps a large multitude (e.g., thousands) of times to generate a probability distribution of temporal-interaction summary scores or temporal-interaction benefit-and-harm scores from permuted data with one summary score for each permuted order,
4. Relating the observed temporal-interaction summary score or summary temporal-interaction benefit-and-harm score to the probability distribution of permuted data temporal-interaction summary scores or summary temporal-interaction benefit-and-harm score to:
   a. Estimate the quantitative significance using a two-tailed test by determining the proportion of permuted data summary scores equal to or greater than the absolute value of the observed summary temporal-interaction score or observed summary temporal-interaction benefit-and-harm score,
   b. Estimate the quantitative significance of a one-tailed test for the negative tail by determining the proportion of negative permuted order temporal-interaction summary scores equal to or greater in magnitude than the observed temporal-interaction summary score or the observed temporal-interaction benefit-and-harm score,
   c. Estimate the quantitative significance of a one-tailed test for the positive tail by determining the proportion of positive permuted order temporal-interaction summary scores or summary temporal-interaction benefit-and-harm scores equal to or greater in magnitude than the observed temporal-interaction summary score or observed temporal-interaction benefit-and-harm score.

Quantitatively significant summary temporal-interaction scores and temporal-interaction benefit-and-harm scores are more apt to be of value for basic and applied sciences of CAS than scores that could have resulted from random chance.

FIG. 18 is a flow diagram illustrating a process 1800 for using Complex Adaptive Systems Metrology (CASM) to generate scores and CASM significance estimates for said scores. The process 1800 may be carried out via computing system 124 (FIG. 1B) using work 100 (FIG. 1A) and the CASM platform described herein. In some embodiments, the process 1800 is a computer-implemented complex adaptive systems metrology (CASM) method for generating universally and mathematically standardized scores that quantify longitudinal evidence for either temporal-interaction scores or temporal-interaction benefit-and-harm scores. Each step below is described in detail with respect to sections 3-9 above and with respect to FIG. 1B. The computing system 124 may carry out instructions of the process 1800 using at least one processor and one or more computer-readable hardware storage devices having stored thereon computer-executable instructions that are executable by the at least one processor.

At block 1802, the process 1800 includes receiving a set of data about an individual complex adaptive system, where the set of data includes multivariate time-series action variables. For example, the computing system 124 may receive a set of data 132 about an individual complex adaptive system, the set of data may include multivariate time-series action variables (e.g., variables 150 and 152) representing the individual complex adaptive system.

At block 1804, the process 1800 includes pre-processing the set of data. The pre-processing may include decomposing portions of the data to distinguish temporal interactions from effects of longer-term linear and nonlinear trends. For example, the computing system 124 may pre-process the set of data 132. The pre-processing may be performed by the pre-processor/digitizer 138.

At block 1806, the process 1800 includes digitizing each time series action variable in the set of data that has more than two levels to a set of digital time series comprised of zeros and ones to determine analysis parameters. For example, the pre-processor/digitizer 138 may digitize each time series action variable (150, 152) in the set of data that has more than two levels to a set of digital time series 162 comprised of zeros and ones to generate analysis parameters 144. The analysis parameters 144 may include at least an independent action variable level for one or more independent action variables associated with at least a portion of the set of data 132 and a dependent action variable level for one or more dependent action variables associated with at least a portion of the set of data 132.

At block 1808, the process 1800 includes selecting computation of either temporal-interaction scores or temporal-interaction benefit-and-harm scores. For example, the score generator 140 may determine to select either the computation of either temporal-interaction scores 154 or temporal-interaction benefit-and-harm scores 156.

At block 1810, the process 1800 includes determining additional analysis parameters by generating one or more additional sets of digital time series, the generating including applying operationally defined rules to the digitized set of digital time series for one or more independent action variables or the digitized set of digital time series for one or more dependent action variables. For example, the computing system 124 may determine additional analysis parameters 146 by generating one or more additional sets of digital time series 163. The generating of the additional sets of digital time series 163 may include applying operationally defined rules 176 to the digitized set of digital time series 162 for one or more independent action variables or the digitized set of digital time series for one or more dependent action variables.

At block 1812, the process 1800 includes cross classifying each digital time series for a respective independent action variable or set of independent action variables with each digital time series for a time series for a respective dependent action variable or set of dependent action variables, the cross-classifying comprising generating one or more multidimensional arrays of tables (e.g., 2×2 tables). For example, the computing system 124 may employ the classifier 164 to cross-classify each digital time series 162 for a respective independent action variable or set of independent action variables 150 with each digital time series 162 for a time series for a respective dependent action variable or set of dependent action variables 152. The cross-classifying may include generating one or more multidimensional arrays of tables 168 (e.g., 2×2 tables) where each array has at least one dimension for each of the analysis parameters 144 or the additional analysis parameters 146 and at least one multidimensional array 170 for a plurality of events 153 associated with the one or more independent action variables 150 and one or more dependent action variables 152.

At block 1814, the process 1800 includes computing, for each of the 2×2 tables, either a raw and unstandardized temporal-interaction score or a raw and unstandardized benefit-and-harm score. For example, the computing system 124 may compute, for each of the tables 168, either a raw and unstandardized temporal-interaction score or a raw and unstandardized benefit-and-harm score.

At block 1816, the process 1800 includes standardizing each raw and unstandardized temporal-interaction score or each benefit-and-harm score so that each standardized score represents one score from a distribution of potential scores defined by the set of data in combination with an operationally defined CASM scoring protocol where each resulting distribution of potential scores has a mean of 0 and a standard deviation of 1 unless 0 is the only potential score. For example, the computing system 124 may standardize each raw and unstandardized temporal-interaction score or each benefit-and-harm score so that each standardized score represents one score from a distribution of potential scores defined by the set of data 132.

At block 1818, the process 1800 includes generating a summary score or set of summary scores for each multidimensional array. For example, the computing system 124 may employ score generator 140 to generate a summary score 158 or set of summary scores for each multidimensional array 170. The summary score 158 may be based on either the standardized temporal-interaction scores or the standardized temporal-interaction benefit-and-harm scores.

At block 1820, the process 1800 includes determining, based on the generated summary score for each multidimensional array, a CASM quantitative significance estimate of the generated summary score for either the standardized temporal-interaction scores or the standardized temporal-interaction benefit-and-harm scores. For example, the computing system 124 may determine, based on the generated summary score 158 for each multidimensional array 170, a quantitative significance estimate 136 of the generated summary score 158 for either the standardized temporal-interaction scores or the standardized temporal-interaction benefit-and-harm scores.

The systems and methods of the preferred embodiment and variations thereof can be embodied and/or implemented at least in part as a machine configured to receive a computer-readable medium storing computer-readable instructions. The instructions are preferably executed by computer-executable components, preferably integrated with the system and one or more portions of the processor on a server and/or computing device. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

As used in the description and claims, the singular form "a," "an" and "the" include both singular and plural references unless the context clearly dictates otherwise. For example, the term "variable" may include, and is contemplated to include, a plurality of variables. At times, the claims and disclosure may include terms such as "a plurality," "one or more," or "at least one;" however, the absence of such terms is not intended to mean, and should not be interpreted to mean, that a plurality is not conceived.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A computer-implemented method for determining evidence for measuring internal function in an individual representing a complex adaptive system, the method comprising:

receiving multivariate time series data comprising action variables representing the individual;

decomposing the time series data to distinguish evidence for regulatory temporal interactions from linear and nonlinear trends in the action variables;

digitizing each action variable having more than two levels to a set of digital time series comprising zeros and ones to generate analysis parameters, wherein the analysis parameters include at least one independent action variable level for one or more independent action variables and at least one dependent action variable level for one or more dependent action variables, wherein the independent action variables and the dependent action variables quantify the internal function of the individual;

determining additional analysis parameters by generating a plurality of additional sets of digital time series, the generating including applying operationally defined rules to the digitized set of digital time series, wherein the additional analysis parameters include delay of regulatory response and persistence of regulatory effects;

cross-classifying each digital time series for a respective independent action variable with each digital time series for a respective dependent action variable, the cross-classifying comprising generating one or more multidimensional arrays of tables;

computing, for each of the tables, a raw and unstandardized temporal-interaction score;

standardizing each raw and unstandardized temporal-interaction score;

generating a summary regulatory control score for each multidimensional array, the summary score being based on the standardized temporal-interaction scores, wherein:

a positive summary score indicates evidence of ordered regulatory control and a negative summary score indicates evidence of dysregulation and disordered regulatory mechanisms;

determining, based on the generated summary regulatory control score for each multidimensional array, a quantitative significance estimate of the generated summary regulatory control score using permutation tests that randomly permute a temporal order of one or more of the time series; and applying the summary regulatory control scores and associated quantitative significance estimates to assess regulatory function in the individual, wherein dysregulation evidenced by quantitatively significant negative summary scores indicates a disordered internal function for the individual.

2. The computer-implemented method of claim 1, wherein the internal function represents a measure of an extent of endogenous insulin level regulation on blood glucose levels of the individual.

3. The computer-implemented method of claim 1, wherein the independent action variables and the dependent action variables quantifying the internal function comprise hormone levels, wherein the temporal interactions quantify how secretion of one hormone affects secretion of another hormone.

4. The computer-implemented method of claim 1, wherein the independent action variables and the dependent action variables quantifying the internal function comprise brain activity measures, wherein temporal interactions quantify functional connectivity between brain regions of the individual.

5. The computer-implemented method of claim 1, wherein the independent action variables and the dependent action variables quantifying the internal function comprise electrophysiological variables that quantify nervous system signaling in the individual.

6. The computer-implemented method of claim 1, wherein the independent action variables and the dependent action variables quantifying the internal function comprise neurotransmitter system activity levels for the individual including at least one of: cholinergic, glutamatergic, serotonergic, dopaminergic, and histaminergic systems.

7. The computer-implemented method of claim 1, wherein the independent action variables and the dependent action variables quantifying the internal function comprise protein levels for the individual, wherein temporal interactions quantify protein-protein signaling interactions between signaling proteins.

8. The computer-implemented method of claim 1, wherein the independent action variables and the dependent action variables quantifying the internal function comprise activity levels in frequency bands from electroencephalography, wherein the frequency bands include gamma, beta, alpha, theta, and delta bands.

9. The computer-implemented method of claim 1, wherein the independent action variables and the dependent action variables quantifying the internal function comprise levels of biologically active molecules in biofluids that interact in regulatory control systems of the individual.

10. The computer-implemented method of claim 1, wherein the internal function represents regulatory control mechanisms for maintaining homeostasis corresponding to survival of the individual.

11. The computer-implemented method of claim 1, wherein the independent action variables and the dependent action variables quantifying the internal function comprise measures of coordinated action between biological systems of the individual, and wherein the coordinated action is distinguished from uncoordinated action.

12. The computer-implemented method of claim 1, wherein the internal function represents cell signaling, nervous system signaling, and hormonal signaling systems associated with maintaining homeostasis in the individual.

13. A complex adaptive systems metrology (CASM) system for determining evidence for measuring internal function in an individual representing a complex adaptive system, the system comprising:

at least one processing device; and memory storing instructions that when executed cause the at least one processing device to perform operations comprising:

receiving multivariate time series data comprising action variables representing the individual;

decomposing the time series data to distinguish evidence for regulatory temporal interactions from linear and nonlinear trends in the action variables;

digitizing each action variable having more than two levels to a set of digital time series comprising zeros and ones to generate analysis parameters, wherein the analysis parameters include at least one independent action variable level for one or more independent action variables and at least one dependent action variable level for one or more dependent action variables, wherein the independent action variables and the dependent action variables quantify the internal function of the individual;

determining additional analysis parameters by generating a plurality of additional sets of digital time series, the generating including applying operationally defined rules to the digitized set of digital time series, wherein the additional analysis parameters include delay of regulatory response and persistence of regulatory effects;

cross-classifying each digital time series for a respective independent action variable with each digital time series for a respective dependent action variable, the cross-classifying comprising generating one or more multidimensional arrays of tables;

computing, for each of the tables, a raw and unstandardized temporal-interaction score;

standardizing each raw and unstandardized temporal-interaction score;

generating a summary regulatory control score for each multidimensional array, the summary score being based on the standardized temporal-interaction scores, wherein:

a positive summary score indicates evidence of ordered regulatory control and a negative summary score indicates evidence of dysregulation and disordered regulatory mechanisms;

determining, based on the generated summary regulatory control score for each multidimensional array, a quantitative significance estimate of the generated summary regulatory control score using permutation tests that randomly permute a temporal order of one or more of the time series; and applying the summary regulatory control scores and associated quantitative significance estimates to assess regulatory function in the individual, wherein dysregulation evidenced by quantitatively significant negative summary scores indicates a disordered internal function for the individual.

14. The system of claim 13, wherein the internal function represents a measure of an extent of endogenous insulin level regulation on blood glucose levels of the individual.

15. The system of claim 13, wherein the independent action variables and the dependent action variables quantifying the internal function comprise hormone levels, wherein the temporal interactions quantify how secretion of one hormone affects secretion of another hormone.

16. The system of claim 13, wherein the independent action variables and the dependent action variables quantifying the internal function comprise brain activity measures, wherein temporal interactions quantify functional connectivity between brain regions of the individual.

17. The system of claim 13, wherein the independent action variables and the dependent action variables quantifying the internal function comprise electrophysiological variables that quantify nervous system signaling in the individual.

18. The system of claim 13, wherein the independent action variables and the dependent action variables quantifying the internal function comprise neurotransmitter system activity levels for the individual including at least one of: cholinergic, glutamatergic, serotonergic, dopaminergic, and histaminergic systems.

19. The system of claim 13, wherein the independent action variables and the dependent action variables quantifying the internal function comprise protein levels for the individual, wherein temporal interactions quantify protein-protein signaling interactions between signaling proteins.

20. The system of claim 13, wherein the independent action variables and the dependent action variables quantifying the internal function comprise activity levels in frequency bands from electroencephalography, wherein the frequency bands include gamma, beta, alpha, theta, and delta bands.

21. The system of claim 13, wherein the independent action variables and the dependent action variables quantifying the internal function comprise levels of biologically active molecules in biofluids that interact in regulatory control systems of the individual.

22. The system of claim 13, wherein the internal function represents regulatory control mechanisms for maintaining homeostasis corresponding to survival of the individual.

23. The system of claim 13, wherein the independent action variables and the dependent action variables quantifying the internal function comprise measures of coordinated action between biological systems of the individual, and wherein the coordinated action is distinguished from uncoordinated action.

24. The system of claim 13, wherein the internal function represents cell signaling, nervous system signaling, and hormonal signaling systems associated with maintaining homeostasis in the individual.

25. A non-transitory computer-readable medium for a complex adaptive systems metrology (CASM) for determining evidence measuring internal function in an individual representing a complex adaptive system, comprising:

at least one processor; and a memory storing instructions that, when executed by the at least one processor, cause the at least one processor to perform operations comprising:

receiving multivariate time series data comprising action variables representing the individual;

decomposing the time series data to distinguish evidence for regulatory temporal interactions from linear and nonlinear trends in the action variables;

digitizing each action variable having more than two levels to a set of digital time series comprising zeros and ones to generate analysis parameters, wherein the analysis parameters include at least one independent action variable level for one or more independent action variables and at least one dependent action variable level for one or more dependent action variables, wherein the independent action variables and the dependent action variables quantify the internal function of the individual;

determining additional analysis parameters by generating a plurality of additional sets of digital time series, the generating including applying operationally defined rules to the digitized set of digital time series, wherein the additional analysis parameters include delay of regulatory response and persistence of regulatory effects;

cross-classifying each digital time series for a respective independent action variable with each digital time series for a respective dependent action variable, the cross-classifying comprising generating one or more multidimensional arrays of tables;

computing, for each of the tables, a raw and unstandardized temporal-interaction score;

standardizing each raw and unstandardized temporal-interaction score;

generating a summary regulatory control score for each multidimensional array, the summary score being based on the standardized temporal-interaction scores, wherein:

a positive summary score indicates evidence of ordered regulatory control and a negative summary score indicates evidence of dysregulation and disordered regulatory mechanisms;

determining, based on the generated summary regulatory control score for each multidimensional array, a quantitative significance estimate of the generated summary regulatory control score using permutation tests that randomly permute a temporal order of one or more of the time series; and applying the summary regulatory control scores and associated quantitative significance estimates to assess regulatory function in the individual, wherein dysregulation evidenced by quantitatively significant negative summary scores indicates a disordered internal function for the individual.

26. The non-transitory computer-readable medium of claim 25, wherein the internal function represents a measure of an extent of endogenous insulin level regulation on blood glucose levels of the individual.

27. The non-transitory computer-readable medium of claim 25, wherein the independent action variables and the dependent action variables quantifying the internal function comprise hormone levels, wherein the temporal interactions quantify how secretion of one hormone affects secretion of another hormone.

28. The non-transitory computer-readable medium of claim 25, wherein the independent action variables and the dependent action variables quantifying the internal function comprise brain activity measures, wherein temporal interactions quantify functional connectivity between brain regions of the individual.

29. The non-transitory computer-readable medium of claim 25, wherein the independent action variables and the dependent action variables quantifying the internal function comprise electrophysiological variables that quantify nervous system signaling in the individual.

30. The non-transitory computer-readable medium of claim 25, wherein the independent action variables and the dependent action variables quantifying the internal function comprise neurotransmitter system activity levels for the individual including at least one of: cholinergic, glutamatergic, serotonergic, dopaminergic, and histaminergic systems.

31. The non-transitory computer-readable medium of claim 25, wherein the independent action variables and the dependent action variables quantifying the internal function comprise protein levels for the individual, wherein temporal interactions quantify protein-protein signaling interactions between signaling proteins.

32. The non-transitory computer-readable medium of claim 25, wherein the independent action variables and the dependent action variables quantifying the internal function comprise activity levels in frequency bands from electroencephalography, wherein the frequency bands include gamma, beta, alpha, theta, and delta bands.

33. The non-transitory computer-readable medium of claim 25, wherein the independent action variables and the dependent action variables quantifying the internal function comprise levels of biologically active molecules in biofluids that interact in regulatory control systems of the individual.

34. The non-transitory computer-readable medium of claim 25, wherein the internal function represents regulatory control mechanisms for maintaining homeostasis corresponding to survival of the individual.

35. The non-transitory computer-readable medium of claim 25, wherein the independent action variables and the dependent action variables quantifying the internal function comprise measures of coordinated action between biological systems of the individual, and wherein the coordinated action is distinguished from uncoordinated action.

36. The non-transitory computer-readable medium of claim 25, wherein the internal function represents cell signaling, nervous system signaling, and hormonal signaling systems associated with maintaining homeostasis in the individual.

* * * * *